(12) United States Patent
Jia et al.

(10) Patent No.: US 10,295,490 B2
(45) Date of Patent: May 21, 2019

(54) MEMS-BASED CALORIMETER, FABRICATION, AND USE THEREOF

(71) Applicant: The Trustees Of Columbia University In the City of New York, New York, NY (US)

(72) Inventors: Yuan Jia, New York, NY (US); Zhixing Zhang, New York, NY (US); Qiao Lin, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 15/495,677

(22) Filed: Apr. 24, 2017

(65) Prior Publication Data

US 2017/0307553 A1    Oct. 26, 2017

Related U.S. Application Data

(63) Continuation-in-part of application No. PCT/US2015/057384, filed on Oct. 26, 2015.
(Continued)

(51) Int. Cl.
*G01N 25/00*    (2006.01)
*G01N 25/48*    (2006.01)
(Continued)

(52) U.S. Cl.
CPC ......... *G01N 25/482* (2013.01); *G01K 17/006* (2013.01); *G01N 25/20* (2013.01)

(58) Field of Classification Search
CPC combination set(s) only.
See application file for complete search history.

(56) References Cited

U.S. PATENT DOCUMENTS

| 6,561,692 B2 | 5/2003 | Danley |
| 7,344,681 B1* | 3/2008 | Fiechtner ............ B01F 13/0093 366/DIG. 1 |

(Continued)

FOREIGN PATENT DOCUMENTS

| WO | WO 2012/116092 A1 | 8/2012 |
| WO | WO 2014/018688 A2 | 1/2014 |

OTHER PUBLICATIONS

Barnes et al., "A femtojoule calorimeter using micromechanical sensors," Review of Scientific Instruments 65(12):3793-3798 (1994).
(Continued)

*Primary Examiner* — Lisa M Caputo
*Assistant Examiner* — Nasir U. Ahmed
(74) *Attorney, Agent, or Firm* — Baker Botts L.L.P.

(57) ABSTRACT

A MEMS-based calorimeter includes a reference channel, a sample channel, and a thermopile configured to measure a temperature differential between the reference channel and a sample channel. The reference channel and the sample channel each include a passive mixer such as a splitting-and-recombination micromixer. The passive mixer can be formed by a first set of channels in a first layer and a second set of channels in a second layer. Methods for fabricating the MEMS-based calorimeter and methods of using the calorimeter to measure thermodynamic properties of chemical reactions are also provided.

22 Claims, 56 Drawing Sheets

Related U.S. Application Data

(60) Provisional application No. 62/068,562, filed on Oct. 24, 2014.

(51) Int. Cl.
*G01N 25/20* (2006.01)
*G01K 17/00* (2006.01)

(56) References Cited

U.S. PATENT DOCUMENTS

| | | | | |
|---|---|---|---|---|
| 8,313,906 | B2* | 11/2012 | Cao | C12N 15/1017 435/283.1 |
| 2003/0225360 | A1* | 12/2003 | Eppstein | A61M 37/0015 604/19 |
| 2005/0238080 | A1 | 10/2005 | Wolkin et al. | |
| 2010/0116429 | A1* | 5/2010 | Berkey | B01J 19/0093 156/249 |
| 2013/0131389 | A1* | 5/2013 | Loeffler | C07C 41/02 568/623 |
| 2015/0285751 | A1* | 10/2015 | Lin | B01L 3/502715 436/501 |

OTHER PUBLICATIONS

Cavicchi et al., "Micro-differential scanning calorimeter for combustible gas sensing," Sensors and Actuators B, 97:22-30 (2004).
International Search Report dated Mar. 2, 2016 in International Application No. PCT/US15/57384.
Lai et al., "High-speed ($10^{4\circ}$ C./s) scanning microcalorimetry with monolayer sensitivity ($J/m_2$)," Applied Physics Letters 67:1229-1231 (1995).
Vanden Poel et al., "Performance and calibration of the Flash DSC 1, a new, MEMS-based fast scanning calorimeter," Journal of Thermal Analysis and Calorimetry 110:1533-1546 (2012).
Wang et al., "A MEMS Isothermal Titration Biocalorimeter," 16th International Conference on Miniaturized Systems for Chemistry and Life Sciences, Oct. 28-Nov. 1, 2012, Okinawa, Japan, pp. 195-197.

* cited by examiner

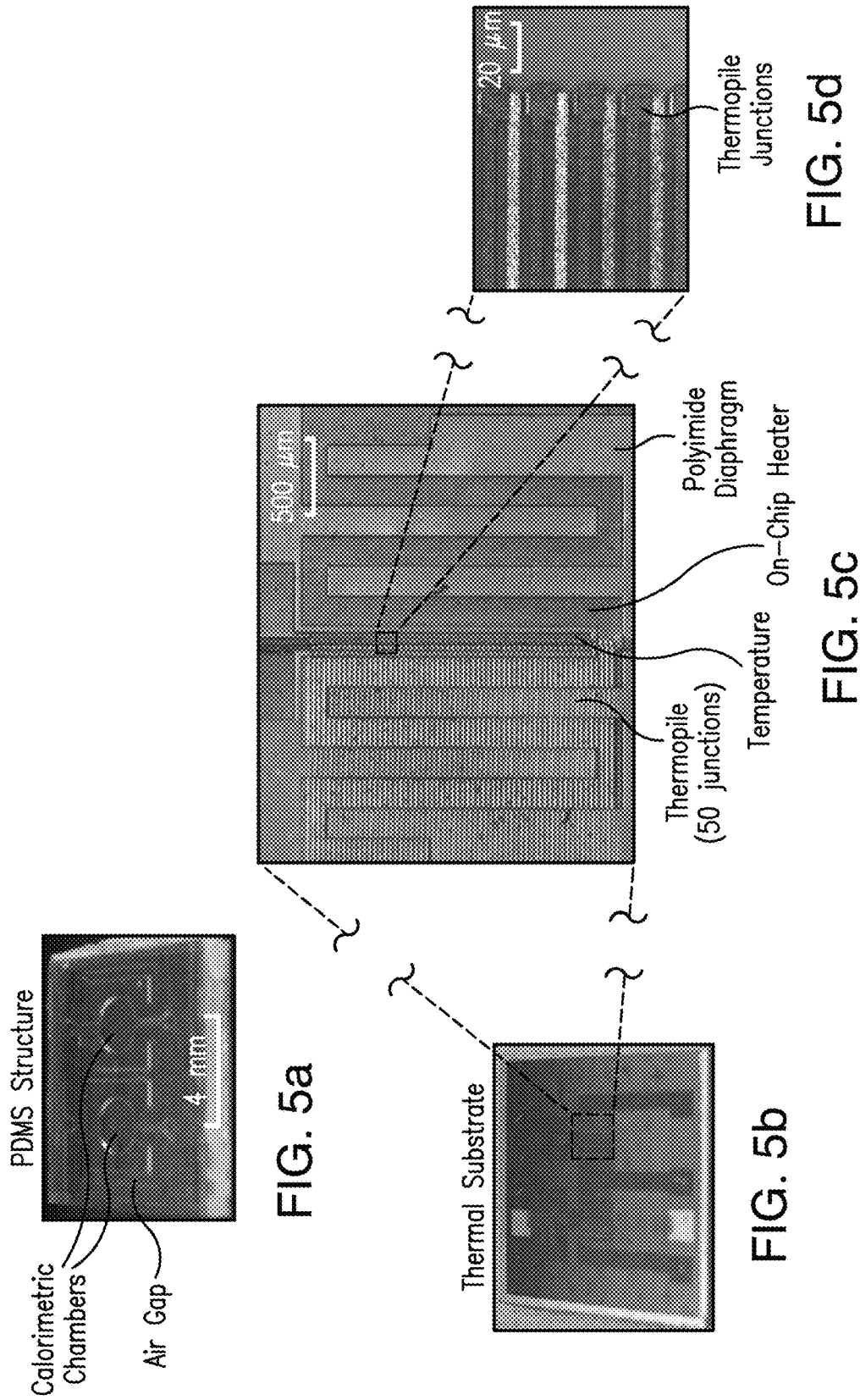

| | Temperature (°C) | Stoichiometry (N) | $K_B(M^{-1})$ | $\Delta H$ (kJ/mol) |
|---|---|---|---|---|
| Our results | 23 | 1.00 | ~$6.0\times10^3$ | 30.0 |
| | 35 | 1.05 | ~$2.8\times10^3$ | 27.8 |
| Published data* | 25 | 1.01 | $5.63\times10^3$ | 29.9 |
| | 40 | 0.97 | $3.17\times10^3$ | 29.4 |

*Data source: www.microcalorimetry.com

FIG. 33

|  | Temperature (°C) | Stoichiometry (n) | K (M$^{-1}$) | ΔH (kJ/mol) |
|---|---|---|---|---|
| Our results | 23 | 1.01 | ~9.0x10$^4$ | 52.3 |
|  | 35 | 1.07 | ~4.0x10$^4$ | 56 |
| Published data* | 28 | 1.00 | 8.27x10$^4$ | 51.4 |
|  | 38 | 1.04 | 4.85x10$^4$ | 57.5 |

FIG. 35

MEMS-BASED CALORIMETER, FABRICATION, AND USE THEREOF

CROSS REFERENCES TO RELATED APPLICATIONS

This application is a continuation-in-part of International Patent Application No. PCT/US2015/057384, filed Oct. 26, 2015, which claims priority from U.S. Provisional Application No. 62/068,562, filed Oct. 24, 2014, priority to both of which is claimed, and the disclosure of each of which is incorporated by reference herein in their entireties for all purposes.

STATEMENT REGARDING FEDERALLY FUNDED RESEARCH

This invention was made with government support under DBI-0650020 awarded by the National Science Foundation. The government has certain rights in this invention.

BACKGROUND

Differential scanning calorimetry (DSC) is a thermoanalytical technique that measures heat generated or required in thermally active processes as the temperature of a sample is varied. When applied to biochemical systems, DSC can provide a label-free method to determine the thermodynamic properties of a wide variety of biomolecular interactions and conformational transitions. DSC instruments, however, can be cumbersome and require large sample consumption, which has hindered the widespread application of DSC to biomolecular characterization.

Microelectromechanical Systems (MEMS) are small integrated devices or systems that combine electrical and mechanical components in very small mechanical devices. MEMS technology is based on fabrication technologies that can realize miniaturization, multiplicity, and microelectronics.

Some currently available MEMS calorimeters provide solid- or gas-phase or droplet-based detections. However, it can be difficult to properly handle liquid samples in a well-defined environment in the currently available MEMS calorimeters.

Flow-through and continuous-flow MEMS calorimeters integrate microfluidic chambers or channels as biological reactors. These devices can provide controlled fluidic environments and can allow easy integration with other microfluidic functionalities or thermal sensing configurations for biochemical thermodynamic investigations. However, these devices can still require a large amount of samples while being limited by significant convective heat leakage due to the continuous flow.

In addition, calibrating existing MEMS DSC devices can be complicated due to a lack of integrated heating elements and temperature sensing. Temperature-modulated calorimetry (AC calorimetry) involves calorimetric measurements under small temporally periodic temperature variations. Such temperature modulation can allow thermal relaxation of biomolecules, and thus AC calorimetry can detect biomolecular interactions under quasi-equilibrium conditions, and allow the biochemical reaction signal to be extracted at the modulation frequency in the face of broad-band background noise. However, suitable chips can involve thin solid films and operating parameters which are not practicable for biomolecular characterization in solution phase.

Isothermal titration calorimetry (ITC) can measure heat generated or required for a biochemical reaction as a function of the molar reactant ratio, and has been used in applications such as drug discovery and biotherapeutic development. However, conventional ITC instruments can have complicated structural designs, slow thermal response, and consume large amounts of sample and reagents.

SUMMARY

In accordance with one aspect of the disclosed subject matter, a microdevice is provided. The microdevice includes a reference channel including a first passive mixer, a sample channel including a second passive mixer, and a thermoelectric sensor located under each of the first and second passive mixers. The thermoelectric sensor can be configured to measure a temperature differential between the first and second passive mixers. In certain non-limiting embodiments, the microdevice further comprises a reaction chamber in addition to a sample channel and reference channel.

In an exemplary embodiment of the disclosed subject matter, the first and second passive mixers can be micromixers and/or splitting-and-recombination mixers. In accordance with certain embodiments, the first and second passive mixers can include a first set of one or more channels in a first horizontal plane and a second set of one or more channels in a second horizontal plane. For example, the first and second passive mixers can be formed by a top layer and a bottom layer, wherein the top layer includes a first set of channels and the bottom layer includes a second set of channels. The top layer and the bottom layer can be formed from a polymer material such as, e.g., US-8, parylene, polycarbonate, polyether ether ketone, or polydimethylsiloxane.

In accordance with some embodiments, the thermoelectric sensor can be a thermopile such as, for example, an antimony-bismuth thermopile. A substrate layer can be located beneath the thermopile. The substrate can be a polymeric and/or flexible layer such as Kapton film. The thermoelectric sensor can be coupled to the first and second passive mixers using oxygen plasma as a binder.

In other embodiments, a microdevice can include a first layer and a second layer. The first layer can include a reference channel including a first passive mixer, and a sample channel including a second passive mixer. The second layer is coupled to the first layer and can include a thermoelectric sensor located under each of the first and second passive mixers. The thermoelectric sensor can be configured to measure a temperature differential between the first and second passive mixers. The first and second mixers can be micromixers and/or splitting-and-recombination mixers.

In some embodiments, the first layer can include a first sublayer and a second sublayer. Each of the first and second passive mixers can include a first set of one or more channels in the first sublayer and a second set of one or more channels in the second sublayer. The first layer can be formed from a polymer such as, e.g., US-8, parylene, polycarbonate, polyether ether ketone, or polydimethylsiloxane.

In accordance with some embodiments, the thermoelectric sensor can be a thermopile such as, for example, an antimony-bismuth thermopile. A substrate layer can be located beneath the thermopile. The second layer can also include polymeric and/or flexible substrate such as Kapton film. The first layer can be coupled to the second layer using oxygen plasma as a binder.

In accordance with another aspect of the disclosed subject matter, a method of determining heat involved in a reaction between at least two substances is disclosed. A sample material and a second substance can be introduced into the sample channel, and the sample material and a buffer can be introduced into the reference channel. Each of the sample and reference channel can be connected to a sample chamber and a reference chamber, respectively. A thermal enclosure enclosing the microdevice is maintained at a constant temperature. A thermal property of the reaction between the sample material and the second substance can be determined based on the measured temperature differential between the sample channel and the reference channel. For example, the heat involved in the reaction between the sample material and the second substance at the given temperature can be determined based on the measured temperature differential between the sample channel and reference channel.

The reaction between the sample material and second substances can be a chemical reaction or a physical binding system, for example, ligand-protein binding. The thermal enclosure temperature can be varied such that the heat involved in the reaction can be determined at different temperature. Likewise, the concentration ratio between the two substances can also be varied such that reaction stoichiometry can be determined by the heat measured at different concentration ratios. The sample material, buffer, and second substance can be introduced into the respective channels through reference channel and/or sample channel inlets.

In an exemplary embodiment, a microelectromechanical systems-based calorimetric device for characterization of biomolecular interactions includes a first thermally-isolated micromixer, a second thermally-isolated micromixer, and a thermoelectric sensor. The thermoelectric sensor is configured to measure at least one temperature metric associated with first micromixer (the sample mixer) and the second micromixer (the reference mixer).

The first and second micromixers can be passive chaotic micromixers such as splitting-and-recombination micromixers. The device can further include a first inlet and a second inlet in fluid contact with the first micromixer, and a third inlet and a fourth inlet in fluid contact with the second micromixer. The sample channel and reference channel can be surrounded by an air cavity.

In accordance with an exemplary embodiment of the disclosed subject matter, the thermoelectric sensor can be a thermopile. The thermopile can be, for example, an antimony-bismuth thermopile. A first thermopile junction can be located on a first end of the sample channel, while a second thermopile junction can be located on the first end of the reference channel.

In accordance with an exemplary embodiment of the disclosed subject matter, titration on the MEMS device can be performed by merging a predetermined concentration of the sample material and a binding reagent into a reaction chamber. During the titration, the exact amount of the sample and/or the reagent can be delivered into the reaction chamber or reference chamber for heat measurement. In certain embodiments, the at least one temperature metric can be a differential temperature between the sample channel and the reference channel. In other embodiments, the at least one temperature metric can be a temperature of the reaction chamber and a temperature of the reference chamber.

The disclosed subject matter further provides microelectromechanical systems-based methods for characterization of a biomolecular interaction between a first solution and a second solution. In one example, a method includes mixing the first solution and the second solution to form a reaction solution, mixing the first solution and a buffer solution to form a reference solution, and measuring a differential temperature between a sample channel containing the reaction solution and a reference channel containing the reference solution. The differential temperature can be measured using a thermoelectric sensor such as a thermopile on the microelectromechanical systems-based device.

In accordance with an exemplary embodiment of the disclosed subject matter, micromixers on the microelectromechanical systems-based device (e.g., passive chaotic micromixers) can be used to mix the first and second solutions.

The method can further include computing a differential power based at least in part on the differential temperature. At least one thermodynamic reaction parameter can be calculated based at least in part on the differential power. The thermodynamic reaction parameter can be, for example, an equilibrium binding constant, a stoichiometry, or a molar enthalpy change.

A baseline temperature differential between the reaction chamber and the reference chamber can be measured prior to the introduction of the reaction solution and the reference solution. The baseline temperature differential can then be subtracted from the differential temperature for error correction. The device can also be calibrated using an on-chip heater.

The disclosed subject matter further provides microelectromechanical systems-based calorimetric devices for characterization of biomolecular reactions. In an exemplary embodiment, a device includes a thermally-isolated sample channel, a thermally-isolated reference channel, a thermally-isolated sample chamber, a thermally-isolated reference chamber and detection means for measuring a differential temperature between the reaction chamber and the reference chamber. The device can further include computing means for computing a differential power based at least in part on the differential temperature, and calculating means for calculating at least one thermodynamic reaction parameter based at least in part on the differential power.

In accordance with an exemplary embodiment of the disclosed subject matter, one or both reference and/or sample channels may be 3D diffusive and can be integrated with the thermopile by oxygen plasma.

BRIEF DESCRIPTION OF THE DRAWINGS

FIG. 5 Are images of a microdevice fabricated according to one embodiment of the disclosed subject matter: (a) the PDMS housing structure and air gap; (b) the solid substrate; (c) the thermopile, integrated microheater and temperature sensor embedded in the thin film substrate; and (d) the thermopile junctions.

FIG. 33 shows a comparison between reaction parameters obtained in accordance with an embodiment of the disclosed subject matter and published data reflecting reaction parameters obtained using commercial calorimeters.

FIG. 35 shows a second comparison between reaction parameters obtained in accordance with an embodiment of the disclosed subject matter and published data reflecting reaction parameters obtained using commercial calorimeters.

FIG. 48a is a graph showing the device steady-state response. FIG. 48b is a graph showing the device thermopile calibration. FIG. 48c is a graph showing the device time response when a constant power of 2.5 mW is applied.

FIG. 50a is a graph showing device output of the binding of 5 mM 18-C-6 and $BaCl_2$ at different molar ratios. FIG. 50b is a graph showing the calculated biochemical heat of the binding as well as a fitted curve to the one binding-site model.

FIG. 55a is a graph showing the baseline noises under different flow rates. FIG. 55b is a graph showing time-resolved device output upon introduction of sample compared with water baseline as the flow rate is chosen at 10 uL/min. FIG. 55c is a graph showing device voltage output of the 0.5 mM 18-C-6 reacting with $BaCl_2$ at different molar ratios. FIG. 55d is a graph showing non-linear curve fitting of the binding isotherm and the determination of the binding parameters.

DETAILED DESCRIPTION

In accordance with one aspect of the disclosed subject matter, a microdevice is provided. The microdevice includes a first thermally isolated microchamber, a second thermally isolated microchamber, and a thin film substrate. The first and second microchambers are also referred herein as the sample chamber and reference chamber, respectively. The sample and reference chambers can be identical in volume and configuration, and arranged side by side. In accordance with an exemplary embodiment of the disclosed subject matter, the sample and reference chambers can have a circular configuration. However, a wide variety of geometric configurations can be used in accordance with the disclosed subject matter. The sample and reference chambers can each be supported on the thin film substrate. The thin film substrate can include a thermoelectric sensor located under each of the sample and reference chambers and configured to measure the temperature differential between the sample and reference chambers.

Figure 1A:
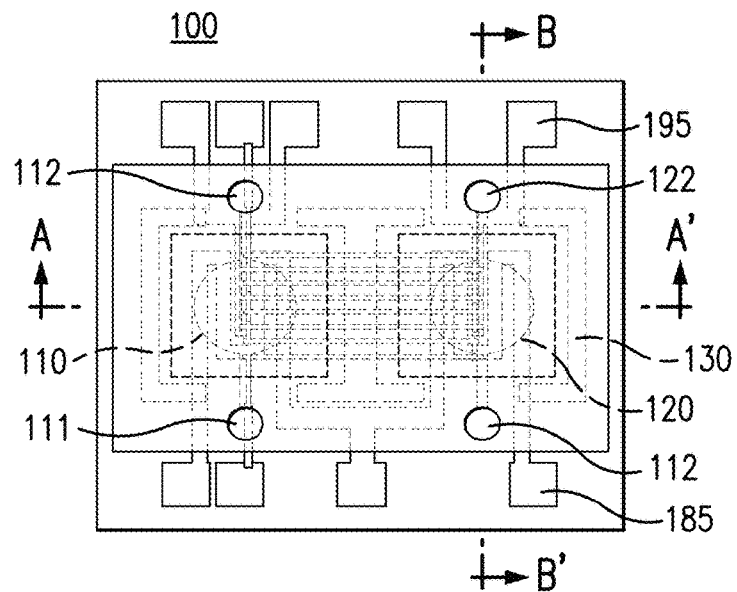
FIGS. 1a-1c depict a schematic of a microdevice according to some embodiments of the disclosed subject matter, in top (1a), isometric (1b), and sectional (1c) views.
Figure 1B:
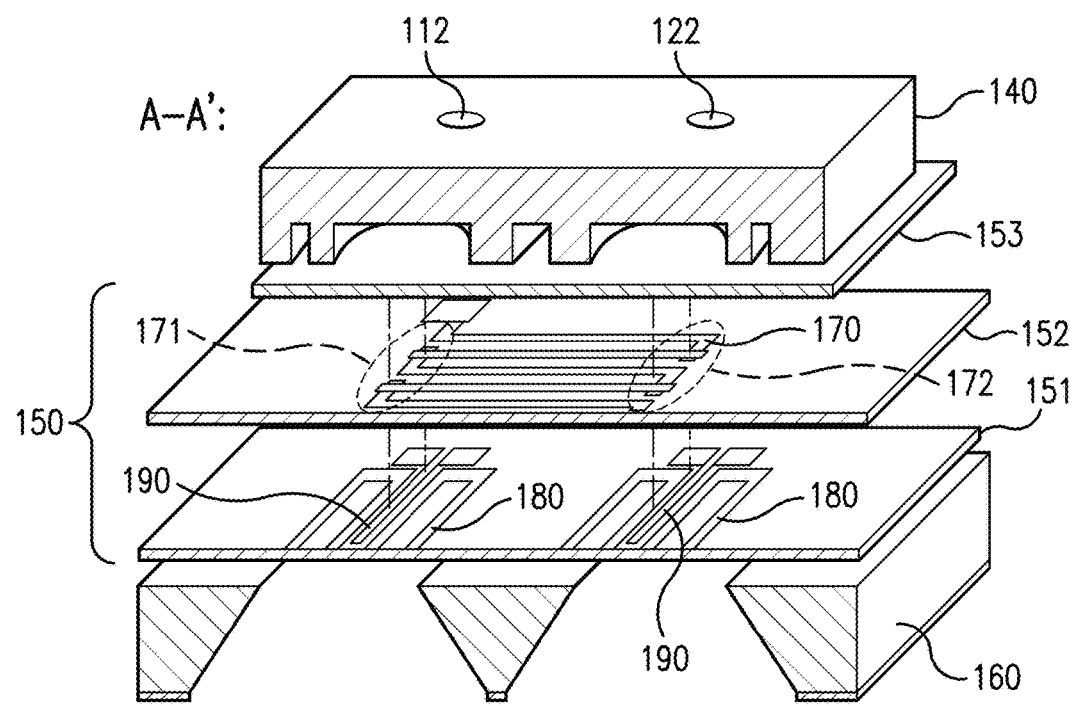
Figure 1C:
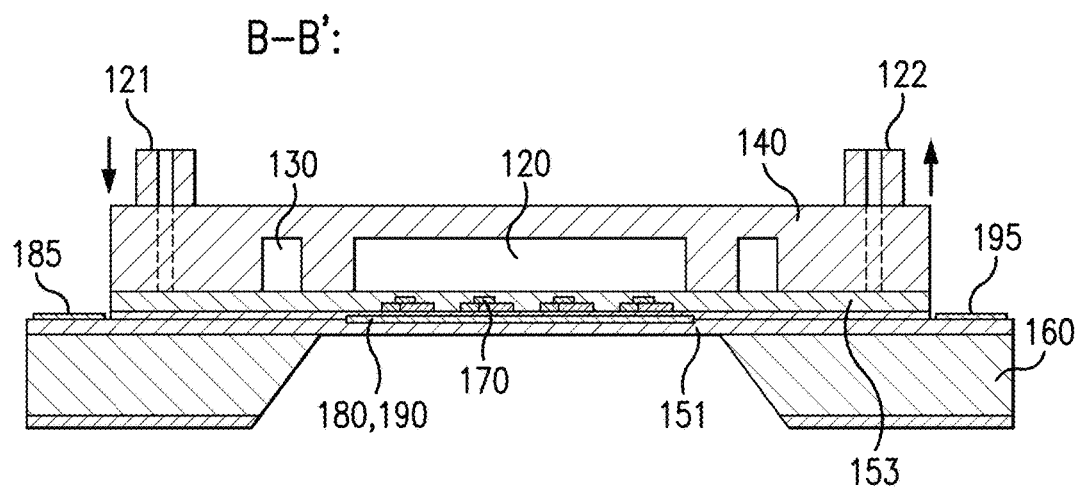

FIGS. 1a-1c depict an illustrative embodiment of the microdevice of the disclosed subject matter. The microdevice is also referred to as MEMS DSC device herein. The microdevice 100 includes two identical microchambers 110 and 120, which can hold sample and reference materials for calorimetric measurements. For easy reference, these microchambers are also referred to herein as the sample chamber and reference chamber, respectively, and collectively, "calorimetric chambers," or simply "chambers" Each of the sample and reference chambers is connected to an inlet port (111, 121) and an outlet port (112, 122) by microfluidic channels. The material for the housing of the chambers (140) can be made of any material suitable for microfabrication and thermal isolation. In certain embodiments, Polydimethylsiloxane (PDMS) is selected as the material to fabricate the calorimetric chambers for its ease of fabrication and packaging as well as biocompatibility. However, other materials suitable for microfabrication and thermal isolation can be used without departing from the scope of the disclosed subject matter. For example, a material having sufficient thermal stability within the temperature range of interest (e.g., −10° C. to 90° C.), reasonably strong bonding with the substrate surface, and minimized adsorption of macromolecules (e.g., proteins) can be used, The microchambers can be formed from polymers such as SU-8, parylene, polycarbonate, and polyether ether ketone (PEEK).

Each of the microchambers can be thermally isolated. For example, the air cavities (130) in FIG. 1a provide thermal isolation for the chambers. Air cavities can be formed from the same material used for fabrication of the microchambers. In accordance with an exemplary embodiment of the disclosed subject matter, the air cavities (130) can be formed from polydimethylsiloxane. However, other thermal isolation techniques can also be used as known in the art. For example, the microchambers can be thermally isolated by residing on a freestanding structure constructed from materials such as a polymeric material having low thermal conductivity. In order to further isolate the microchambers from the ambient environment, the microdevice 100 can be enclosed by a thermal enclosure (e.g., the microdevice 100 can be placed in a vacuum to minimize thermal energy dissipation to the ambient environment).

As shown in FIG. 1b, the microchambers (110, 120) are supported on a thin film substrate (150). The thin film substrate (150) along with air cavities (130) surrounding the chambers, provide thermal isolation that enables sensitive calorimetric measurements. The thin film (150) can include multiple polymeric layers or diaphragms (151, 152, 153). The layers 151, 152, 153 are integrated as shown in FIG. 1c, but for purpose of illustration, are shown in FIG. 1b as separate layers. Both of layers 151 and 152 can be made from a material have good thermal isolation property, as well as thermal and mechanical stability to withstand the thermal cycles required by repeated calorimetric measurements. In particular embodiments, the polymeric diaphragm can be made of a material having a glass transition temperature greater than 150° C. and thermal decomposition temperature greater than 250° C. For example, the material can be polyimide, parylene, polyester, SU-8, PDMS, and polytetrafluoroethylene, etc. The polymeric diaphragm can have a tensile strength of greater than 55 MPa, and/or Young's Modulus greater than 500 MPa. In particular embodiments, polyimide is selected as the diaphragm material because of to its excellent mechanical stiffness (Young's modulus: 2.5 GPa) and thermal stability (glass transition temperature: 285° C.).

To improve the adhesion between the housing material and the thin film substrate, an interfacing layer 153 can be made from a mixture of the material for layer 151 and/or 152, e.g., a mixture of polyimide/PDMS. The thin film substrate can be supported on another solid substrate (160), e.g., a silicon wafer. To improve thermal isolation, the solid substrate in the area underneath the bottom side of the thin film substrate corresponding to a cross section of each of the chambers can be removed, such that the portion of the thin film substrate under each of the chambers does not contact the solid substrate (i.e., it only contacts air, which is believed the best thermal insulator).

The microdevice can further include a thermoelectric sensor. A thermoelectric sensor can be coated on, embedded, or otherwise included in the thin film substrate and configured to measure the temperature differential between the two chambers. For example, a thin layer of thermopile (170) can be included between the polymeric layers (152, 153). As illustrated in FIGS. 1b and 1c, the thermopile can include a plurality of elongated segments of dissimilar materials, where adjacent segments of dissimilar materials are joined together at opposite ends, thereby forming thermocouple junctions (171 and 172). The thermocouple junctions underneath each chamber can be aligned to the central axis of each chamber. The material for the thermopile can include a variety of dissimilar pairs of metals, e.g., antimony-bismuth (Sb—Bi), or other pairs of materials providing high thermoelectric efficiency, such as n-type and p-type bismuth telluride, and n-type and p-type antimony telluride. For example, the thermoelectric sensor can have a thermoelectric sensitivity of greater than 80 µV/° C. per thermocouple. In particular embodiments, antimony (Seebeck coefficient: 43 µV/K) and bismuth (Seebeck coefficient: −79 µV/K) are selected for the thermopile material due to their high thermoelectric sensitivities and ease of fabrication. A wide variety of metals, semiconductors, and their compounds, including chrome, nickel, bismuth, antimony, bismuth telluride, and antimony telluride, can be used in fabricating the thermopile.

In accordance with another embodiment of the disclosed subject matter, the thermoelectric sensor can include a sample chamber thermoelectric sensor and a reference chamber thermoelectric sensor, each of which measures the absolute temperature of the reaction in the respective microchambers. The differential temperature can then be determined by calculating the different between the temperatures measured by the thermoelectric sensors. The thin film substrate can further include two sets of microheaters (180) and temperature sensors (190) which are aligned underneath the two chambers (110, 120), respectively. For example, the microdevice 100 can include an integrated tin-film resistive micro-temperature sensor and heater. The temperature sensors (190) can monitor the chamber temperatures in real time, and the microheaters (180) can provide heating to the chambers to generate a constant differential power for calorimetric calibration. For purposes of calibration, Joule heating can be generated by passing an electrical current through the microheater. The local temperature can then be determined by the temperature sensor based on a calibrated relationship between the temperature and the electrical resistance.

Both of the microheaters (180) and temperature sensors (190) can be embedded in the thin film, but vertically away and insulated from the thermopile (170). For example, the microheaters (180) and temperature sensors (190) can be embedded between layers 151 and 152. The contact pad (195) for the temperature sensor and the contact pad for the microheaters (185) can extend outside of the chamber housing structure for external electrical connection. Although shown in FIGS. 1b and 1c as situated on the same layer, the microheaters (180) and the temperature sensors (190) can also be situated on different layers. For precise temperature sensing, particularly in device calibration, the thermopile junctions (171, 172) can be aligned with the temperature sensors (190). The microheaters (180) can be patterned in a way to provide uniform heating of the chambers, for example, in a meandering pattern underneath the bottom area of the chambers. The material of the microheaters can be chosen from a variety of metals or metal alloys, for example, chromium/gold (Cr/Au).

Figure 2A:
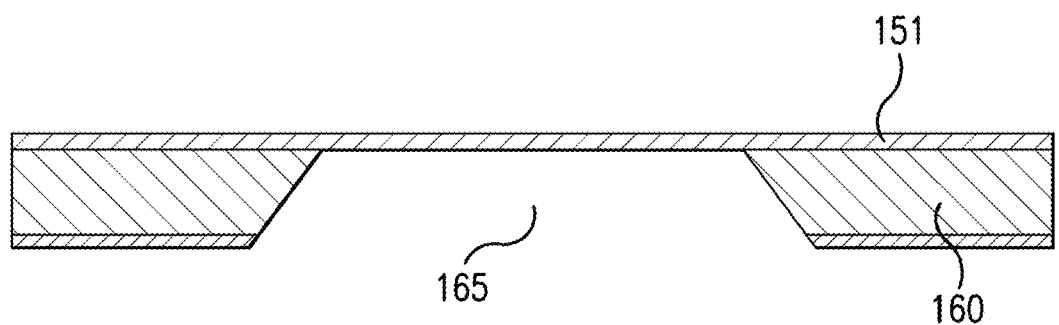
FIGS. 2a-2e depict a procedure for the fabrication of the microdevice according to some embodiments of the disclosed subject matter.

In one embodiment, the microdevice illustrated in FIGS. 1a-c can be fabricated by a procedure as outlined below. A solid substrate (160), such as silicon wafer, is provided. In accordance with other embodiments, a polymeric layer can be used as a substrate rather than a silicon layer. The polymeric layer can be a flexible layer. The flexible layer can be, for example, a layer of Kapton film A polymeric diaphragm (151), e.g., a polyimide film, can be coated on the substrate, e.g., by spin-coating (FIG. 2a). A pair of cavities (165) can be etched using, for example, tetramethylammonium hydroxide (TMAH) into the backside of the substrate in the areas that correspond to the calorimetric chambers.

Figure 2B:
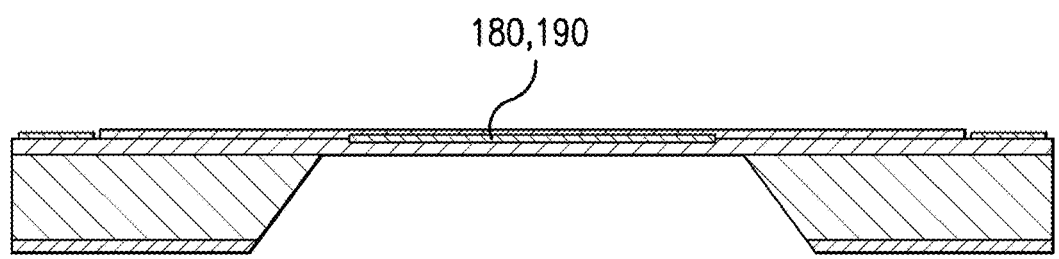
Figure 2C:
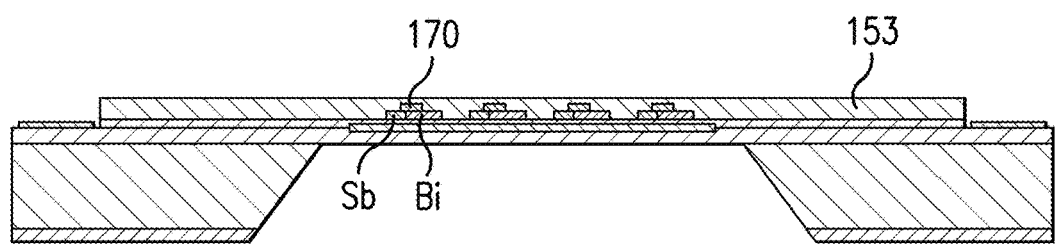
Figure 2D:
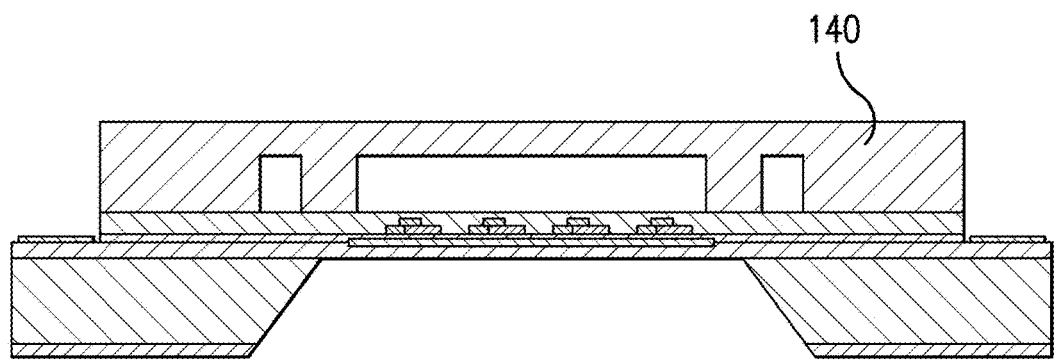
Figure 2E:
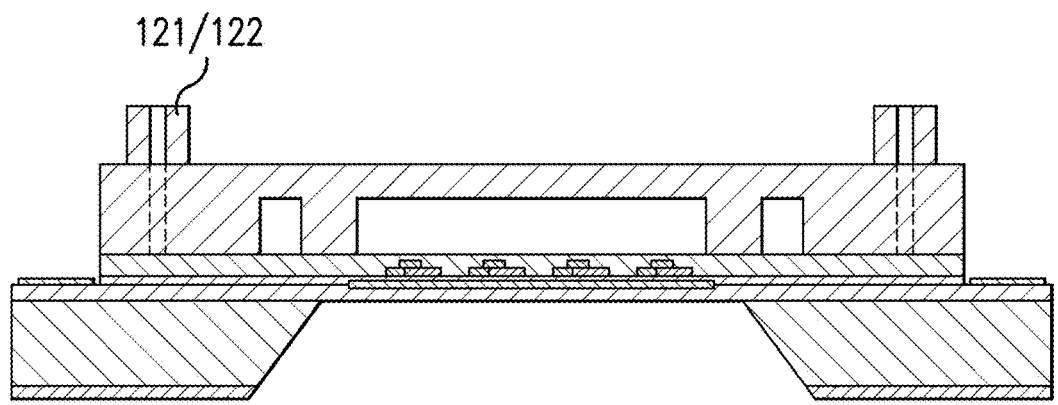

After the curing of the polymeric diaphragm, microheaters (180) and temperature sensors (190) can be deposited by thermal evaporation of a metal or metal alloy, e.g., Cr/Au. This is followed by coating another polymeric diaphragm (152) on top of the microheaters and temperature sensors (FIG. 2*b*). Subsequently, the thermoelectric sensor (170), e.g., a thermopile, can be thermally evaporated and patterned using a standard lift-off process, and the thermoelectric sensor is further coated by another polymeric layer (153), e.g., a layer containing polyimide-PDMS mixture (FIG. 2*c*). The chamber housing structure (140) can then be fabricated, e.g., from PDMS using micromolding techniques on top of the thin film substrate, thereby forming the calorimetric chambers (FIG. 2*d*). Microfluidic structure such as microchannels connecting the chambers to the inlet and outlet ports (121/122) can also be fabricated (FIG. 2*e*). The residual silicon layer on the backside of the thin film can then be removed (FIG. 2*e*), thereby forming the freestanding thin film substrate portions under each of the chambers.

Figure 27:
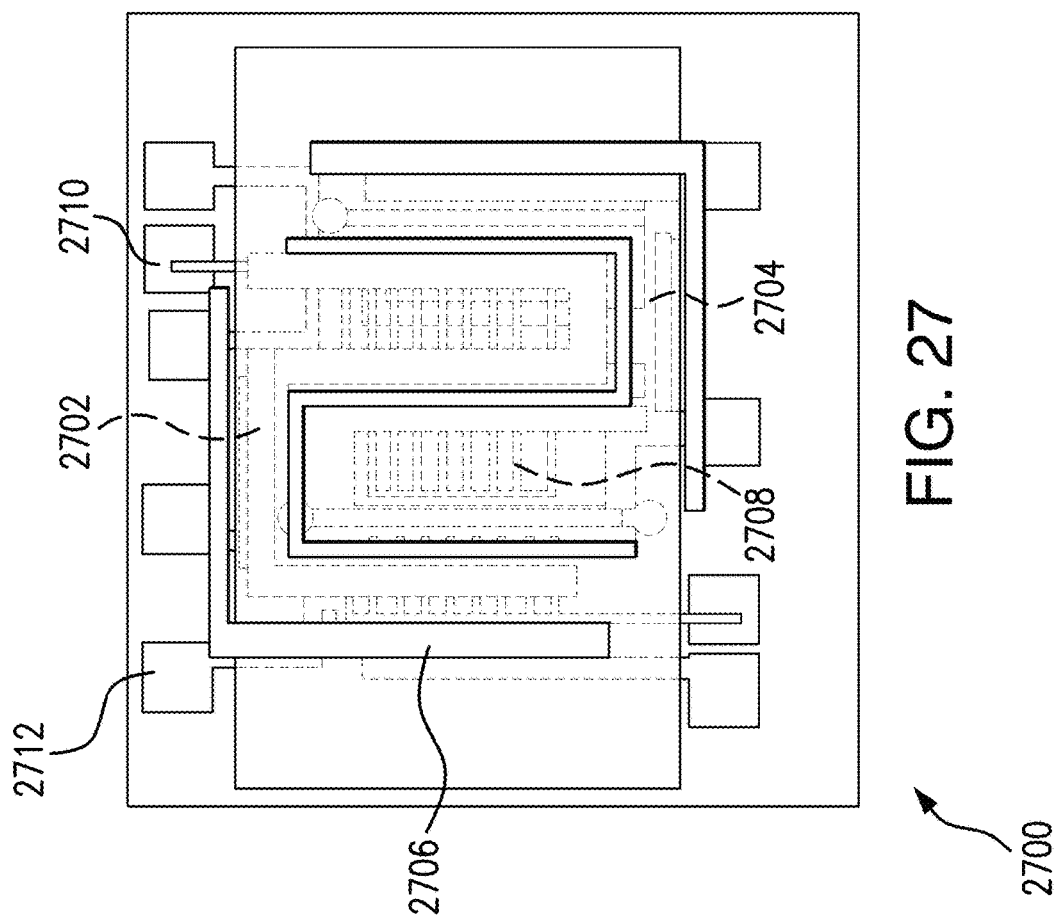
FIG. 27 depicts a top view of a schematic of a microdevice in accordance with an exemplary embodiment of the disclosed subject matter.

With reference to FIG. 27, a second embodiment of the microdevice in accordance with the disclosed subject matter is shown. The device 2700 includes a serpentine reference chamber (2702) and a serpentine sample chamber (2704). The reference chamber (2702) and sample chamber (2704) are thermally isolated by air cavities (2706). The microdevice 2700 also include a thermopile (2708). The use of serpentine microchambers (2702, 2704) can allow for a greater number of thermopile junctions can improve thermal isolation.

The microdevice 2700 also includes one or more contact pads (2710, 2712). The contact pads can provide an interface between the device and various electronic circuits. For example, contact pad 2710 can be coupled to the thermopile (2708). The adhesion between the ends of the thermopile (2708) and contact pad 2710 can be enhanced by surface roughening or chemical modification. A designed external packaging via a flip chip bonding method can also be implemented. The output of the thermopile (2708) is a voltage indicative of a differential temperature between the reference chamber (2702) and the sample chamber (2704). The contact pad 2710 can also be coupled to an electronic circuit for measuring and analyzing the output voltage. The term "coupled," as used herein, includes direct coupling such as direct electrical contact (e.g., through a soldered wire or alligator clip) as well as indirect coupling, as through wireless communication.

Figure 28:
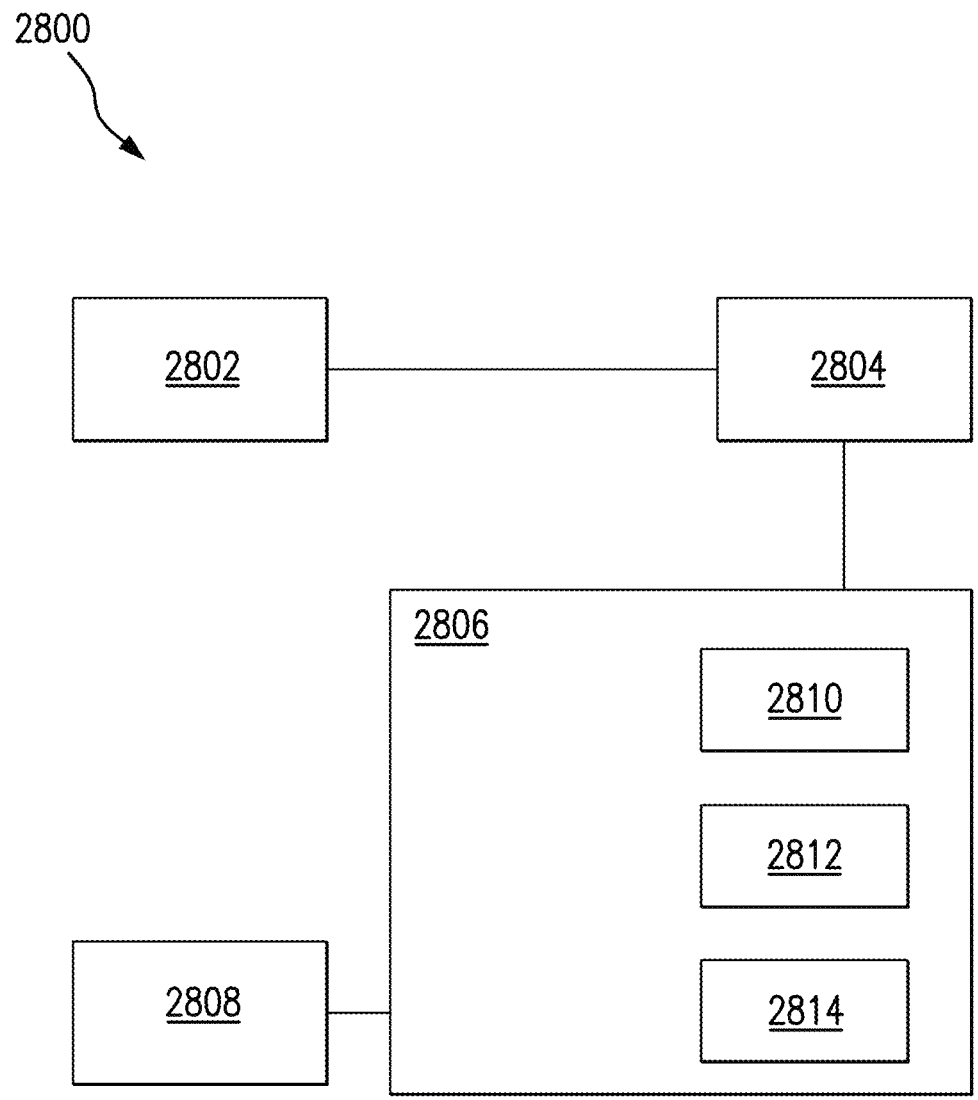
FIG. 28 is a diagram illustrating an electronic circuit that can be coupled to a microdevice in accordance with an exemplary embodiment of the disclosed subject matter.

An exemplary embodiment of an electronic circuit that can be coupled to contact pad 2710 in accordance with the disclosed subject matter is illustrated in FIG. 28. The contact pad (2802) acts as the interface between the microdevice and the one or more electronic circuits 2800. The contact pad can be coupled to a voltmeter (2804). The term "voltmeter," as used herein, is intended to encompass any instrument tat can be used to measure voltage, either directly or indirectly, including voltmeters and multimeters. The voltmeter (2804) can include at least one processor.

The voltmeter (2804) can be coupled to a calculation device (2806). The calculation device (2806) includes one or more processors formed by one or more electronic circuits. The calculation device (2806) can be coupled to a storage device (2808).

The calculation device (2806), as well as each of the components thereof, can be implemented in a variety of ways as known in the art. For example, each of the components of the calculation device can be implemented using a single integrated processor. In another embodiment, each component can be implemented on a separate processor. One or more components of the calculation device (2806) can be combined with the voltmeter (2804) rather than being a separate device.

The at least one processor can include one or more electronic circuits. The one or more electronic circuits can be designed so as to implement the disclosed subject matter using hardware only. Alternatively, the processor can be designed to carry out instructions specified by computer code stored in the storage device (2808). The storage device can be a hard drive, a removable storage medium, or any other non-transitory storage media. Such non-transitory storage media can store instructions that, upon execution, cause the at least one processor to perform the methods disclosed herein.

The calculation device (2806) can include a number of components, including an adjustment component (2810) for adjusting the output voltage based on a baseline in output voltage, a thermal power differential component (2812) for determining a thermal power differential based on the output voltage, and a reaction characterization component (2814) for calculating thermodynamic reaction parameters based on the thermal power differential.

With further reference to FIG. 27, contact pad 2712 can be coupled to a microheater and/or a temperature sensor. Contact pad 2712 can further be coupled to one or more electronic circuit for implementing the in-situ temperature monitoring and on-chip device calibration methods as disclosed herein.

Figure 36:
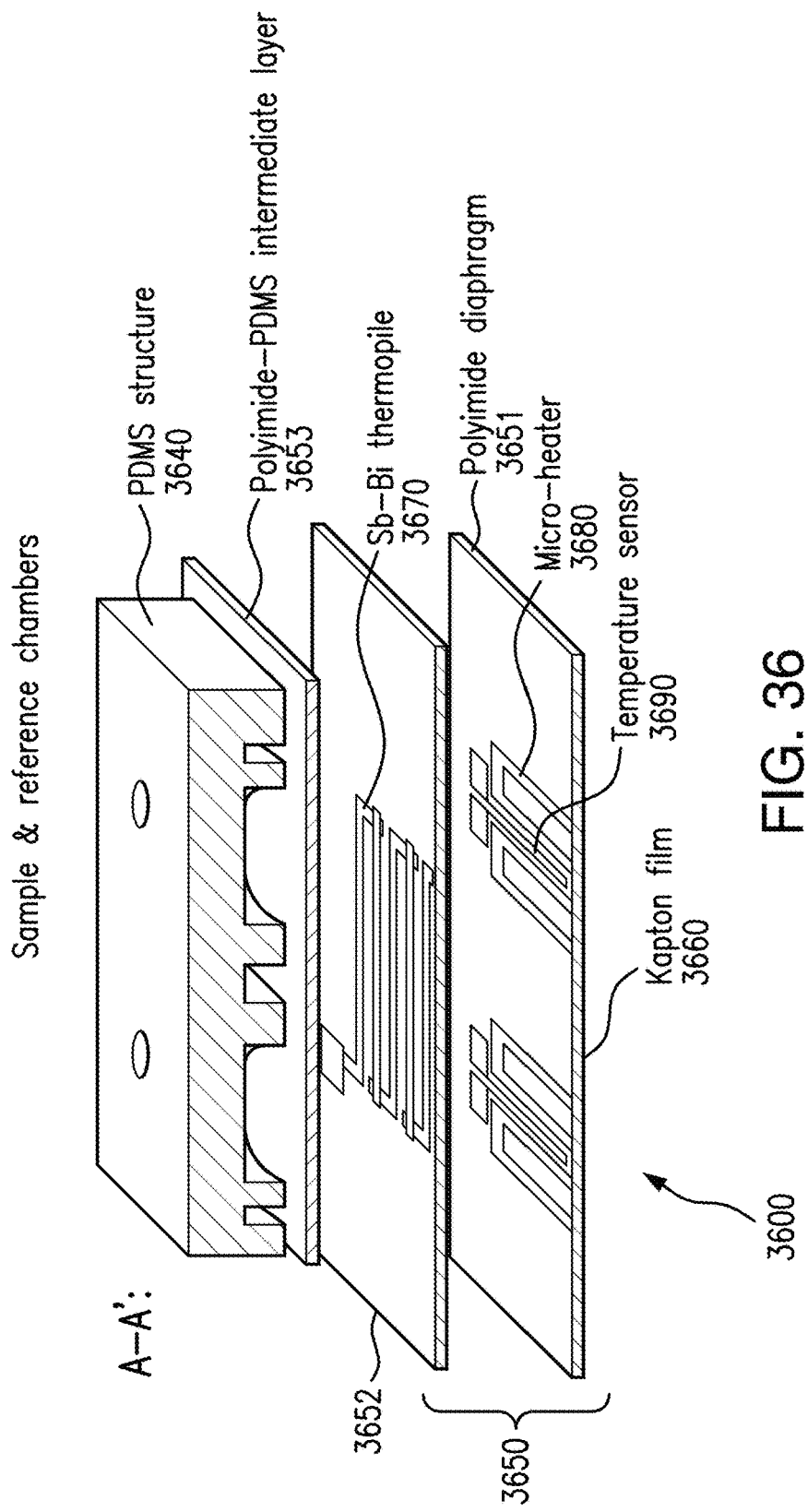
FIG. 36 depicts an isometric view of a schematic of a microdevice in accordance with an exemplary embodiment of the disclosed subject matter.

With reference to FIG. 36, a third embodiment of a microdevice in accordance with the disclosed subject matter is shown. The device 3600 includes a structure 3640 that forms microchambers. The microchambers can be, for example, circular or serpentine in shape. Structure 3640 can be a structure made of PDMS or another polymer, and can be supported by a thin film substrate 3650. Thin film substrate 3650 can include polymeric layers 3651, 3652, and 3653. Polymeric layer 3652 can include a thermopile 3670. The thermopile 3670 can include Sb—Bi or other thermoelectric junctions. Likewise, polymeric layer 3651 can include micro-heaters 3680 and temperature sensors 3690.

The thin film substrate 3650 can be formed on a substrate 3660. In accordance with embodiment of the disclosed subject matter, the substrate can be a flexible material. For example, the flexible material can have a flexural modulus of at least about 1.0, at least about 1.2, at least about 1.4, at least about 1.6, at least about 1.8, or at least about 2.0.

In accordance with another embodiment, the substrate 3660 can be formed by a polymeric material. Polymeric materials suitable for use as a substrate include, but are not limited to, polyimide, parylene, polyester, and polytetrafluoroethylene. The material can have a tensile strength and Young's modulus sufficient for the structural integrity, as well as having a glass transition temperature above the temperature range for the desired measurements. The thickness of the polymeric substrate can be between about 5 µm and about 1000 µm, or between about 10 µm and about 500 µm. For example, in accordance with embodiments of the disclosed subject matter, the thickness of the flexible substrate can be about 10 µm, about 20 µm, about 30 µm, about 40 µm, about 50 µm, about 50 µm, about 75 µm, about 100 µm, about 150 µm, about 200 µm, about 250 µm, about 300 µm, about 350 µm, about 400 µm, about 450 µm, or about 500 µm.

Microdevices formed on flexible layers such as polymeric layers can improve robustness and fabrication yield due to low intrinsic stress of the polymer as compared to more fragile substrates such as a silicon substrate. In addition, the low thermal conductivity of the polymer substrate can lead to enhanced thermal isolation of measurement samples for improved sensitivity. In addition, because the polymer substrate can be flexible, deformation of the substrate can be permitted, which can allow the device to conform to non-planar surfaces. As such, the device can be used in applications that involve geometry with curvature. Devices with polymeric substrates can also be low cost and disposable, which can eliminate cross-contamination between samples.

Figure 37A:
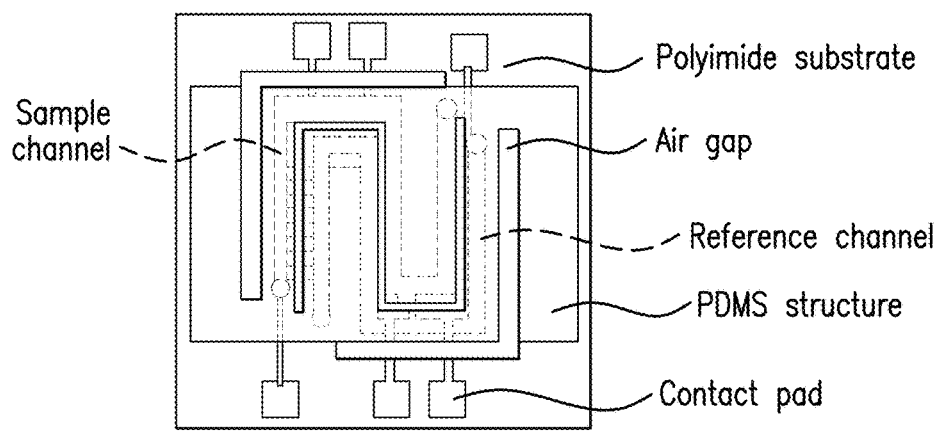
FIG. 37 depicts top and isometric views of a schematic of a microdevice in accordance with an exemplary embodiment of the disclosed subject matter.
Figure 37B:
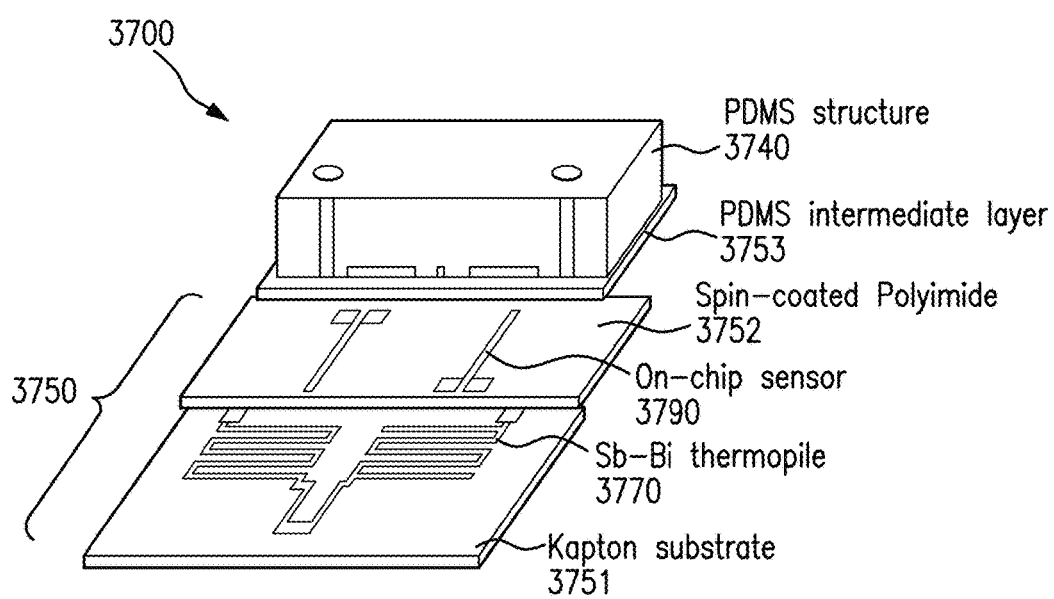

With reference to FIG. 37, a fourth embodiment of a microdevice in accordance with the disclosed subject matter is shown. The device 3700 includes a structure 3740 that forms microchambers. The microchambers can be, for example, circular or serpentine in shape. Structure 3740 can be a structure made of PDMS or another polymer, and can be supported by a thin film substrate 3750. Thin film substrate 3750 can include layer 3751 and polymeric layers 3752, and 3753. Polymeric layer 3752 can include a microheaters (not shown) and temperature sensors 3790. Likewise, layer 3751 can include thermopile 3770. The thermopile 3770 can include Sb—Bi or other thermoelectric junctions. Layer 3751 can be a flexible layer and/or a polymeric layer. The polymeric layer can be constructed using the same materials and dimensions as the polymeric layer 3660 described above.

With reference to FIG. 38, in one embodiment, the microdevice illustrated in FIG. 37 can be fabricated by a procedure as outlined below. In FIG. 38(a), a layer 3802 can be reversibly bound to silicon wafer 3804. While the FIG. 38 will be described with reference to a flexible layer, it will be understood that a polymeric layer can also be used in accordance with the disclosed subject matter. The flexible layer 3802 can be, for example, a polymeric layer such as a polyimide film (e.g., a Kapton film). The flexible layer can have a thickness of about 12.5 µm. The flexible layer 3802 can be reversibly bound to the silicon wafer 3804 by an adhesive layer 3806 such as a spin-coated PDMS layer. The adhesive layer can have a thickness of about 20 µm. The adhesive layer can then be cured.

Figure 38A:
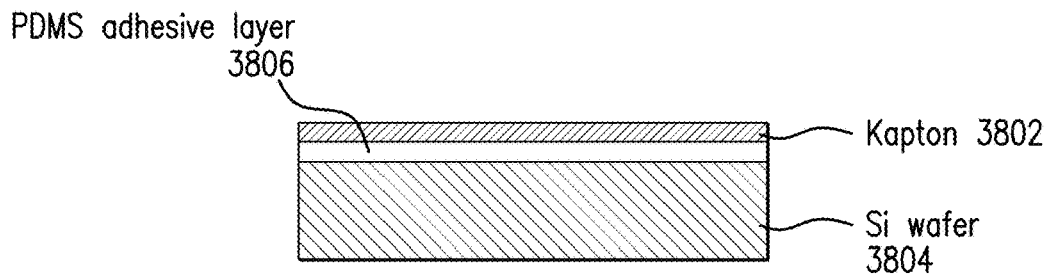
FIG. 38 depicts a process for fabricating a microdevice in accordance with an exemplary embodiment of the disclosed subject matter.
Figure 38B:
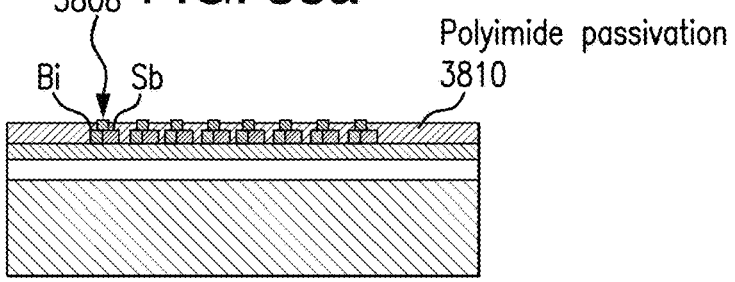

In FIG. 38(b), a thermopile can be formed on the flexible layer 3802. For example, Sb and Bi can be thermally evaporated and patterned on the substrate using a standard lift-off process to form a 400-junction thermopile 3808. In accordance with one embodiment, the antimony can have a thickness of about 0.8 µm and the bismuth can have a thickness of about 1 µm. The thermopile can then be passivated with a spin-coated polyimide thin layer 3810. The thin layer 3810 can have a thickness of about 1.5 µm.

Figure 38C:
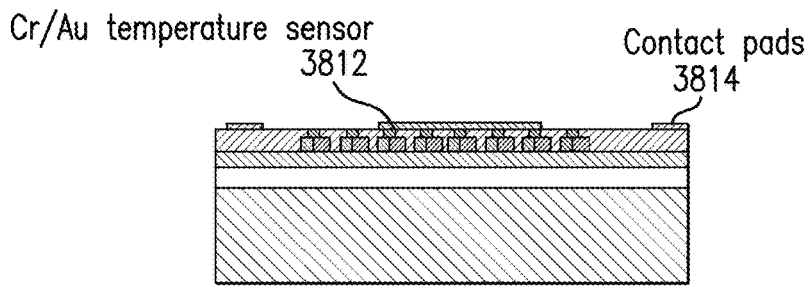

In FIG. 38(c), temperature sensors 3812 can be formed on the thin layer 3810. For example, a chromium/gold tin film can be deposited and patterned to form an on-chip temperature sensor 3812. The chromium/gold thin film can have a thickness of about 100 µm. Contact pads 3814 can be formed in a similar manner.

Figure 38D:
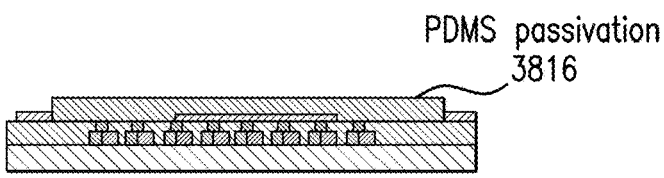

In FIG. 38(d), the device can be separated from the silicon wafer 3804. In accordance with some embodiments, the device can first be passivated with another thin layer 3816 such as a thin PDMS layer. The device can then be mechanically released from the silicon wafer 3804. The adhesive layer 3806 can also be removed during this process. In accordance with some embodiments of the disclosed subject matter, the silicon wafer can be reused for manufacture of subsequent microdevices.

Figure 38E:
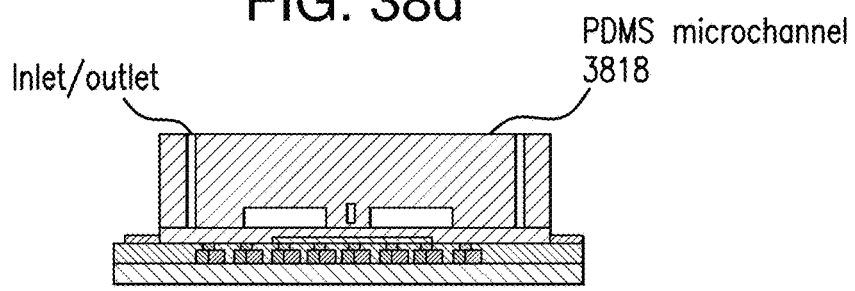

In FIG. 38(e), microchambers can be formed. The formation of microchambers can be performed in parallel with the removal of the silicon wafer 3804. In accordance with one embodiment of the disclosed subject matter, serpentine microfluidic channels can be formed in a polymeric layer 3818 (such as a PDMS layer) via soft lithography. The polymeric layer 3818 can be bonded to the microfluidic structure using, for example, oxygen plasma.

Figure 44:
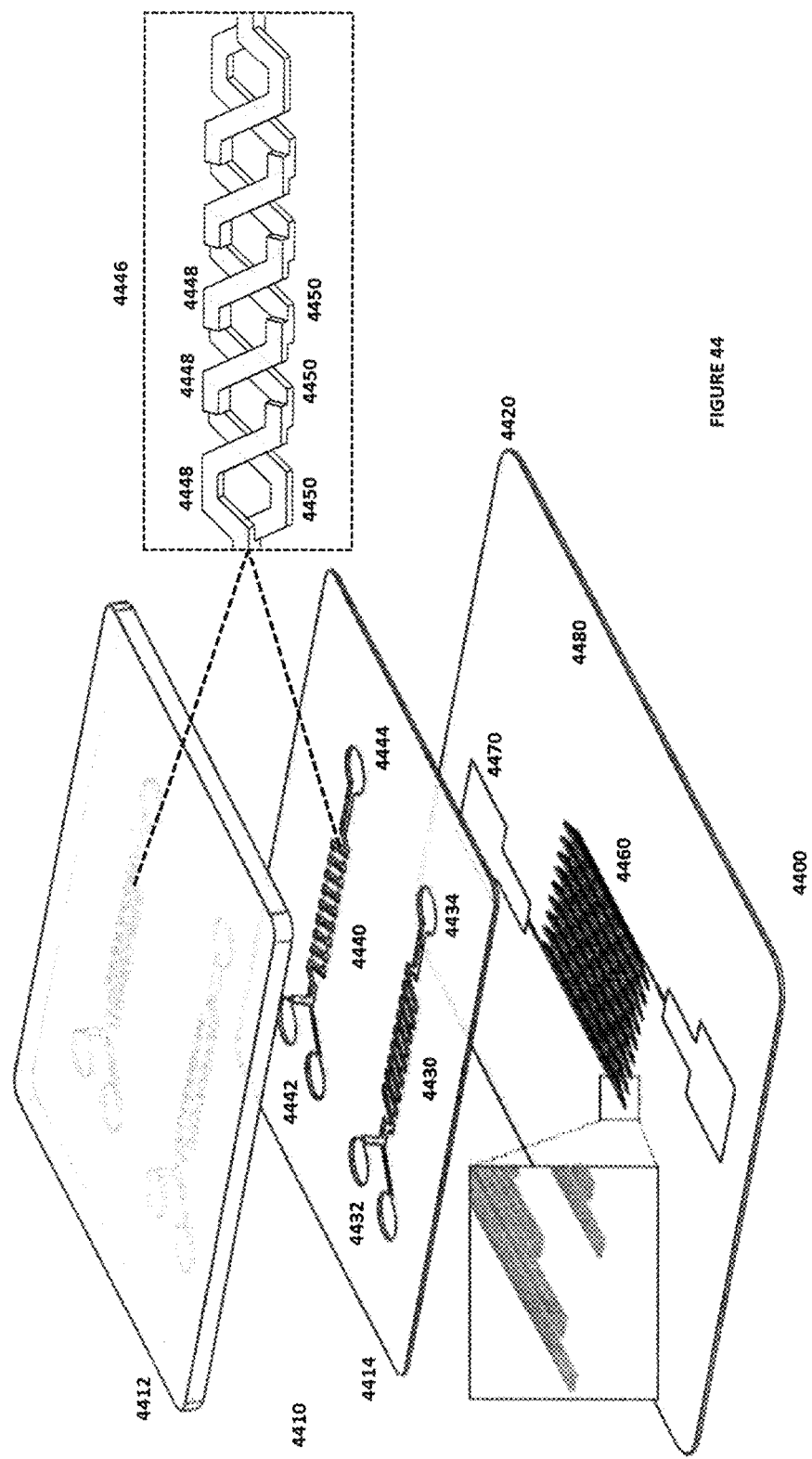
FIG. 44 depicts a schematic of a microdevice in accordance with an exemplary embodiment of the disclosed subject matter.

With reference to FIG. 44, a fifth embodiment of a microdevice in accordance with the disclosed subject matter is shown. The device 4400 includes a first layer 4410 and a second layer 4420. The first layer 4410 can be a polymeric structure. For example, first layer 4410 can be a structure formed from PDMS or another polymer. First layer 4410 can include a first sublayer 4412 and a second sublayer 4414.

The first layer includes reference channel 4430 and sample channel 4440. In accordance with an exemplary embodiment of the disclosed subject matter, reference channel 4430 can include reference channel inlets 4432 and a reference channel outlet 4434. Similarly, sample channel 4440 can include sample channel inlets 4442 and sample channel outlet 4444.

Sample channel 4440 can include a passive mixer 4446. The passive mixer can be, for example, a splitting-and-recombination micromixer. As shown in FIG. 44, the passive mixer 4446 can include a first set of channels 4448 formed in the first sublayer 4412, and a second set of channels formed 4450 formed in the second sublayer 4414. The first set of channels 4448 are located in a first horizontal plane, and the second set of channels 4550 are located in the second horizontal plane.

The second layer 4420 of device 4400 can include a thermoelectric sensor 4460. The thermoelectric sensor 4460 can be, for example, a thermopile such as an antimony-bismuth thermopile. The thermoelectric sensor can be coupled to one or more contact pads 4470. The contact pads 4470 can be, for example, gold contact pads. The second layer 4420 of device 4400 can also include a substrate 4480. The substrate can be, for example, a silicon substrate. In accordance with other embodiments of the disclosed subject matter, the substrate can be a flexible substrate such as, for example, a Kapton film substrate.

Notably, the microdevice shown in FIG. 44 does not include separate reference or sample microchambers. Movement of the materials from the mixers into a separate microchamber can result in heat loss. The design demonstrated in FIG. 44 can reduce this heat loss and therefore improve the measurement accuracy. In addition, such a design can reduce the amount of material needed for the reactions and can decrease the footprint of the device. For example, calorimetric measurements can be performed using about 50 ng of reaction material in a total reaction volume of about 450 nL.

Figure 45:
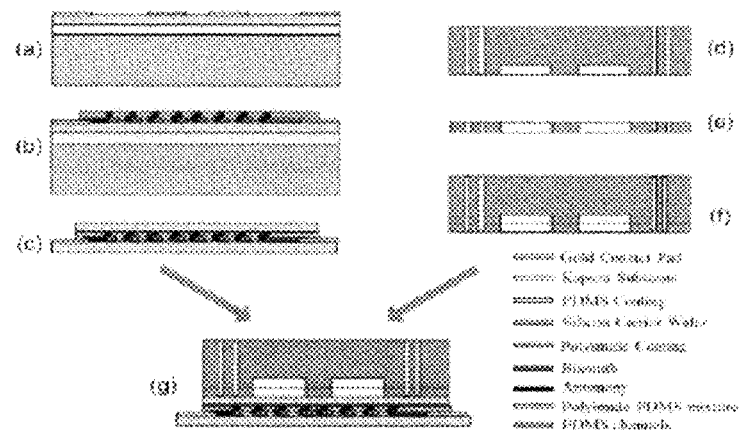
FIG. 45 depicts a process for fabricating a microdevice in accordance with an exemplary embodiment of the disclosed subject matter.

With reference to FIG. 45, in one embodiment, the microdevice illustrated in FIG. 44 can be fabricated by a procedure as outlined below. In FIG. 45(a), a layer 4502 can be reversibly bound to silicon wafer 4504. While the FIG. 45 will be described with reference to a flexible layer, it will be understood that a polymeric layer can also be used in accordance with the disclosed subject matter. The flexible layer 4502 can be, for example, a polymeric layer such as a polyimide film (e.g., a Kapton film). The flexible layer can have a thickness of about 12.5 µm. The flexible layer 4502 can be reversibly bound to the silicon wafer 4504 by an adhesive layer 4506 such as a spin-coated PDMS layer. The adhesive layer can have a thickness of about 20 µm. The adhesive layer can then be cured. Contact pads 4508 can also be formed on the layer 4502.

In FIG. 45(b), a thermopile can be formed on the flexible layer 4502. For example, Sb and Bi can be thermally evaporated and patterned on the substrate using a standard lift-off process to form a 400-junction thermopile 4510. In accordance with one embodiment, the antimony can have a thickness of about 0.8 µm and the bismuth can have a thickness of about 1 µm. The thermopile can then be passivated with a spin-coated polyimide thin layer 3810. The thin layer 3810 can have a thickness of about 1.5 µm.

In FIG. 45(*c*), the device can be separated from the silicon wafer 4504. In accordance with some embodiments, the device can first be passivated with another thin layer 4512 such as a thin PDMS layer. The device can then be mechanically released from the silicon wafer 4504. The adhesive layer 4506 can also be removed during this process. In accordance with some embodiments of the disclosed subject matter, the silicon wafer can be reused for manufacture of subsequent microdevices.

In FIGS. 45(*d*) and 45(*e*), micromixers can be formed in top layer 4514 and bottom layer 4516. The micromixers can be formed using soft lithography or other techniques known in the art. The formation of micromixers can be performed in parallel with the steps shown in FIGS. 45(*a*) through 45(*c*). In accordance with one embodiment of the disclosed subject matter, components of splitting-and-recombination micromixers can be formed in top layer 4514 and bottom layer 4516 via soft lithography.

In FIG. 45(*f*), the top layer 4514 and bottom layer 4516 can be bonded together. Bonding can be accomplished using, for example, oxygen plasma. The channels can be precisely aligned using, for example, an optical microscope.

In FIG. 45(*g*), the thermopile layer from FIG. 45(*c*) can be bonded to the micromixer layer from FIG. 45(*f*) using, for example, oxygen plasma, to form the microdevice 4518. In accordance with another aspect of the disclosed subject matter, a method of determining a thermal property of an analyte is provided. The method includes providing a microdevice as described above, providing a thermal enclosure enclosing the microdevice; loading a sample material containing an analyte into the first microchamber; loading a reference material into the second microchamber, the reference material does not contain the analyte; heating the thermal enclosure at a predetermined temperature scanning rate; and determining a thermal property of the analyte based on the measured temperature differential between the first microchamber and the second microchamber. The microdevice and the method of using the microdevice for calorimetric measurement are further described in conjunction with each other in the Examples below. It is appreciated that the microdevice including any of the specific features described below can be used in the method of using the microdevice, and vice versa.

While the method of determining a thermal property of an analyte is generally described with reference to measuring a temperature differential within the microchambers, a person skilled in the art will understand that in other embodiments the microchambers should not be used. For example, when using the method in connection with the device described in FIG. 44, the temperature differential between the reference channel and the sample channel is used instead.

Figure 3:
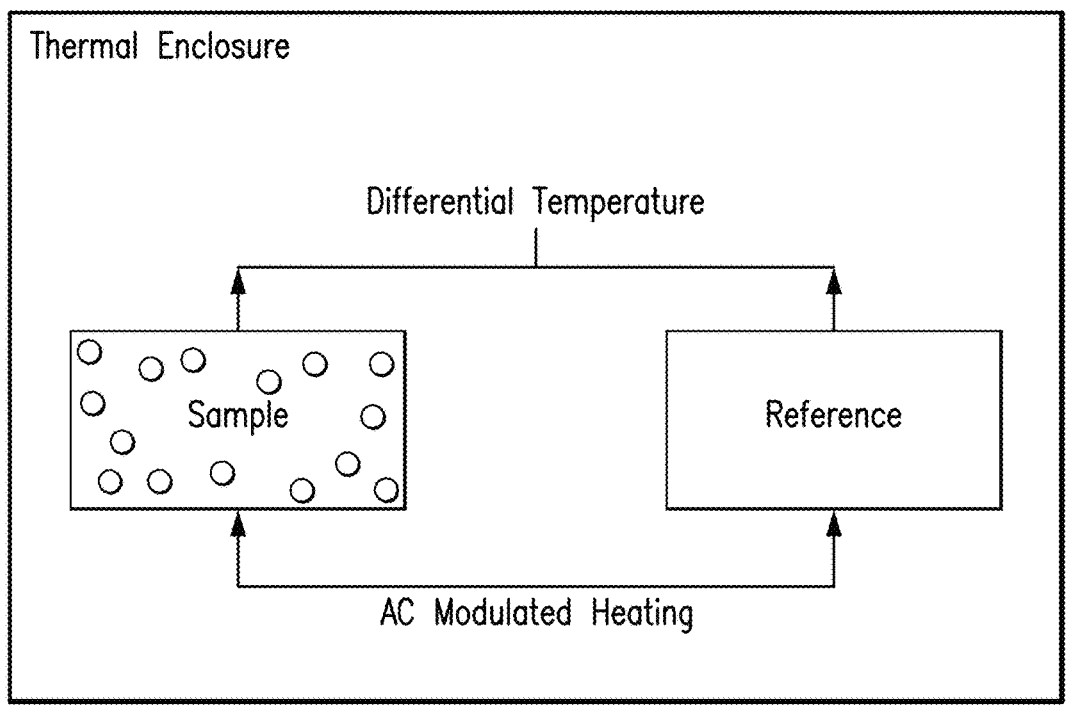
FIG. 3 is a schematic diagram illustrating the principle of AC differential scanning calorimetry according to the disclosed subject matter.

In some embodiments of the above method, a temporally periodic variation, or AC modulated heating, can be introduced to the reference and sample materials during the heating of the thermal enclosure, as illustrated in FIG. 3. This can lead to temperature modulation, which allows thermal relaxation of biomolecules, as well as allow the biochemical reaction signal to be readily extracted at the modulation frequency in the broad-band background noise. The temperature modulation can be achieved by using the microheaters included in the thin film substrate of the microdevice, controlled by a wave generator which can provide different frequency, magnitude, and other parameters for the on-chip heating.

In accordance with another aspect of the disclosed subject matter, a method of determining heat involved in a reaction between at least two substances is provided. The method includes: providing a MEMS device as described above; providing a thermal enclosure enclosing the microdevice; feeding a sample solution into the first thermally isolated microchamber, wherein the sample solution is prepared by mixing a first substance with a second substance; feeding a reference solution into the second thermally isolated microchamber, the reference solution does not contain at least one of the first and the second substances; and determining the heat involved in the reaction between the first substance and the second substance based on the measured temperature differential between the sample chamber and the reference chamber. During the measurement, the temperature of the thermal enclosure (that encloses the microdevice) can be maintained at a constant value. Thus, the method is also referred to as isothermal titration calorimetry (ITC). The reaction between the first and second substances can be a chemical reaction or physical binding. Thus, the two substances can be any of the variety of chemicals, biomolecules or other molecules that are reactive to each other, receptor-ligand, protein-enzyme, acid-base, etc., wherein the reaction between the two substances either generate, or absorb measurable heat.

Figure 29:
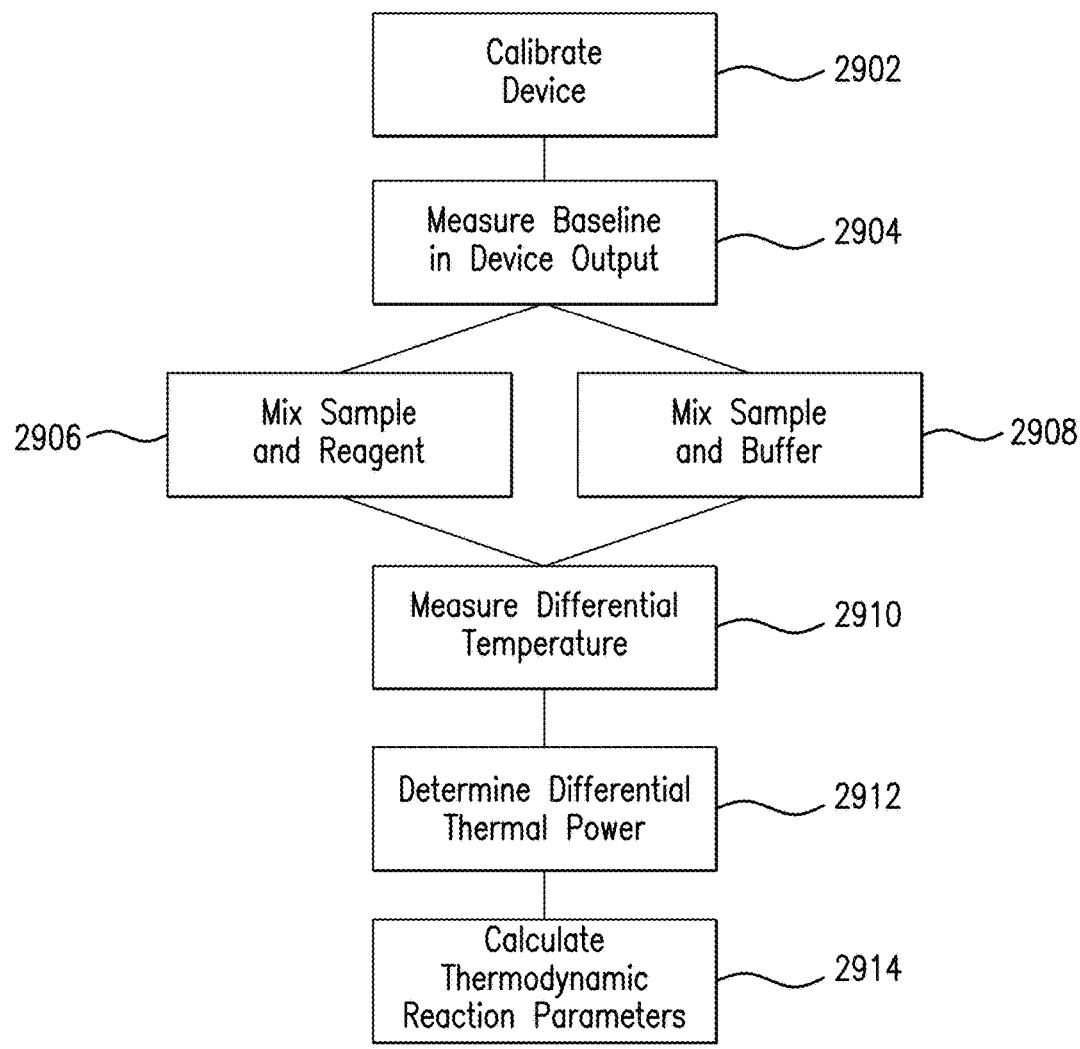
FIG. 29 is a flowchart illustrating a method for measuring a differential temperature and characterizing a reaction in accordance with an exemplary embodiment of the disclosed subject matter.

An exemplary method for measuring a differential temperature and characterizing a reaction in accordance with an embodiment of the disclosed subject matter is shown in FIG. 29. The method can include calibrating the device, measuring a baseline in device output, mixing the sample and the reactant, mixing the sample and the buffer, measuring a differential temperature, determining the thermal power, and calculating the thermodynamic reaction parameters.

To begin, the calorimetric device can be calibrated at 2902. For example, calibration techniques known in the art are described in A MEMS Differential-Scanning-Calorimetric Sensor for Thermodynamic Characterization of Biomolecules by Bin Wang and Qiao Lin, J. Microelectromechanical Systems 21:5, 1165-1171 (October 2012), which is incorporated by reference herein in its entirety for all purposes.

The baseline in device output can then be measured at 2904. For example, if a thermopile is used to measure the differential temperature, the thermopile output voltage in the absence of a reaction can be measured. This can be accomplished by introducing a mixture of sample and buffer solutions into each of the chambers. The baseline in device output can then be stored in storage device 2808 as shown in FIG. 28 for future use.

A sample and a reactant can then be mixed at 2906. The sample and a buffer can be mixed substantially simultaneously at 2908. Mixing can be accomplished using a passive chaotic mixer such as the one illustrated in FIG. 4*a*. Using the device 400, the sample can introduced into inlet 431 and the reactant can be introduced into inlet 432. The sample and a buffer can be introduced in corresponding inlets to introduction channel 440. The sample and the reactant are passively mixed in introduction channel 430 and deposited into the sample chamber 410. The sample and the buffer are passively mixed in introduction channel 440 and deposited into the reference chamber 420. Titration techniques known in the art for use with Isothermal Titration calorimetry (ITC) can be used.

In accordance with an embodiment of the disclosed subject matter, titration on the MEMS device can be performed with a series of discrete reactions, with each reaction having a specific molar ratio of the reactants. Liquid cartridge segments can be used for introduction of reactants. For example, binding reagents in different concentrations can be prepared while the sample is prepared in a fixed concentration. As such, the molar ratio can be varied with the volume of sample and binding reagent maintained identical (e.g., 0.5 μL). The sample and binding reagent can each be loaded in a long access tubing sequentially separated by air (such that the molar ratio changes along with the sequence of reactant segments). The access tubes can be driven by a multi-port syringe pump. A each molar ratio, the syringe pump can deliver the exact amount of sample and reagent into the reaction chamber for heat measurement, as well as sample and buffer into the reference chamber. Buffer segments can also be added between two reactant segments in the sequence for purposes of cleaning the chamber or mixer.

With further reference to FIG. 29, the differential temperature of the reactions is measured at 2910. The measurement can be accomplished using a thermoelectric sensor such as a thermopile. The thermopile can output a voltage indicative of the differential temperature. The output voltage can then be adjusted based on the baseline in device output measured at 2904.

The differential temperature can then be used to determine a thermal power related to the reaction at 2912. The thermal power difference ΔP can be calculated as:

$$\Delta P = \frac{\Delta U}{S} \quad (1)$$

where ΔU is the output from the thermoelectric sensor and S is the thermoelectric sensitivity, i.e., the output electrical voltage generated by unit differential thermal power.

The differential thermal power can then be used to calculate the thermodynamic reaction parameters at 2914. In general, a biochemical reaction between a sample molecule M and a binding reagent X can be represented as:

$$n_1 X + n_2 M \rightarrow MX + \Delta H \quad (2)$$

where the reaction results in the product MX accompanied by a change of enthalpy ΔH. In ITC, the binding reagent X is titrated, i.e., successively added in known aliquots, into the sample, while the reaction heat is measured. The reaction heat is measured. The reaction heat is used to calculate the thermodynamic properties of the reaction, including the equilibrium binding constant $K_B=[MX]/[X][M]$ (where [•] denotes the equilibrium concentration of the species), stoichiometry $N=n_1/n_2$, and molar enthalpy change ΔH. In particular, the reaction heat can be calculated based on the differential thermal power. The biochemical reaction heat can be expressed as:

$$Q = \frac{NM_t \Delta H V_0}{2}\left[1 + \frac{r}{N} + \frac{1}{NK_B M_t} - \sqrt{\left(1 + \frac{r}{N} + \frac{1}{NK_B M_t}\right)^2 - \frac{4r}{N}}\right] \quad (3)$$

where Q is the biochemical reaction heat evolved at a molar ratio $r=X_t/M_t$, $V_0$ is the active volume for the reaction, $M_t$ is the total concentration of the sample, free plus bound, in the reaction cell of volume $V_0$, and $X_t$ is the total concentration of the reagent that is titrated into the sample solution.

In order to calculate the thermodynamic reaction parameters, an integral of the differential thermal power is computed. The resulting value is used as the biochemical reaction heat. A number of data points can be gathered based on the voltage measurements from a number of trials using different molar ratios. The resulting data can then be fitted to Equation (3) in order to calculate the thermodynamic reaction parameters. Fitting can be accomplished using fitting methods as known in the art for its intended purpose.

Figure 4A:
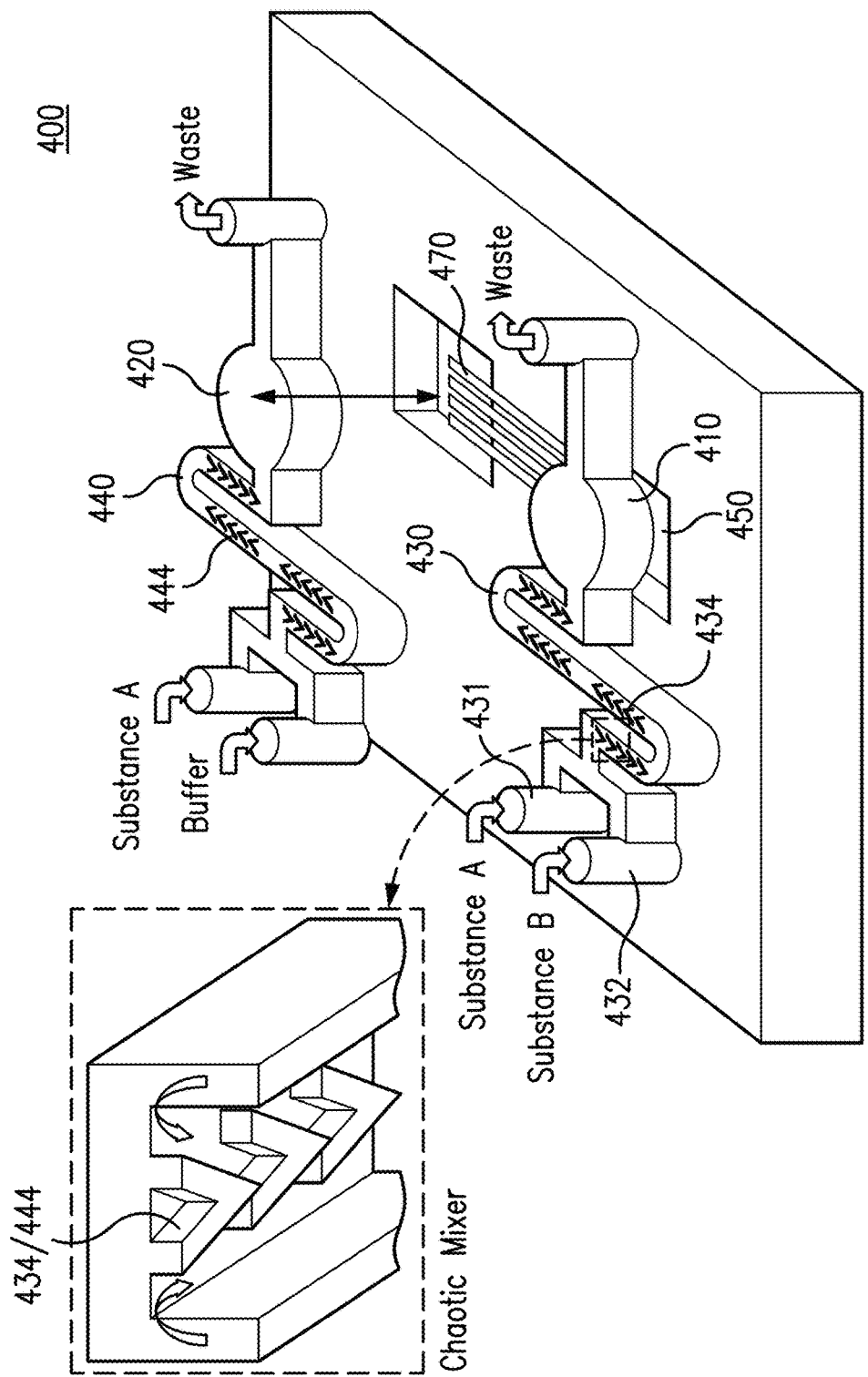
FIGS. 4a and 4b are schematics of a microdevice according to some embodiments of the disclosed subject matter for isothermal titration calorimetry.
Figure 4B:
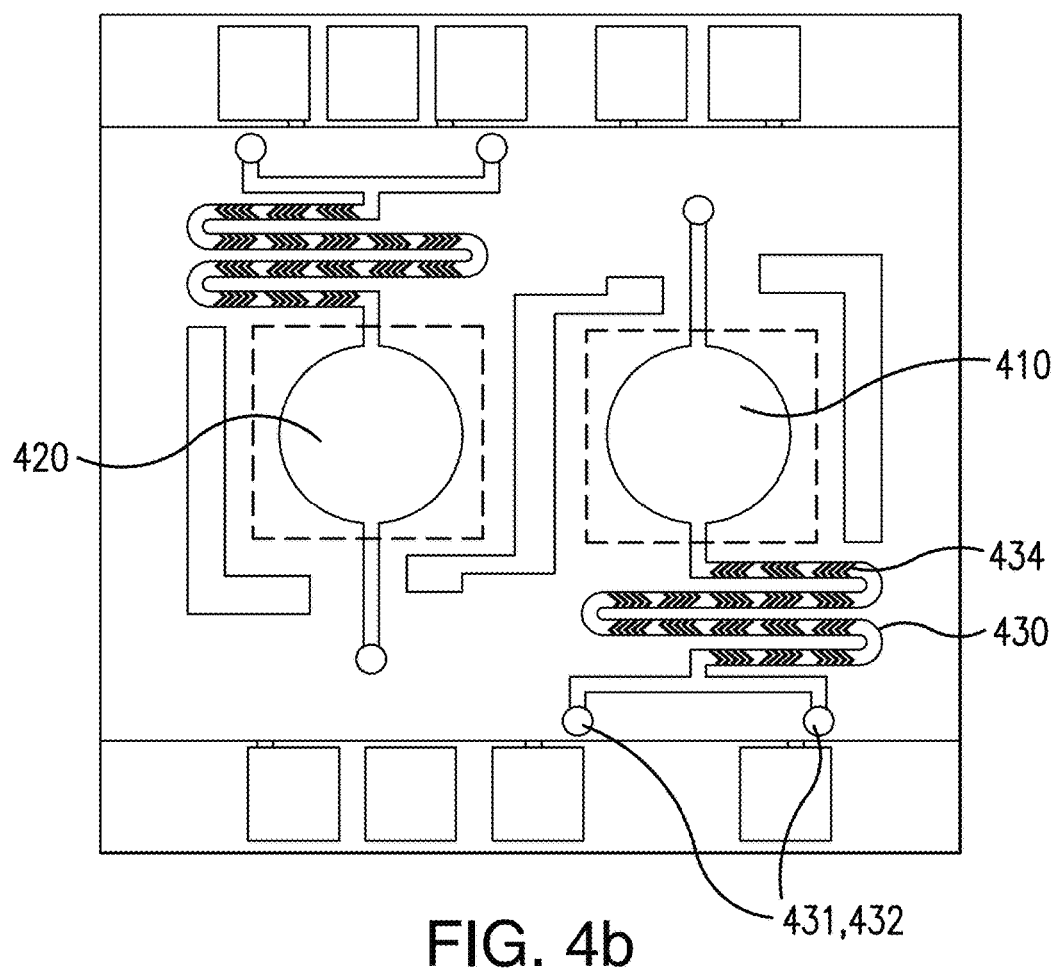

FIG. 4 is a schematic representation of the exploded view of a microdevice that can be used for the ITC. The microdevice (400) includes a sample chamber (410) and a reference chamber (420), both situated on the thin film substrate (450) which includes a thermopile (470) for measuring the temperature differential of the sample chamber and the reference chamber during a heat scan. To facilitate mixing of the first and second substances (A and B), the microdevice further includes introduction channels (430, 440) for each of the sample and reference chambers (410, 420). Each of the introduction channels has two inlets (431, 432; 441, 442). Each of the introduction channels can be configured to provide passive chaotic mixing for a solution flowing through the channel. For example, as schematically shown in FIGS. 4a and 4b, the introduction channels (430, 440) can include a portion having a serpentine shape. Moreover, the introduction channels (430, 440) can includes internal ridges (434, 444) sufficient for creating turbulence in the solution flowing through channels. For example, as shown in the inlet of FIG. 4a, the introduction channels can include herringbone-shaped ridges in the ceiling.

In certain embodiments, the disclosed device can perform a three-dimensional diffusion-based mixing, which directs fluid streams to create multiple mixing interfaces. For example, but not by way of limitation, such multiple mixing interfaces may be created by the utilization of a bismuth-antimony (Bi—Sb) thermopile integrated with 3D diffusive titration channels, thereby combining the functionalities of micromixing, titration, and thermoelectric transducing. The change in interface area can decrease the length of diffusion for the molecules, which can enhance mixing, shorten mixing lengths and decrease heat losses. See, as one non-limiting example, section Example 8 below, which utilizes the Bi—Sb thermopile integrated with 3D diffusive titration channels to promote three-dimensional diffusion-based mixing. In another embodiment, the disclosed device can include a channel and/or reaction chamber having a non-planar surface that can be utilized with geometries having curvature.

The disclosed microdevice and methods of fabrication and use thereof are further illustrated in the examples below, which should not be considered as limiting the scope of the disclosed subject matter in any way.

Example 1: Fabrication of Microdevice

This example illustrates a procedure to fabricate the microdevice, which substantially follows the outlined procedure described above in connection with FIG. 2. In particular, a 6-μm thick polyimide film was spin-coated on a silicon wafer (precoated with silicon dioxide). The TMAH etching into the backside of the wafer in the areas that correspond to the calorimetric chambers created an approximately 50 μm-thick residual wafer layer. After the curing of the polyimide, a chromium/gold thin film (5/200 μm) was deposited by thermal evaporation onto the polyimide layer.

A second layer of polyimide was then coated on the microheaters and temperature sensors. Subsequently, Sb and Bi thin films (0.5 and 1.2 μm) were thermally evaporated and patterned using a standard lift-off process to form a 50-junction thermopile using a standard lift-off process. A layer containing polyimide-PDMS mixture was further coated on the thermopile. The chamber housing structure was fabricated from PDMS using micromolding techniques on top of the thin film substrate, thereby forming the calorimetric chambers the calorimetric chambers each of cylindrical shape and 1 μL in volume (diameter: 2.5 mm and height: 200 μm), with a center-to-center separation of 4 mm. Xenon difluoride ($XeF_2$) gas-phase isotropic etching was used to remove the residual silicon layer on the wafer substrate from the backside of the thin film substrate. The integrated resistive microheaters each had a nominal resistance of 40Ω and the temperature sensors each had a nominal resistance of 55Ω. Shown in FIG. 5 are the images of the PDMS housing structure and solid thermal substrate, as well as micrographs of the thermopile, integrated microheater and temperature sensor embedded in the thin film substrate.

Example 2. Calorimetric Measurement

In this example, the microdevice as fabricated according to Example 1 was calibrated and used to measure thermodynamic properties of certain biomolecules, e.g., thermodynamics of the unfolding of a protein.

A. Principle

DSC can measure differential heat capacity, i.e., the heat capacity difference between a sample and a reference material, as a function of temperature. When the sample and reference materials are subjected to identical temperature scanning, i.e., their temperatures are varied at a predetermined rate within a range of interest, the thermally induced activity of the sample molecules, which is either exothermic or endothermic, can cause a small temperature difference between the sample and reference materials (i.e., differential temperature or temperature differential). This differential temperature can be detected to reflect the differential power $$\Delta P = P_s - P_r \quad (4)$$

where $P_s$ and $P_r$ are the thermal power generated in the sample and reference materials, respectively. Therefore the differential heat capacity $$\Delta C_p = C_{ps} - C_{pr} \quad (5)$$

where $C_{ps}$ and $C_{pr}$ are, respectively, the heat capacities of the sample and reference materials, can be determined as:

$$\Delta C_p = \frac{\Delta P}{\dot{T}} = \frac{\Delta U}{S\dot{T}} \quad (6)$$

where $\dot{T}$ is the time rate of the controlled temperature of sample and reference materials, U is the output from the thermoelectric sensor that is employed to detect the differential temperature, and S is the device's sensitivity, i.e., the output electrical voltage generated by unit differential thermal power. Therefore, interpretation of the differential heat capacity can lead to determination of the fundamental thermodynamic properties of the sample material.

B. Device Calibration

Figure 6A:
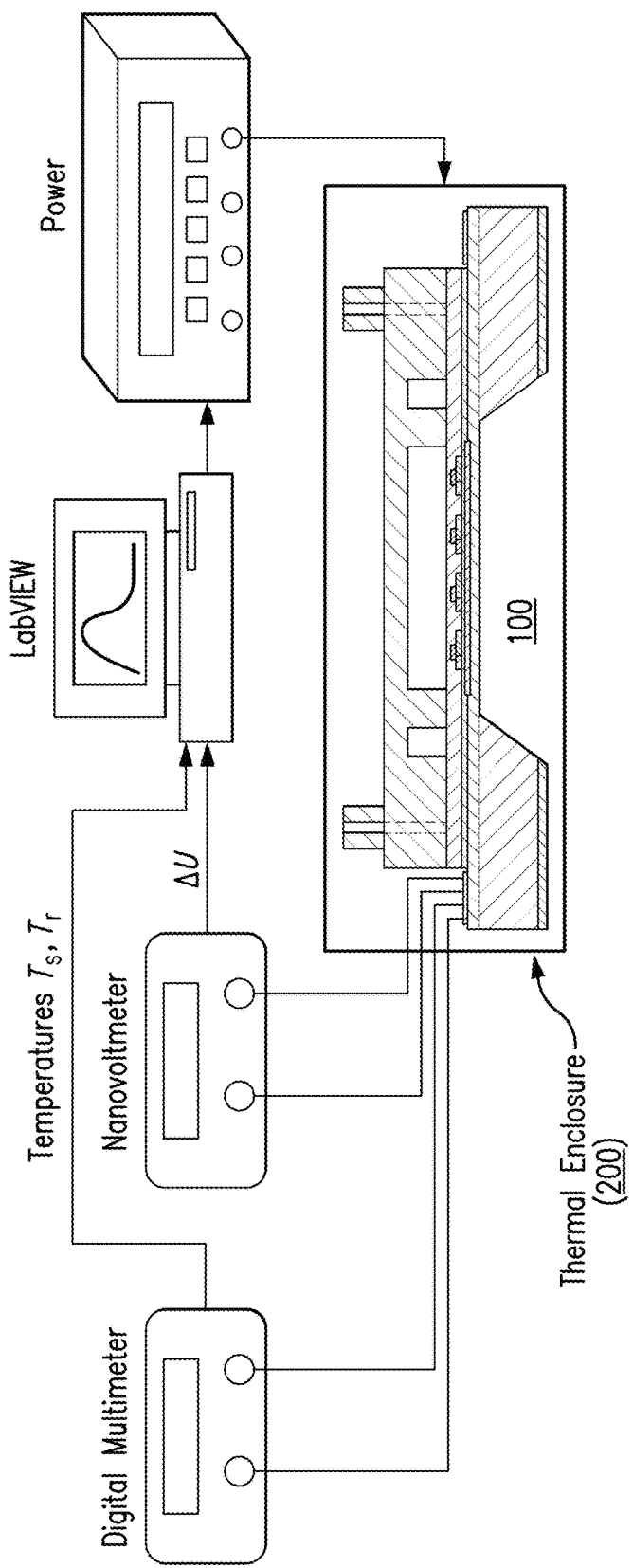
FIG. 6a is a schematic diagram of a testing setup for a calorimetric measurement using a microdevice according to some embodiments of the disclosed subject matter.

In order to measure the temperature differential between the two chambers, the thermopile need be first calibrated such that the voltage generated by the thermopile can be readily convert to temperature differential. As illustrated in FIG. 6a, to calibrate the MEMS DSC device, the on-chip microheaters were driven by a DC power supply (Agilent E3631A) and generated a constant differential heating power in the calorimetric chambers, while the temperature sensors were interrogated by a digital multimeter (Agilent 34410A) to monitor the temperatures of the calorimetric chambers. The thermopile output voltage, proportional to the differential temperature between the chambers, was measured by a nanovoltmeter (Agilent 34420A). The temperature control of the MEMS DSC device and thermoelectric measurements were automated using a personal computer via a LabVIEW-based program.

Figure 6B:
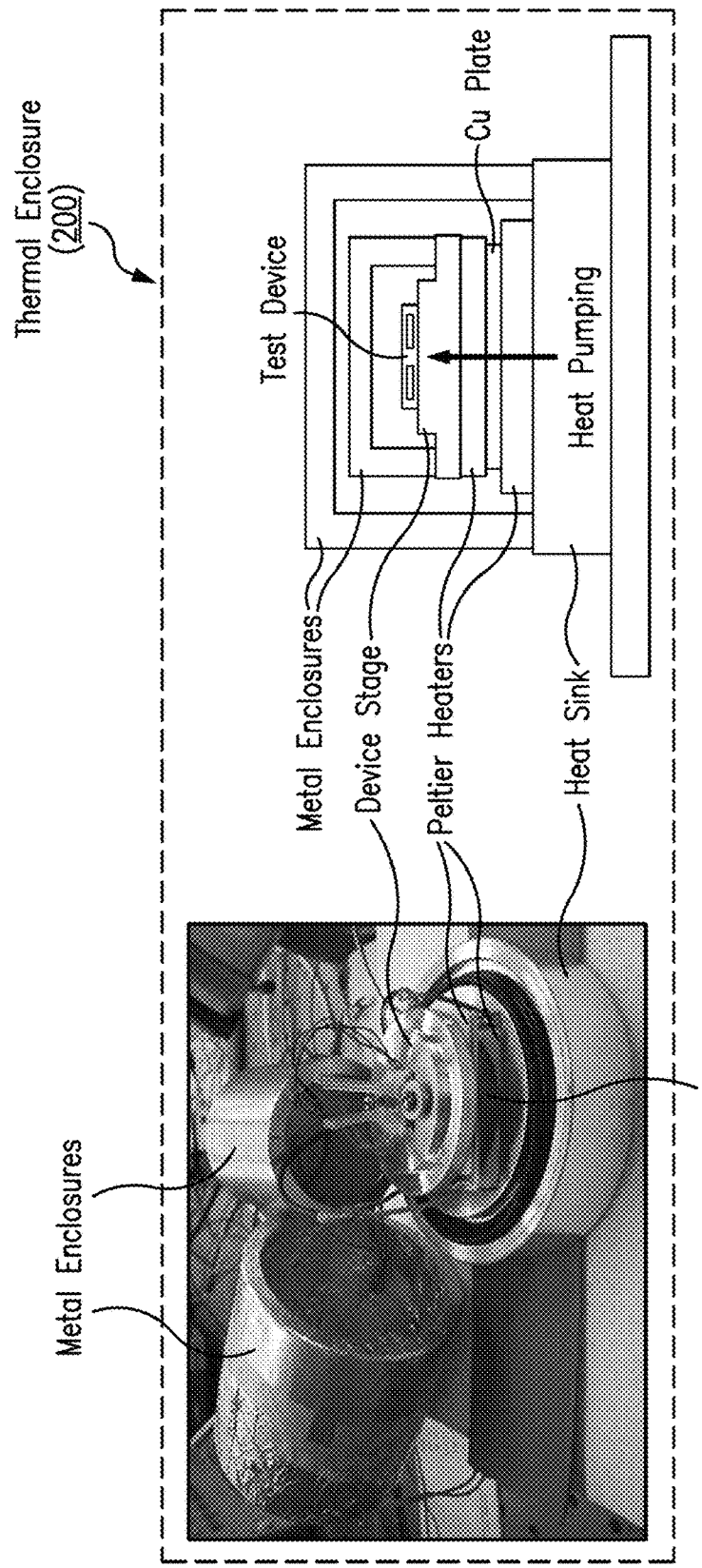
FIG. 6b shows the details of a custom-built, temperature-controlled thermal enclosure as compared with a schematic diagram of the thermal enclosure, according to some embodiments the disclosed subject matter.

A packaged MEMS DSC device (100) was housed in a custom-built, temperature-controlled thermal enclosure (200) including multiple metal enclosures surrounding a metal stage on which the device was placed (FIG. 6b). This provided temperature scanning of the sample and reference solutions, as well as thermal isolation of the device package from the environment to minimize measurement noise. Multiple Peltier devices (Melcor UT15-12-40-F2) were located underneath the device stage, and by a power supply (Agilent E3631A), to add heat to or remove heat from the device. The temperature of the sample and reference chambers was controlled in closed loop by adjusting the voltage applied to the Peltier devices according to the feedback from the on-chip temperature sensors based on, for example, a proportional-integral-derivative (PID) algorithm.

During device calibration, the sample and reference chambers were both filled with 0.1 M Glycine-HCl buffer (pH 2.5), which was the buffer later used for protein unfolding measurements. A known, constant differential power was created by activating the microheater below the sample chamber while leaving the microheater underneath the reference chamber turned off. The temperature sensors were used to measure the temperatures of the thermopile's hot and cold junctions. The device output, i.e., the thermopile output voltage, was measured as a function of time to obtain the steady-state and transient responses to the differential heating power.

Figure 7:
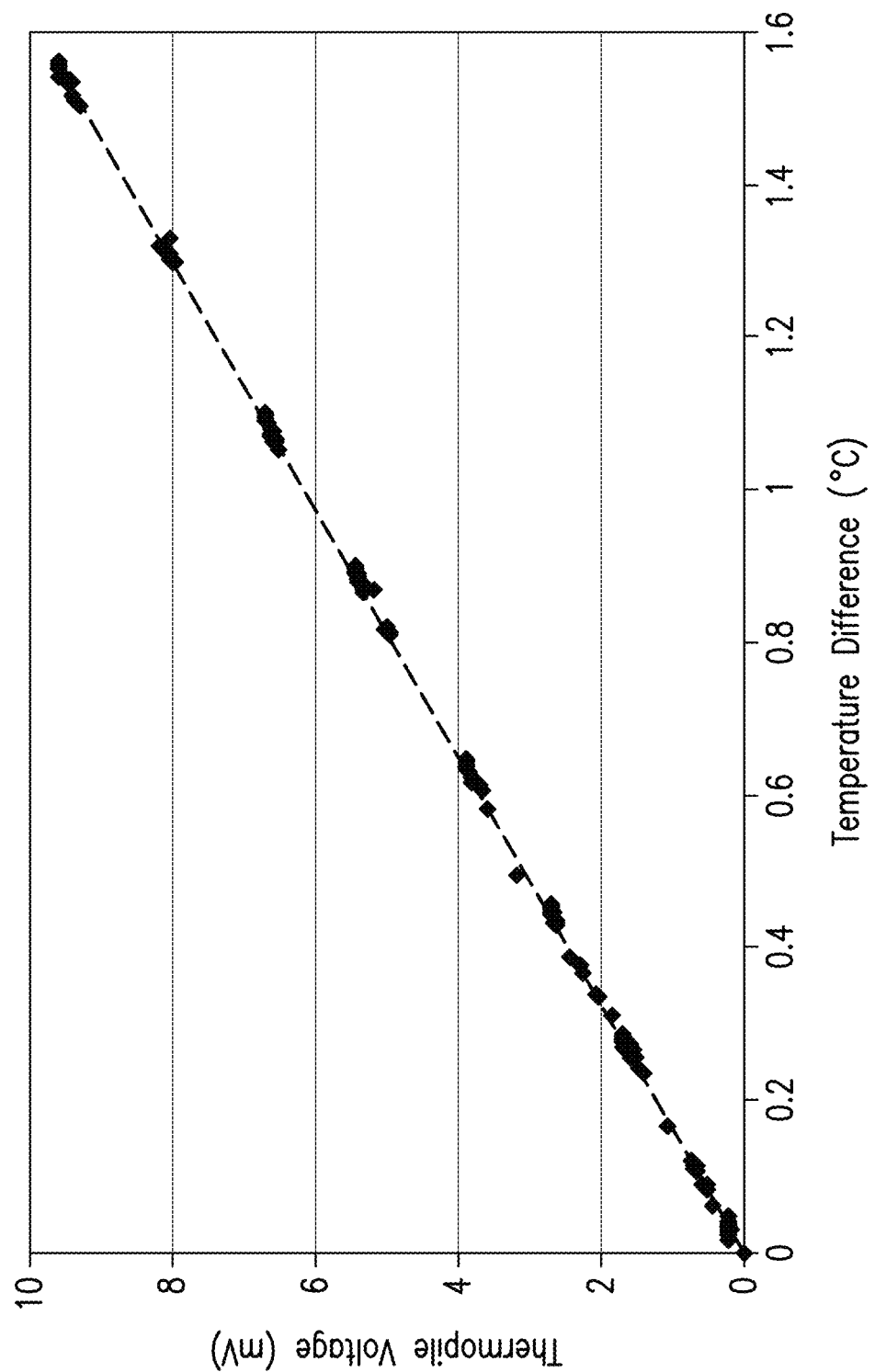
FIG. 7 is a plot showing the thermopile output voltage from a microdevice according to some embodiments the disclosed subject matter in response to constant temperature difference between the thermopile's hot and cold junctions.
Figure 8:
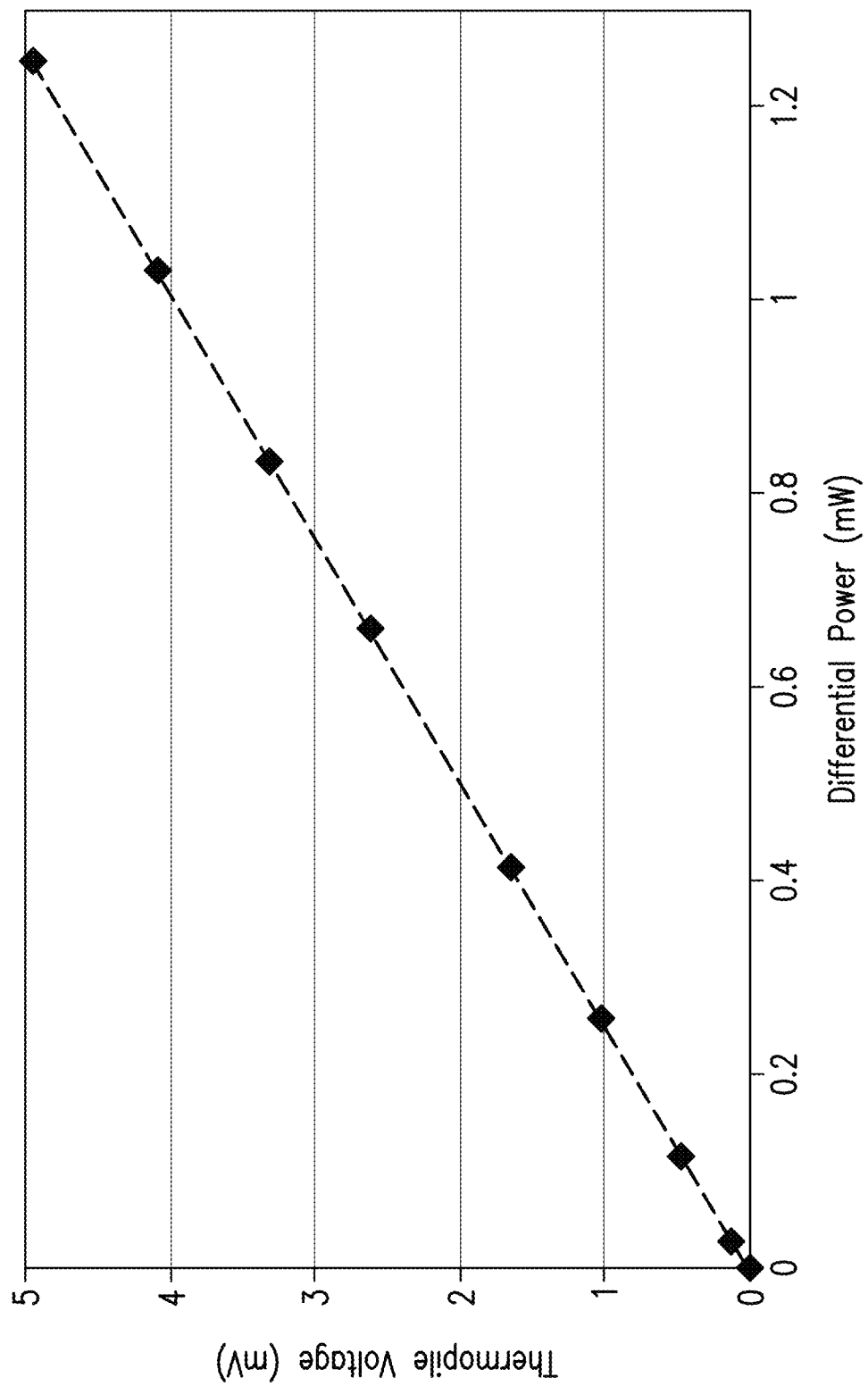
FIG. 8 is a plot showing a steady-state response (in terms of thermopile output voltage) from a microdevice according to some embodiments the disclosed subject matter in response to constant differential power between the two chambers of the microdevice.

The sensitivity of the thermopile integrated in the MEMS DSC device was calibrated at varying temperature difference between the hot and cold junctions, generated by on-chip heating (using the microheater underneath the sample chamber). The thermopile differential voltage exhibited a highly linear relationship with temperature difference (FIG. 7), showing a total thermoelectric sensitivity of 6.3 mV/° C. for the 50-junction thermopile. A Seebeck coefficient of 125 μV/K for each Sb—Bi thermocouple was obtained. In addition, the steady-state response of the MEMS DSC device was calibrated to varying differential power and observed again a highly linear relationship, yielding a nearly constant responsivity of S=4.0 mV/mW (FIG. 8). A root-mean-square (RMS) noise of approximately 40 nV in the device output was also observed, which was used to determine a baseline noise in the differential power. This corresponded to a detection limit of approximately 10 nW in differential thermal power measurement.

Figure 9:
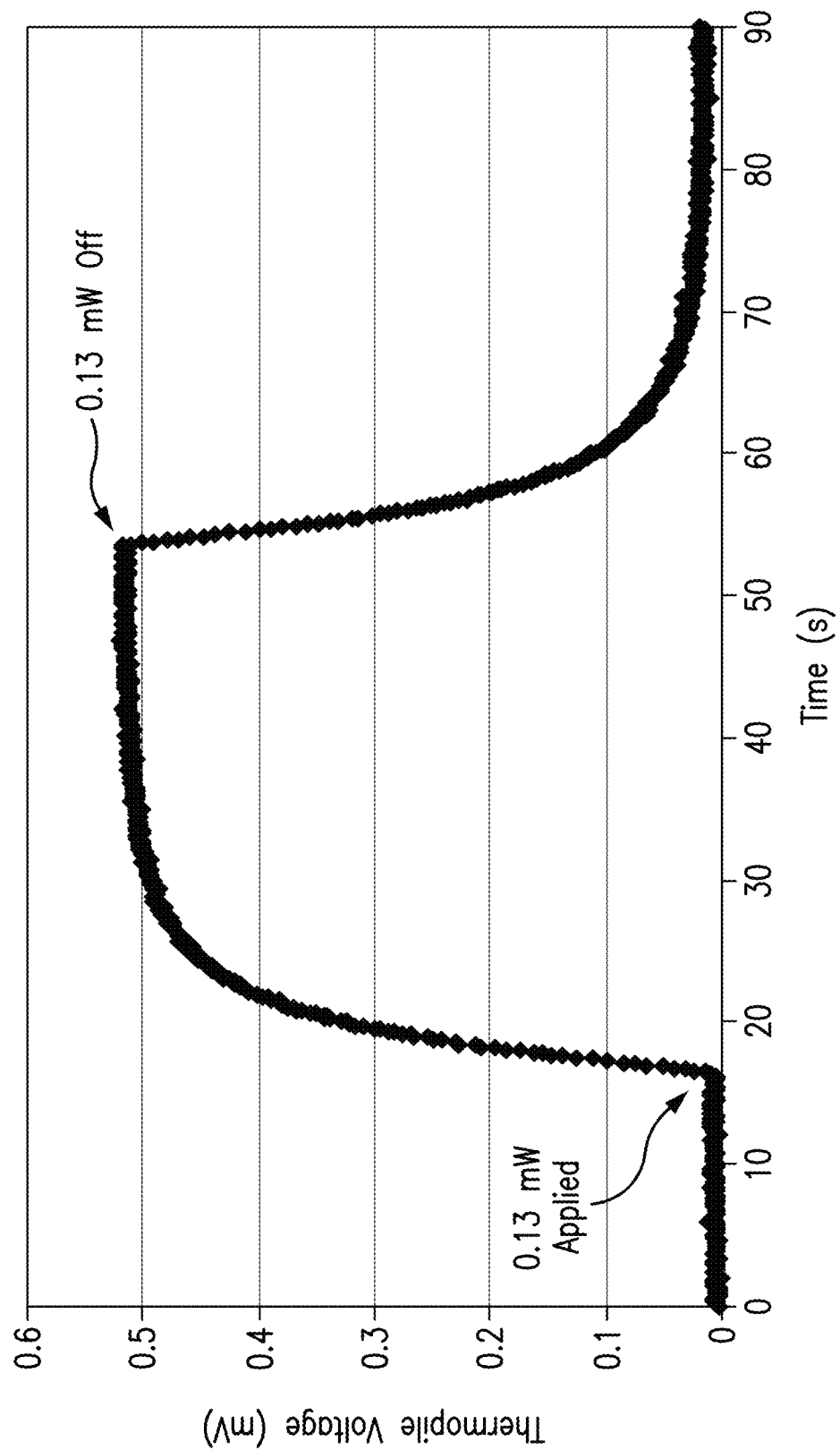
FIG. 9 is a plot showing the transient response of a microdevice according to some embodiments the disclosed subject matter with respect to a step differential power.

To characterize the transient response of the MEMS DSC device, a step differential power of 130 μW was initially applied to the calorimetric chambers and then turned off once the device output reached its equilibrium. The corresponding output voltage from the thermopile (FIG. 9) was found to exponentially grow with time upon the application of the differential power, while decay exponentially upon the removal of the differential power. The thermal time constant was approximately 2.0 s, calculated by fitting the experimental data to first-order exponential growth and decay functions.

C. Calorimetric Measurements

DSC measurements of biomolecules were performed using the calibrated microdevice, whose sample chamber and reference chamber were respectively filled with biological sample and buffer solutions, scanned in a range of temperature of interest. The temperature sensors were used to monitor the temperatures of calorimetric chambers while the device output was obtained in real time to compute the biomolecular thermal power. Before DSC measurements, the baseline in device output, i.e., the thermopile output voltage in the absence of a differential power input, during temperature scanning was measured with both calorimetric chambers filled with buffer solutions. Biological sample and buffer solutions were degassed with a vacuum chamber built in-house, metered with micropipettes, and introduced by a syringe pump (New Era Pump Systems, NE 1000).

The calibrated MEMS DSC device was employed to characterize protein unfolding, a common type of biomolecular conformational transition. For this purpose, the thermal enclosure provided temperature scanning of the MEMS DSC device at time rates as high as 6° C./min in the range of 10-90° C. with power consumption lower than 25 W. Using lysozyme prepared in 0.1 M Glycine-HCl buffer (pH 2.5) for purposes of demonstration, the device output was monitored while the sample and reference chambers, respectively filled with lysozyme and buffer, were scanned in a temperature range of 25-75° C. at a constant rate of 5° C./min.

Figure 10:
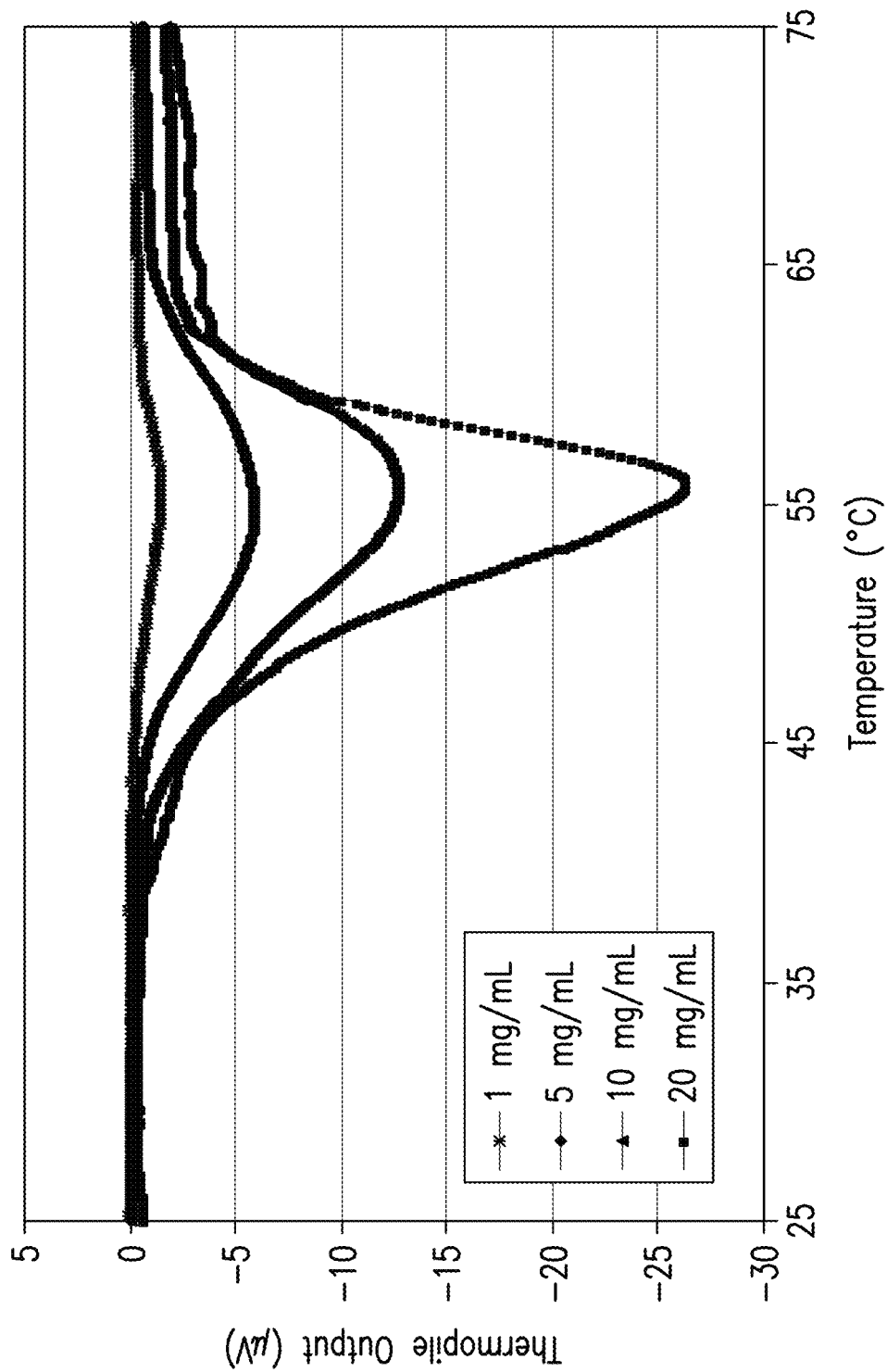
FIG. 10 is a plot showing the output of a microdevice according to some embodiments the disclosed subject matter as a function of temperature in a temperature scan during which the unfolding of lysozyme occurs.

The thermopile output voltage as a function of temperature, corrected by baseline subtraction, was measured at varying protein concentrations ranging from 1 to 20 mg/mL (FIG. 10). It was observed that the device output exhibited a concentration-dependent minimum within a certain temperature range, reflecting the endothermic nature of protein unfolding processes. Notably, the unfolding of lysozyme was detectable at 1 mg/mL, representing a significant improvement over the previously reported MEMS DSC device.

Figure 11:
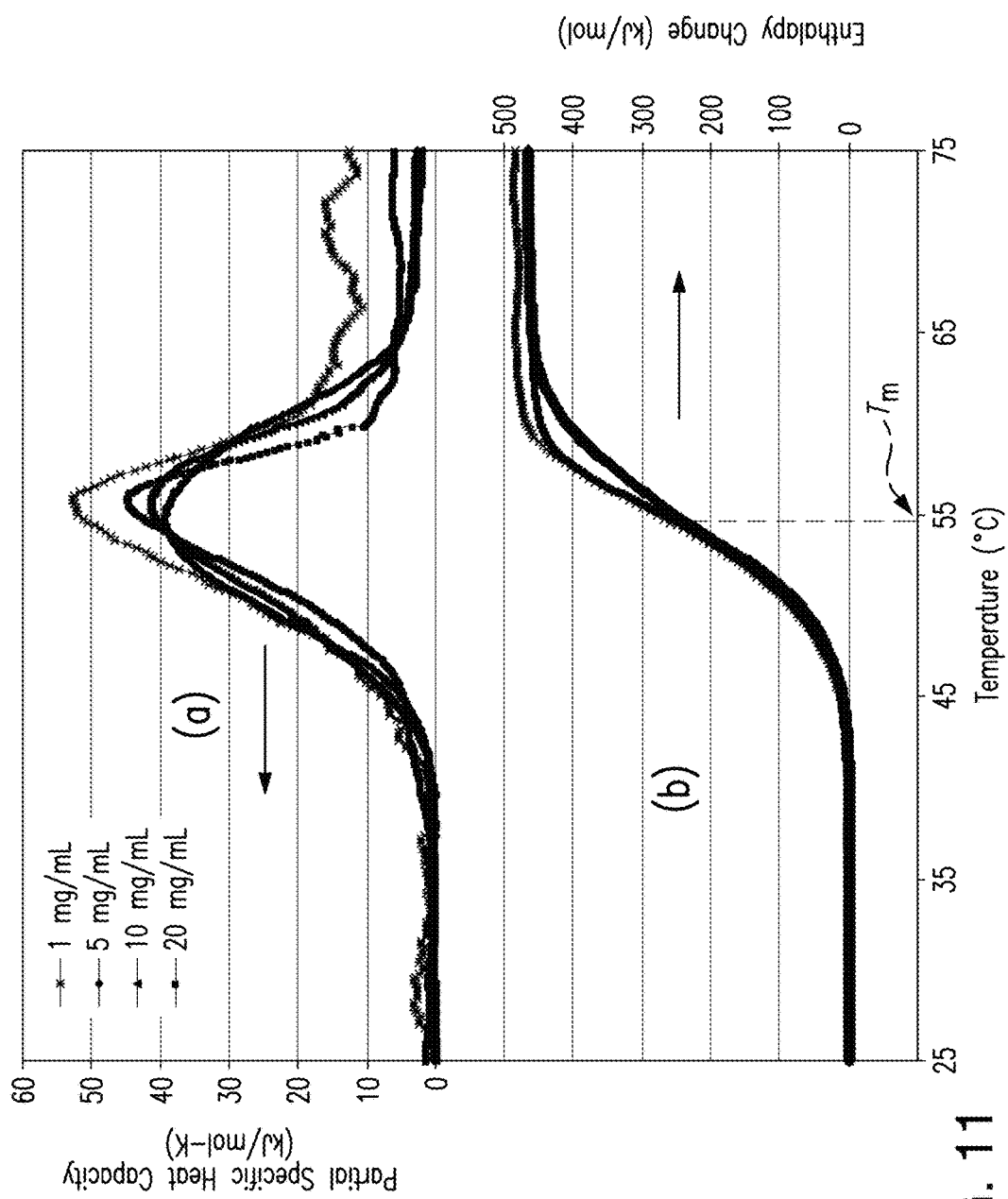
FIGS. 11a and 11b are plots showing partial specific heat capacity (11a) and change of molar enthalpy (11b) as a function of temperature during the unfolding of lysozyme, as measured by the microdevice according to some embodiments the disclosed subject matter.

Furthermore, the differential heat capacity between the chambers was computed from the differential voltage measurement (FIG. 10) using calibrated device sensitivity (4.0 mV/mW), allowing the thermodynamic properties of lysozyme to be obtained during its unfolding process, such as partial specific heat capacity (c) (FIG. 11a), the total change of molar enthalpy (i.e., enthalpy per mole of lysozyme) (ΔH), and melting temperature ($T_m$, defined as the temperature at which the change of molar enthalpy achieves 50% of ΔH) (FIG. 11b). Despite the amplitude difference of device output at various protein concentrations, they all yielded consistent estimates of the thermodynamic properties associated with the protein unfolding process. In particular, the profile shape of c was generally not influenced by protein concentration, and ΔH was consistently determined to be approximately 450 kJ/mol with a corresponding melting temperature $T_m$ of approximately 55° C. These results agree well with published data, which are typically in the range ΔH=377-439 kJ/mol and $T_m$=55-58.9° C. for lysozyme, demonstrating the potential utility of the MEMS DSC device disclosed herein for biomolecular characterization with significantly reduced sample consumption at practically relevant protein concentrations.

The effects of the temperature scanning rate on DSC measurements were also investigated. Using 20 mg/mL lysozyme prepared in 0.1 M Glycine-HCl buffer (pH 2.5) for example, the unfolding of lysozyme at temperature scanning rates were varied from 1-6° C./min. The thermopile output voltage (again corrected by baseline subtraction) (FIG. 12a) exhibited a consistent dip in the same temperature range for protein unfolding as indicated above, with an amplitude increasing with the temperature scanning rate. This is consistent with a larger heat flux resulting in a higher endothermic power through phase transformations.

Figure 12:
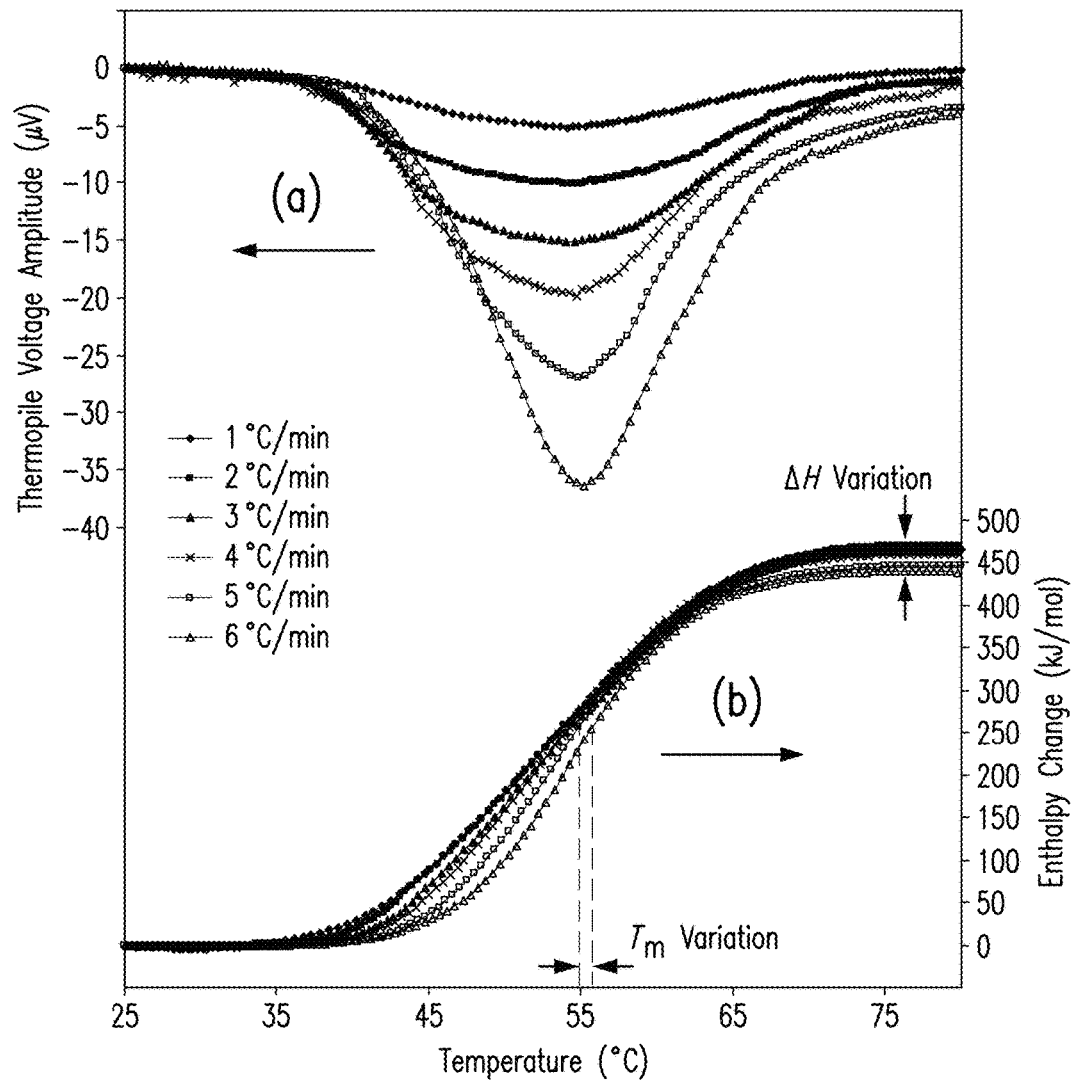
FIGS. 12a and 12b are plots showing the output of a microdevice according to some embodiments the disclosed subject matter (10a) and change of molar enthalpy as a function of temperature during the unfolding of lysozyme at varying temperature scanning rates.

These data were then used to compute the change of molar enthalpy (FIG. 12b). Although a slight shift in the device output could be observed (FIG. 12a) as temperature scanning rate increased, the thermodynamic properties associated with the protein unfolding process were found generally consistent, with a standard variation in ΔH of approximately 50 kJ/mol (i.e., ±5% of the mean value of ΔH) and a standard variation in $T_m$ of less than 1° C. (FIG. 12b). Notably, for temperature scanning at 1-5° C./min, the $T_m$ values were almost the same. This demonstrates the measurement consistency using the MEMS DSC device of the disclosed subject matter, and indicates that a temperature scanning rate as high as 5° C./min is adequate for the measurement of lysozyme unfolding.

Example 3. AC-DSC Measurement

This Example illustrates the method of carrying out a AC-DSC measurement, as described above based on a microdevice presently disclosed. This MEMS AC-DSC approach can potentially enable measurements of low-abundance biomolecules with improved accuracy, as demonstrated by the application of the device to AC-DSC measurements of the unfolding of lysozyme.

A. Principle

AC-DSC can monitor the differential heat capacity, i.e., the heat capacity difference between a sample and a reference material, by varying the materials' temperatures at a specified constant rate via a thermally isolated enclosure equipped with temperature control functionalities, superimposed with a temporally periodic variation via identical AC modulation heating applied to the sample and reference (FIG. 3). The differential heat capacity can be obtained by the measurement of the differential temperature, i.e., the temperature difference between the sample and reference materials.

B. Fabrication of the Microdevice, System Setup and Calibration

The AC-DSC measurement was carried out using a microdevice schematically depicted in FIG. 1 and fabricated according to the procedure described in Example 1. While other device parameters, including the dimension and volume of the chambers, thickness of polyimide paraphragms, and characteristics of the microheaters and temperature sensors, are largely the same as those of the microdevice described in Example 1, the Sb—Bi thermopile used in this Example includes 100 junctions rather than 50 junctions in Example 1.

Figure 13:
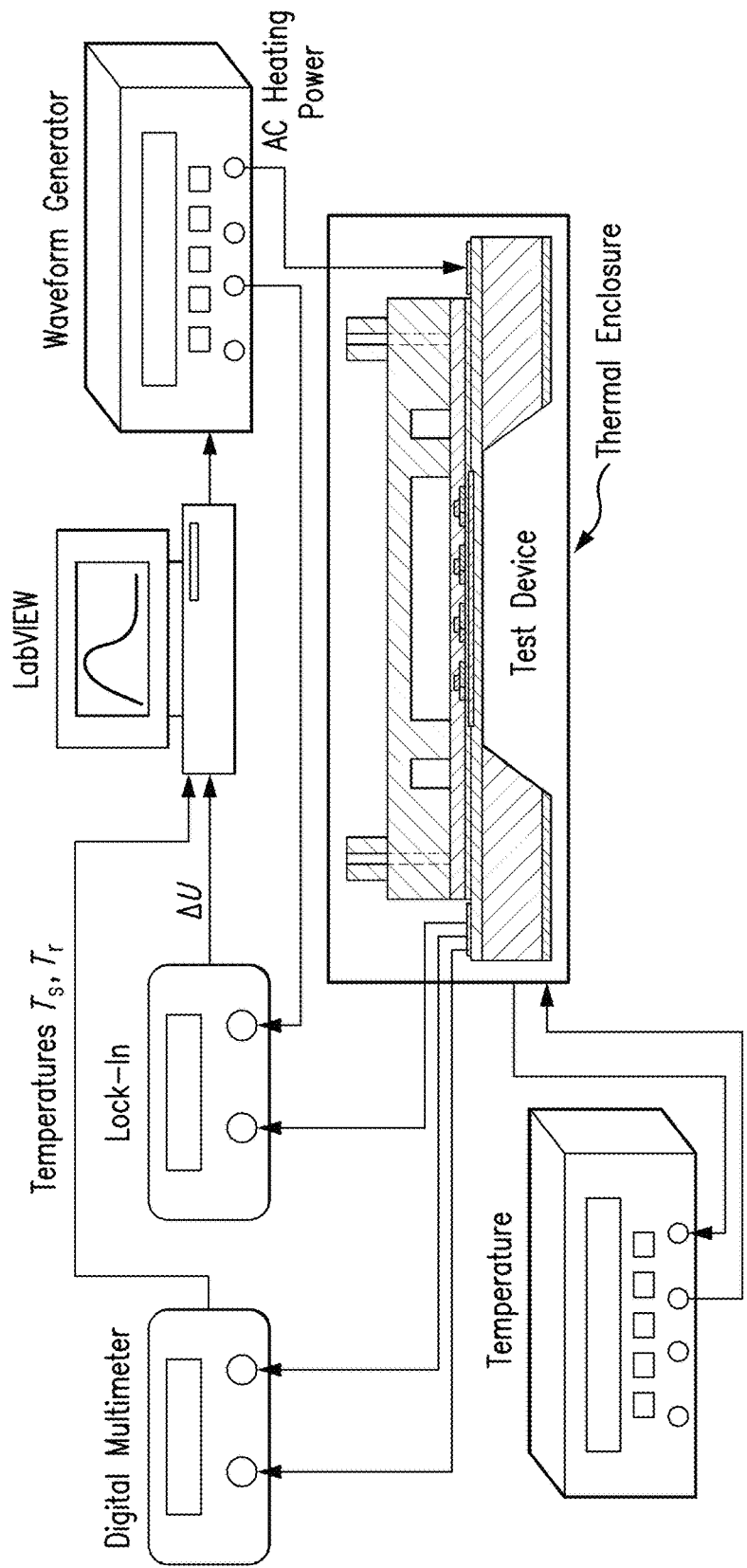
FIG. 13 is a schematic diagram showing an experiment setup for AC-DSC measurements according to some embodiments of the disclosed subject matter.

The DSC measurement system was configured similarly to that of Example 2. The microdevice was also placed in a thermal enclosure built in-house. The temperature of the sample stage in the thermal enclosure was controlled in closed-loop via a proportional-integral-derivative (PID) algorithm implemented by a commercial temperature controller (Lakeshore 331). The on-chip microheaters driven by a DC power supply (Agilent E3631A) were used to generate a constant differential power input, while for modulated heating, a square-wave AC voltage generated by a waveform generator (Agilent 33220A) was applied (FIG. 13). The temperature sensors were used to detect the real-time temperature inside each of the calorimetric chambers by a digital multimeter (Agilent 34410A). During device calibration, the thermopile output voltage was measured by a nanovoltmeter (Agilent 34420A), while during AC-DSC measurement, the amplitude and phase of thermopile voltage were measured by a lock-in amplifier (Stanford Research Systems SR830) referenced by the same AC modulation square wave from the waveform generator. The AC-DSC measurement was fully automated through a Lab VIEW program.

The methods for calibrating the DC performance of the MEMS device were substantially the same as described in Example 2. The baseline in device output, i.e., the thermopile voltage with no differential power input during temperature scanning, was measured with both chambers filled with buffer solutions. During calibration of the device's modulation frequency dependence and AC-DSC measurements, the sample chamber was filled with a biological sample solution while the reference chamber was filled with the buffer solution. Biological sample and buffer solutions were degassed with a vacuum pump built in-house and then introduced into the device's calorimetric chambers with micropipettes.

Figure 14:
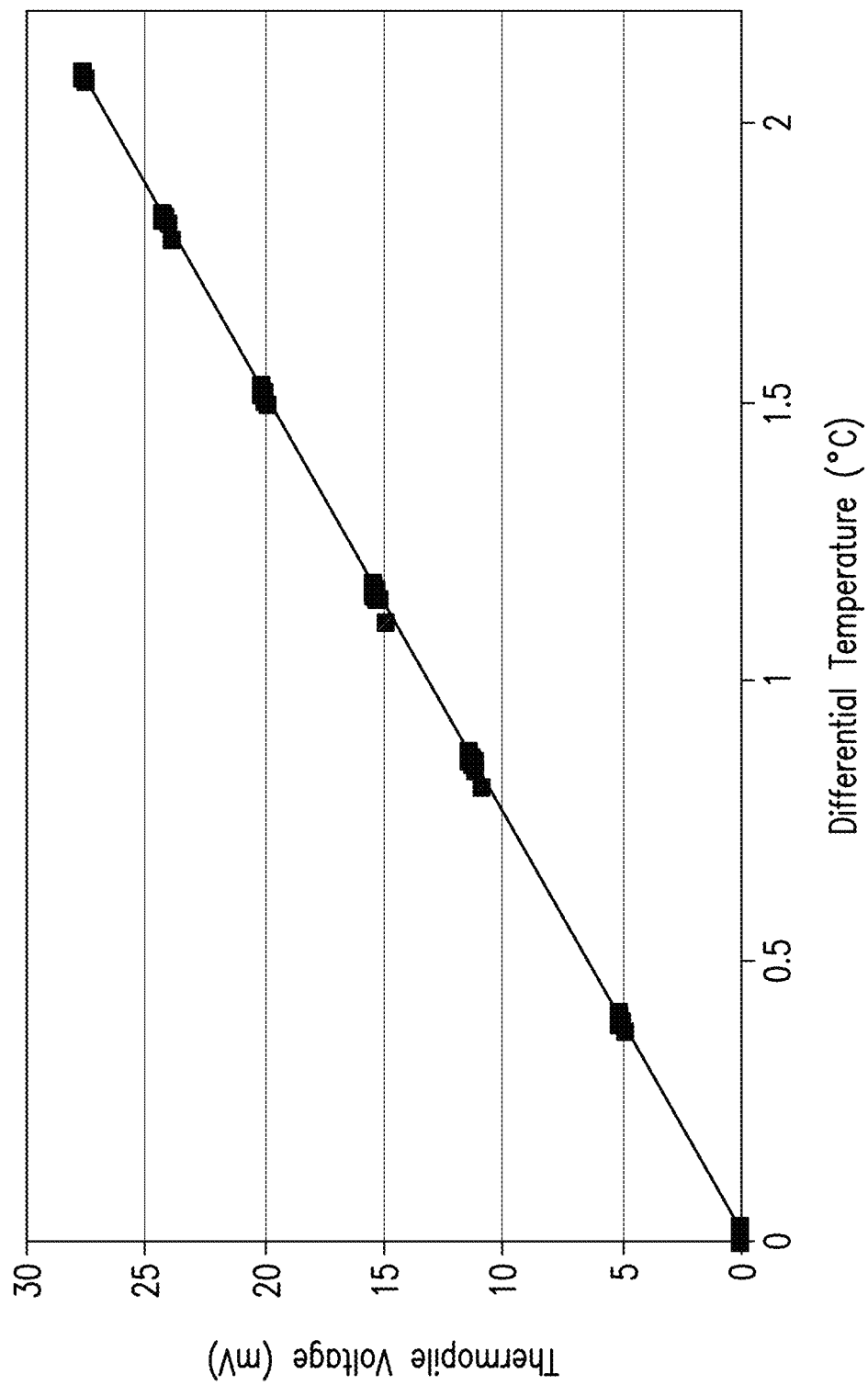
FIG. 14 is a plot showing the output voltage of the thermopile of a microdevice according to some embodiments of the disclosed subject matter in response to constant differential temperature between its hot and cold junctions.
Figure 15:
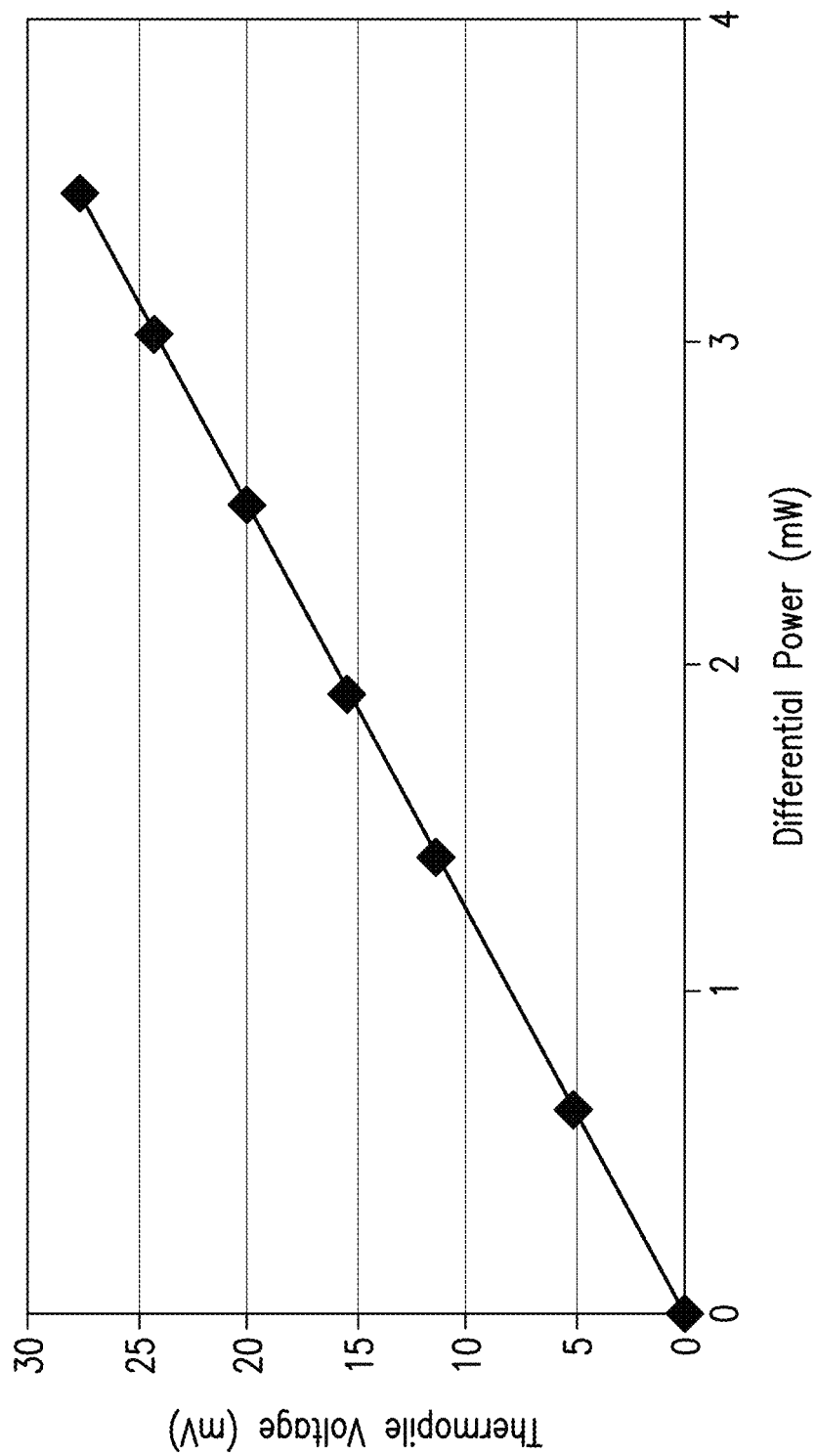
FIG. 15 is a plot showing a steady-state response (in terms of thermopile output voltage) from a microdevice according to some embodiments the disclosed subject matter in response to constant differential power between the two chambers of the microdevice.
Figure 16:
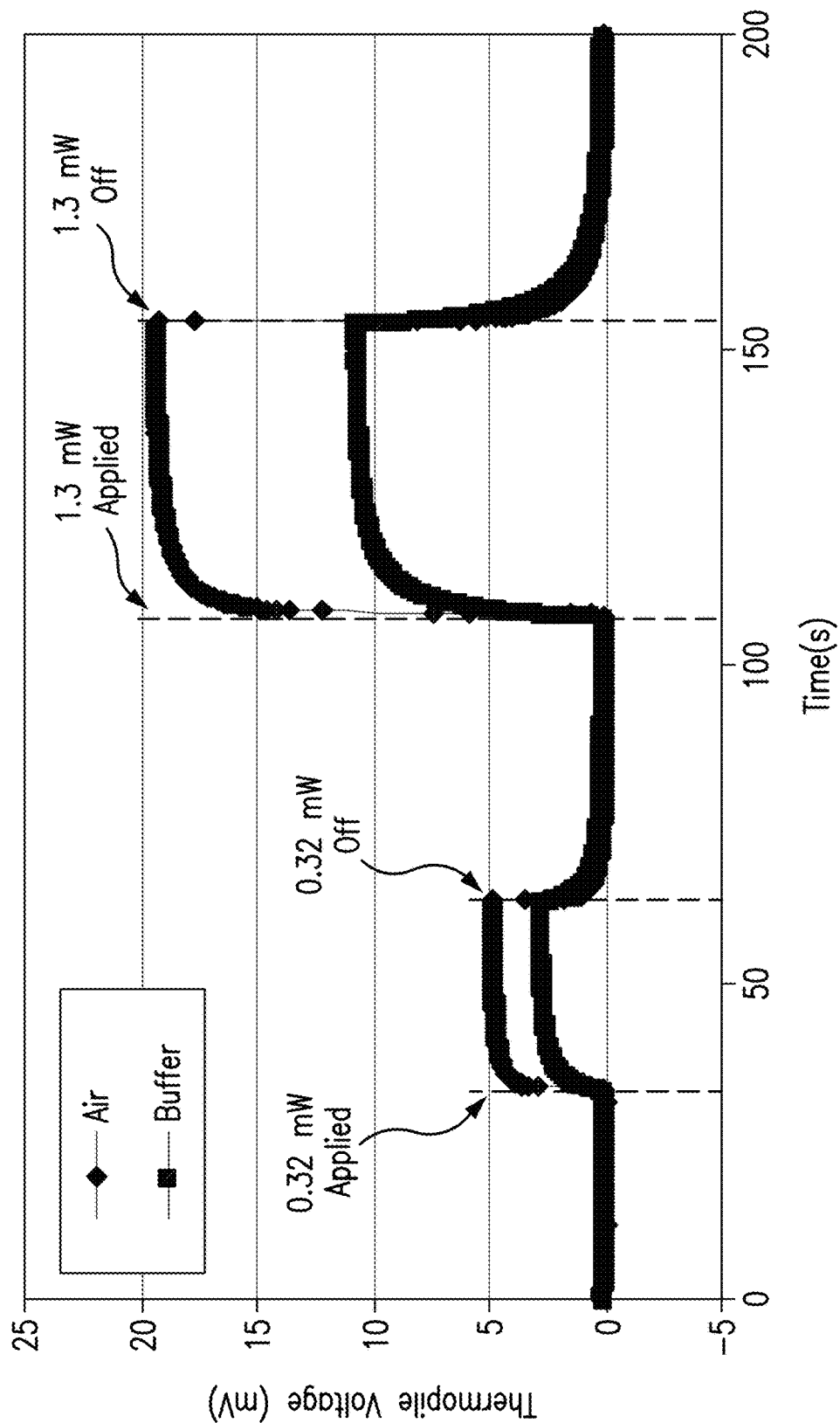
FIG. 16 is a plot showing the transient response of a microdevice according to some embodiments the disclosed subject matter with respect to a step differential power.

The thermopile in the MEMS device was first calibrated, and the results showed that 100-junction thermopile had a sensitivity of 13.0 mV/° C. (FIG. 14), corresponding to a Seebeck coefficient of (per Sb—Bi thermoelectric junction) of approximately 130 µV/° C. The steady-state response of the device to a constant differential power was then measured, and exhibited a highly linear relationship with a DC responsivity of 8.0 mV/mW (FIG. 15). These results were consistent with calibration results from the 50-junction Sb—Bi thermopile in Example 2. Additionally, the transient response of the device was determined. The calorimetric chambers, both of which were filled either with air or with 0.1 M Glycine-HCl buffer (pH 2.5), were subjected to a step differential power (0.32 or 1.30 mW). Results from these measurements are shown in FIG. 16. The dependence of the thermopile voltage on time can be represented by a first order exponential increase. The thermal time constant thus obtained was 0.8 s when the chambers were filled with air, and 2.0 s when they were filled with buffer solution. These values were independent of the applied differential power, and were smaller than conventional AC calorimetric measurements.

Figure 17:
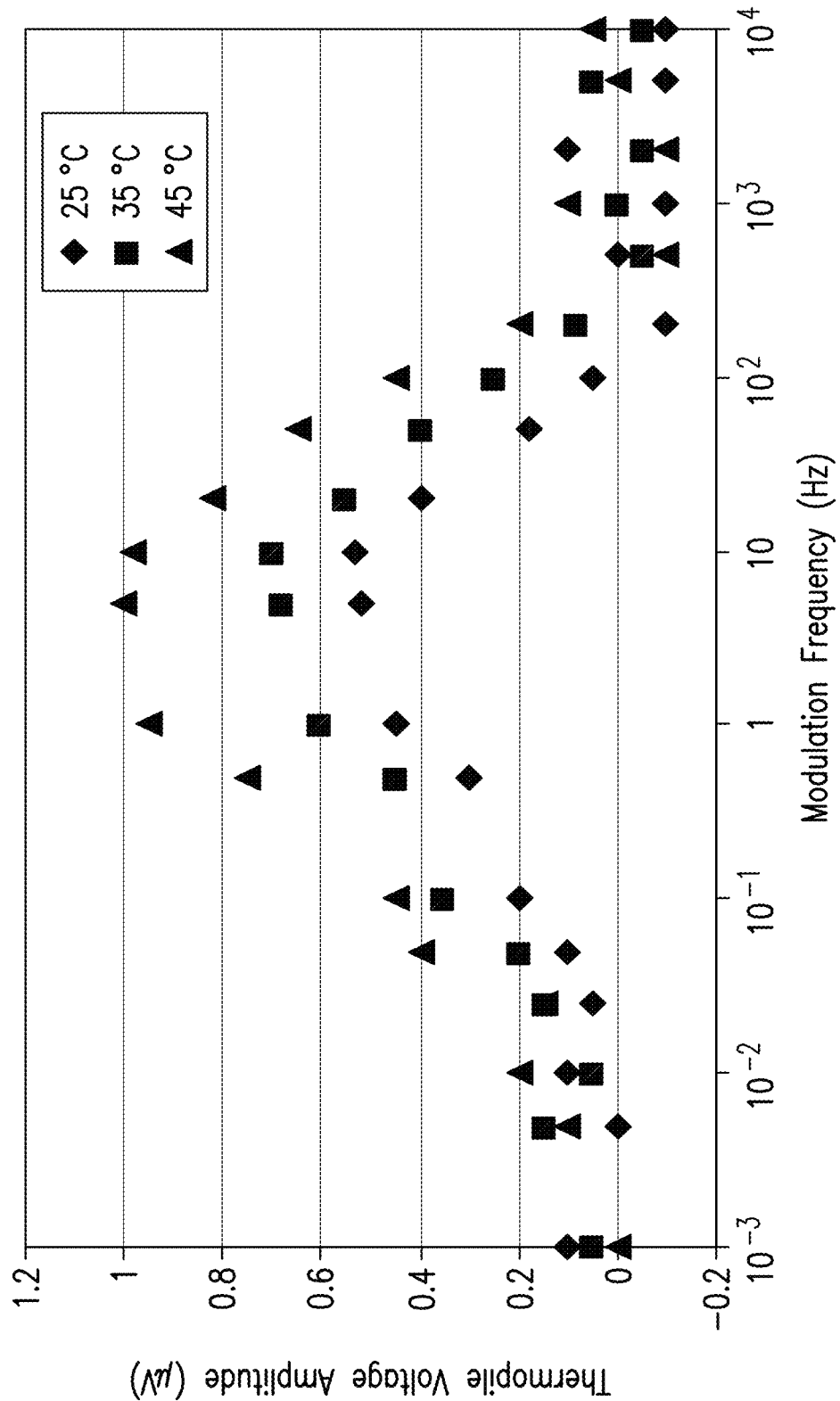
FIG. 17 is a plot showing the frequency dependence of thermopile voltage (baseline subtracted) of a microdevice according to some embodiments the disclosed subject matter, where the sample chamber was filled with lysozyme (20 mg/mL) and the reference chamber was filled with 0.1 M Glycine-HCl buffer (pH 2.5).

Further, the modulation frequency dependence of the device response to the applied differential power was investigated. To better simulate the application for AC-DSC measurement of protein unfolding process, the sample chamber was filled with lysozyme (20 mg/mL, prepared in 0.1 M Glycine-HCl, pH 2.5) as a sample, while the reference chamber was filled with Glycine-HCl buffer. The chambers were maintained at a constant temperature (25, 35, or 45° C.), and subjected to AC heating (voltage amplitude: 1 V). The dependence of the thermopile voltage amplitude on the modulation frequency, corrected by baseline subtraction, is shown in FIG. 17. It can be seen that the thermopile voltage increased with temperature at almost all modulation frequencies, which can be explained by the temperature-dependence of the protein's heat capacity. Also, the device output (and hence sensitivity) appear greatest in a modulation frequency range of 0.5 to 20 Hz (FIG. 17), suggesting a reduced heat loss to the ambient by choice of modulation frequency. Therefore, modulation frequencies in this range were used below in calorimetric measurements of protein unfolding processes, as further described below.

C. AC-DSC Measurements

The MEMS AC-DSC device calibrated above was used to measure the thermal behavior of protein unfolding. Using lysozyme at different concentrations (10 and 20 mg/mL, prepared in 0.1 M Glycine-HCl buffer, pH 2.5) for example, the temperature of the calorimetric chambers was varied from 25 to 82° C. at a rate of 5° C./min in combination with AC modulation via a heating voltage amplitude of 3.5 V at a constant frequency (1, 5, or 10 Hz). The periodic temperature variation resulting from the AC modulation heating had an amplitude of approximately 0.2° C.

Figure 18:
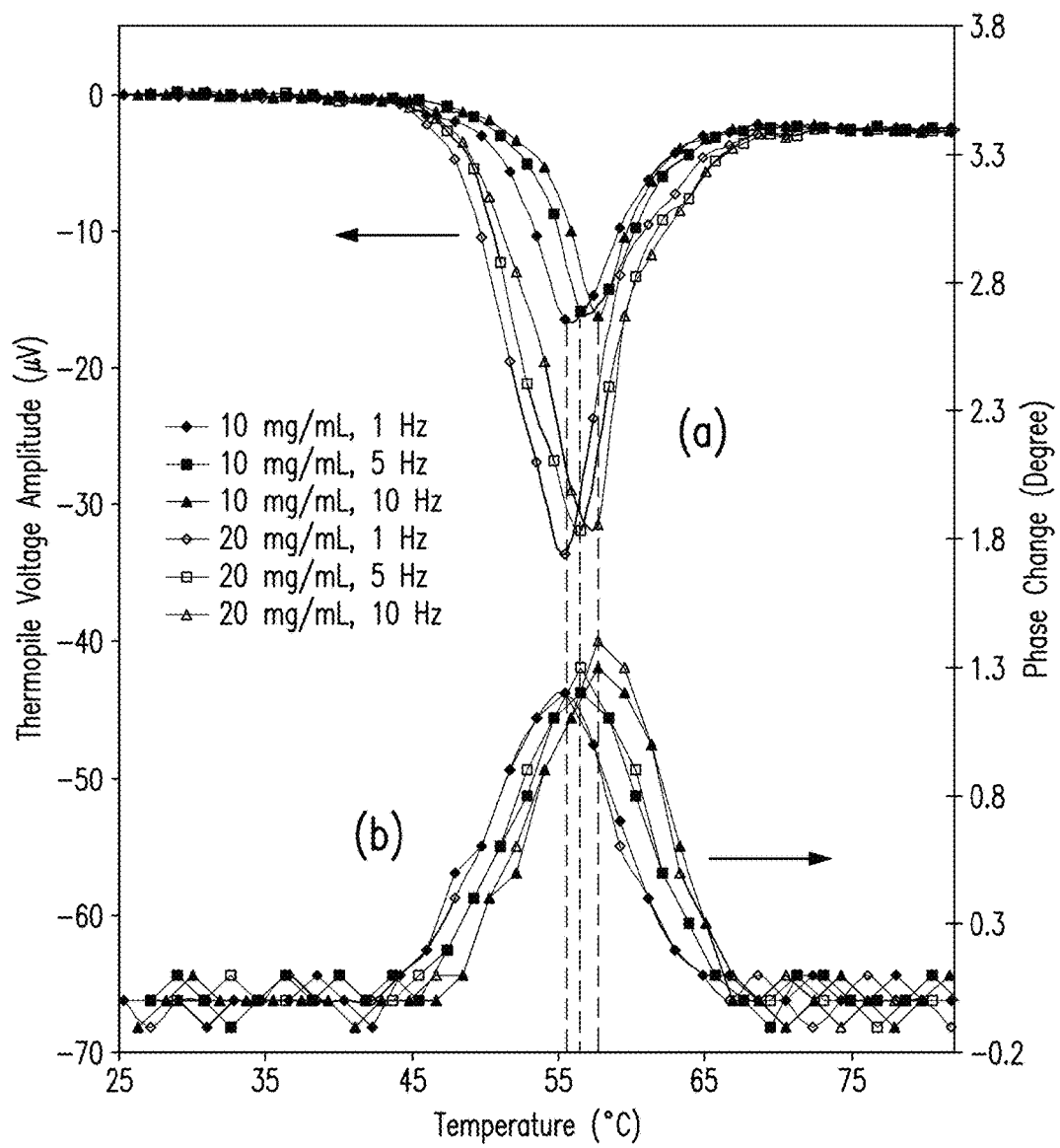
FIGS. 18a and 18b are plots showing changes in (18a) amplitude, and (18b) phase, of the thermopile voltage as a function of temperature during the unfolding of lysozyme at different lysozyme concentrations and AC modulating frequencies, as measured on a microdevice according to some embodiments the disclosed subject matter.

The measured thermopile voltage amplitude (FIG. 18a), again corrected by baseline subtraction, showed a concentration-dependent dip during the unfolding process, consistent with the endothermic nature of protein unfolding. In addition, despite differences in thermopile voltage amplitude for different lysozyme concentrations, the phase of the thermopile voltage (FIG. 18b) had identical changes throughout the unfolding process, which remained unchanged in the native and unfolded states when a two-state protein denaturation model was adopted. Furthermore, both the amplitude and phase changes of the thermopile voltage exhibited clear shifts with the modulation frequency, which could be attributed to the unsynchronized thermal response of the device to AC heating. However, at a fixed protein concentration, the profiles of the thermopile voltage amplitude and phase changes had virtually the same shape at different modulation frequencies, showing the suitability of the frequency choice for the MEMS-based AC-DSC measurements.

Figure 19:
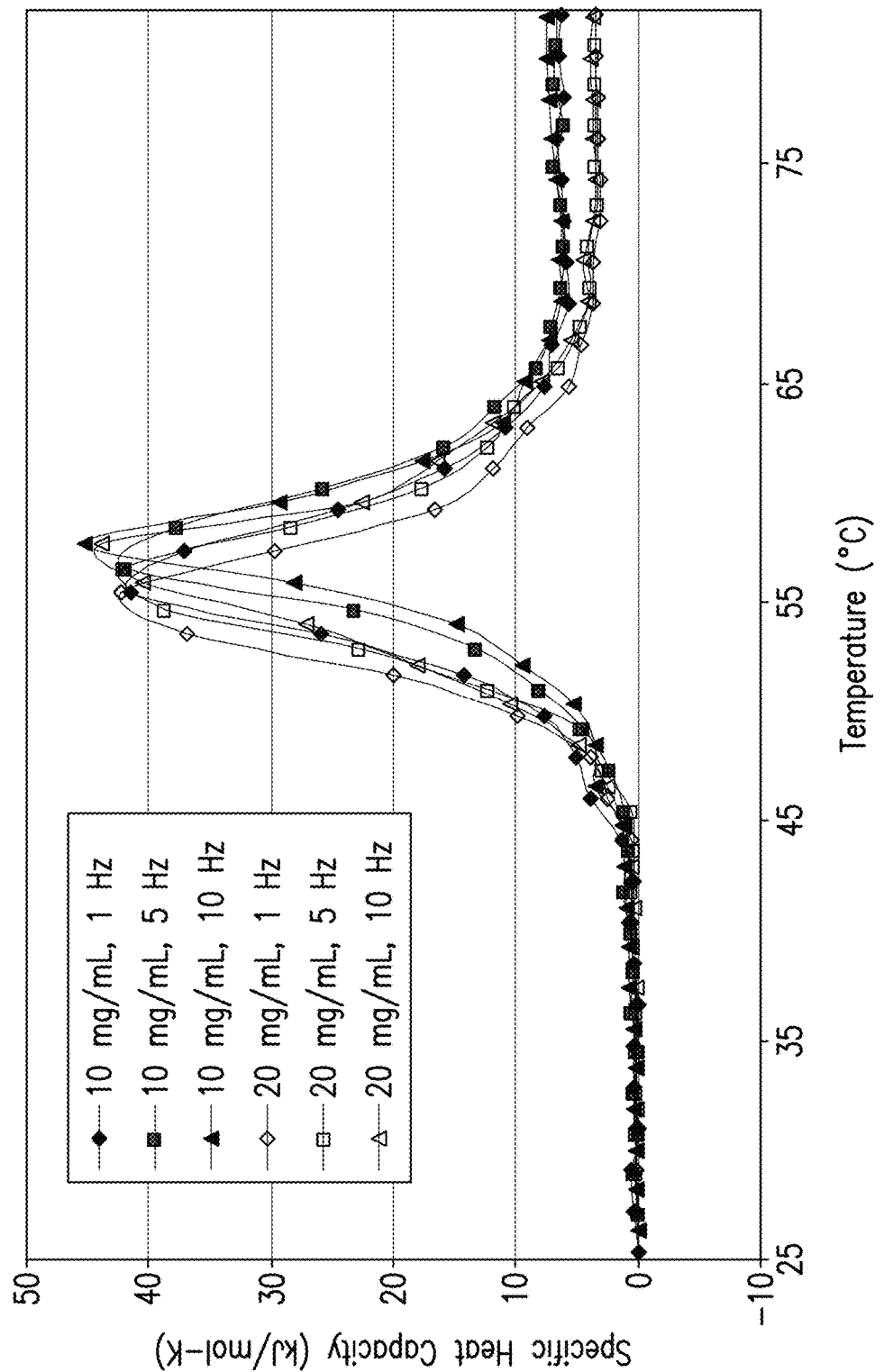
FIG. 19 is a plot showing specific heat capacity of lysozyme as a function of temperature during the unfolding of lysozyme at different lysozyme concentrations and AC modulation frequencies, as measured on a microdevice according to some embodiments the disclosed subject matter.
Figure 20:
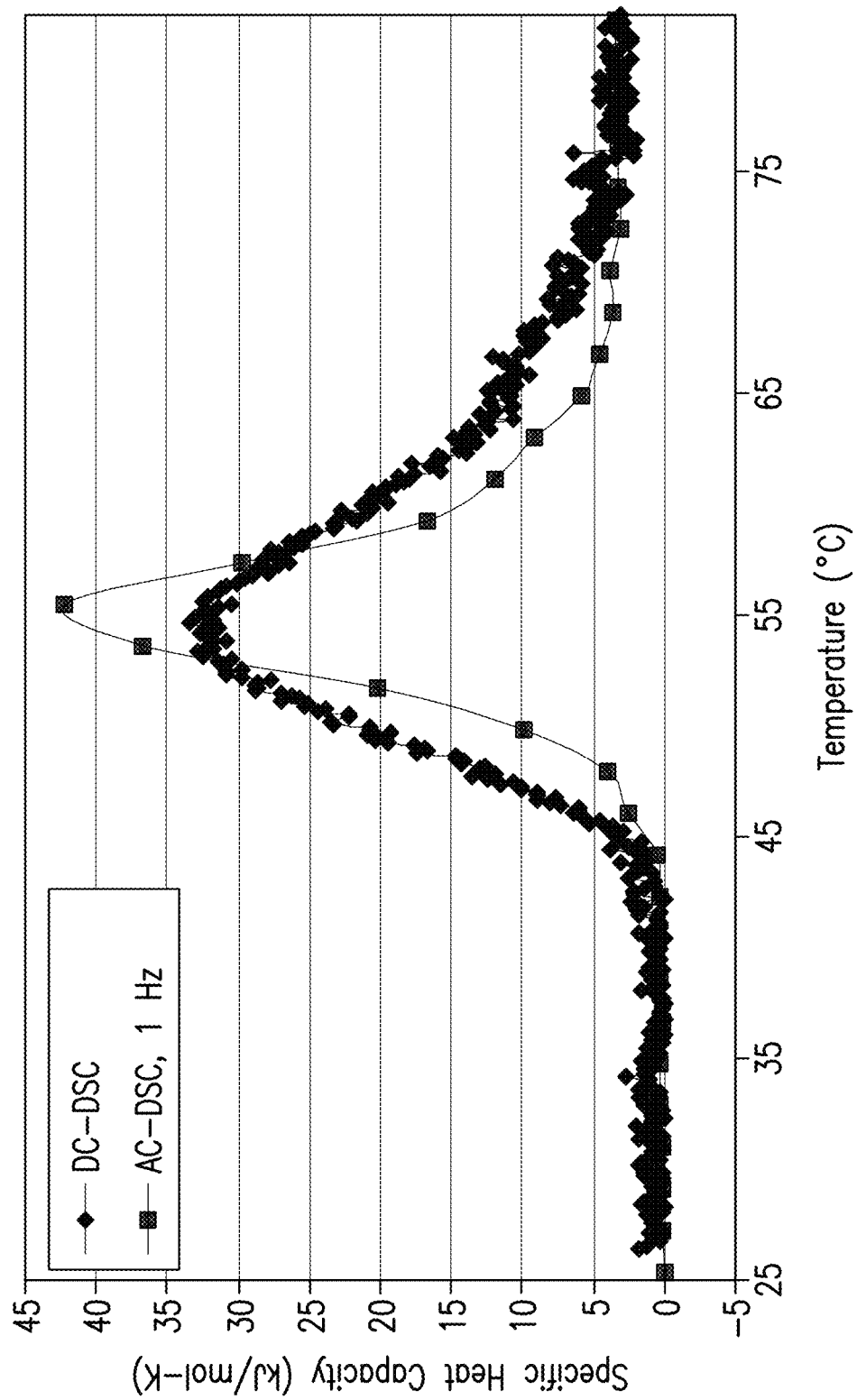
FIG. 20 is a plot showing a comparison between a DC-DSC measurement and an AC-DSC measurement for specific heat capacity of lysozyme during its unfolding process, using a microdevice according to some embodiments the disclosed subject matter.

The apparent melting temperature ($T_m$) of lysozyme during an unfolding process, i.e., the temperature at which the phase change of device output reaches its peak, was found to be in the range of 55-58° C. (FIG. 18), depending on the modulation frequency. Meanwhile, the specific heat capacity (c) of the protein as a function of temperature can be computed from the thermopile voltage amplitude (FIG. 19). It be seen that although there again existed a slight shift in c throughout the unfolding process induced by modulation frequency, the profile shape of c was not influenced by the modulation frequency. Moreover, at each modulation frequency, the calculated value of c does not differ significantly at different protein concentrations (FIG. 19), showing that the AC-DSC measurements were accurate. There was also a difference in the specific heat capacity ($\Delta c$) between the protein's native and unfolded states, which was calculated consistently to be 3.0 kJ/mol·K regardless of the modulation frequency. These results are consistent with established results from DC-DSC characterization. Compared with DC-DSC measurements in the same MEMS device without using temperature modulation (FIG. 20), AC-DSC can offer much reduced noise levels and improved measurement accuracies, and therefore holds the potential to enable characterization of biomolecular interactions at low concentrations Example 4. MEMS-Based Isothermal Titration Calorimetry This Example illustrates the method of performing isothermal titration calorimetric measurement, as described above based on a microdevice disclosed herein.

A. Principle

Consider a solution-phase biochemical reaction $n_1 A + n_2 B \leftrightarrow C + \Delta H$, where A and B are reactants (e.g., a ligand and a sample, respectively) and C is a product. The reaction is accompanied by a change of enthalpy $\Delta H$. In ITC, the ligand can be titrated, or successively added in known aliquots, into the sample, while the reaction heat is measured. This data can then used to determine the thermodynamic properties of the reaction, including the equilibrium binding constant $K_B=[C]/[A][B]$ (the square brackets denote the equilibrium concentration of the species), stoichiometry $N=n_1/n_2$, and enthalpy change ($\Delta H$).

B. Device Setup and Calibration

Figure 21A:
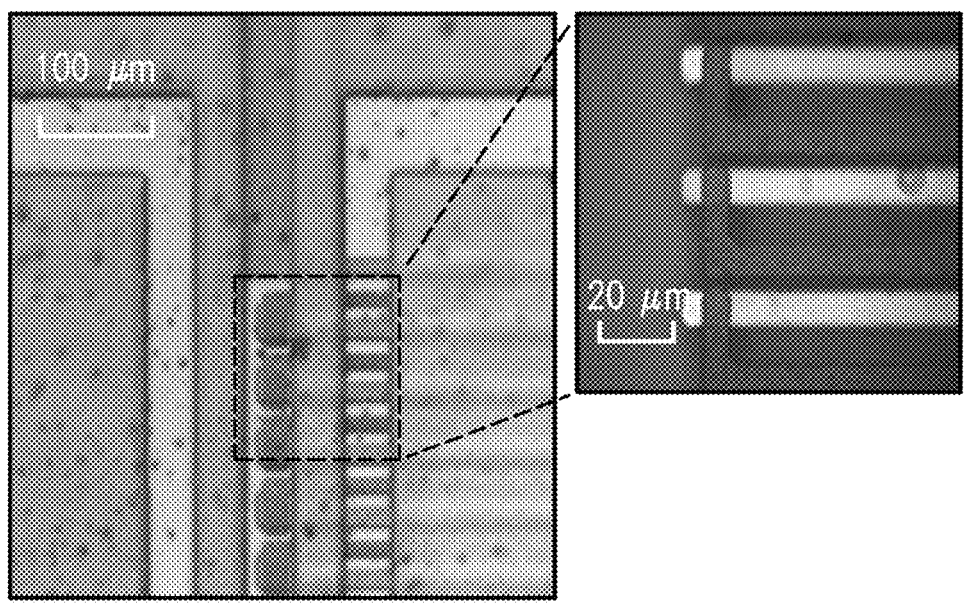
FIG. 21 are images of certain elements of a microdevice for isothermal titration calorimetry according to some embodiments of the disclosed subject matter.
Figure 21B:
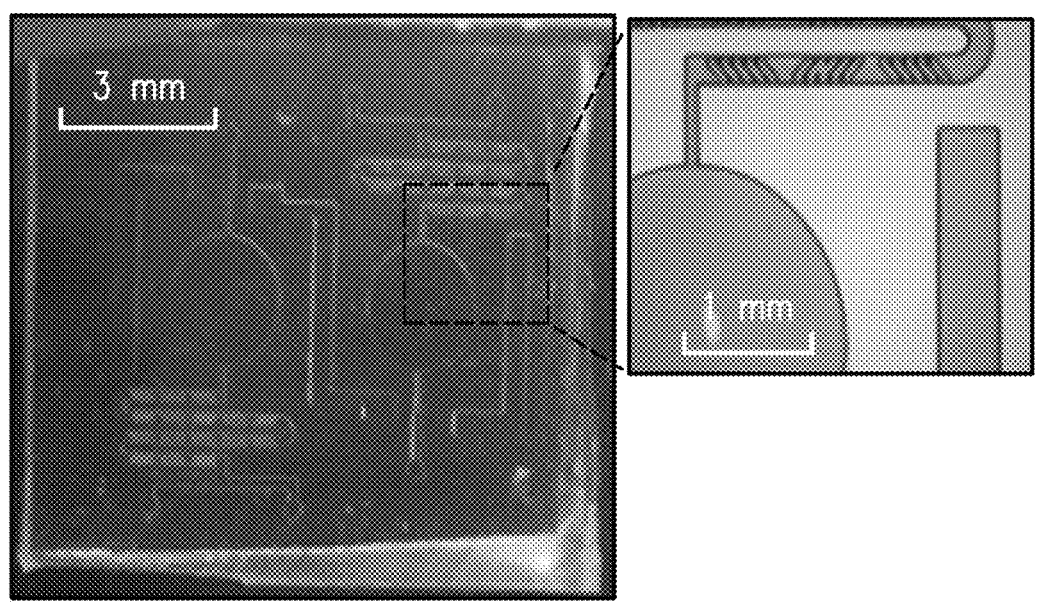
Figure 22:
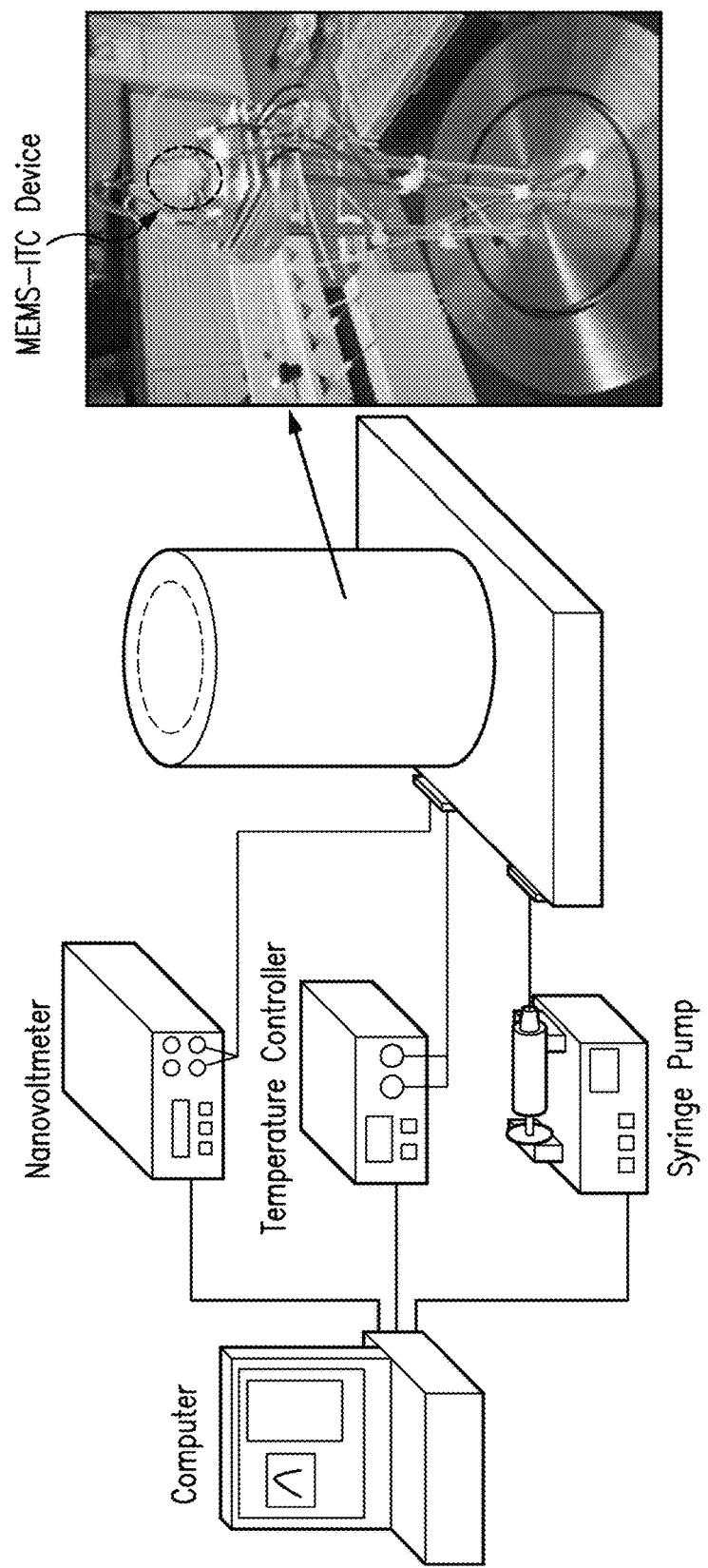
FIG. 22 is a schematic diagram showing the experimental setup for isothermal titration calorimetry according to some embodiments of the disclosed subject matter.
Figure 23A:
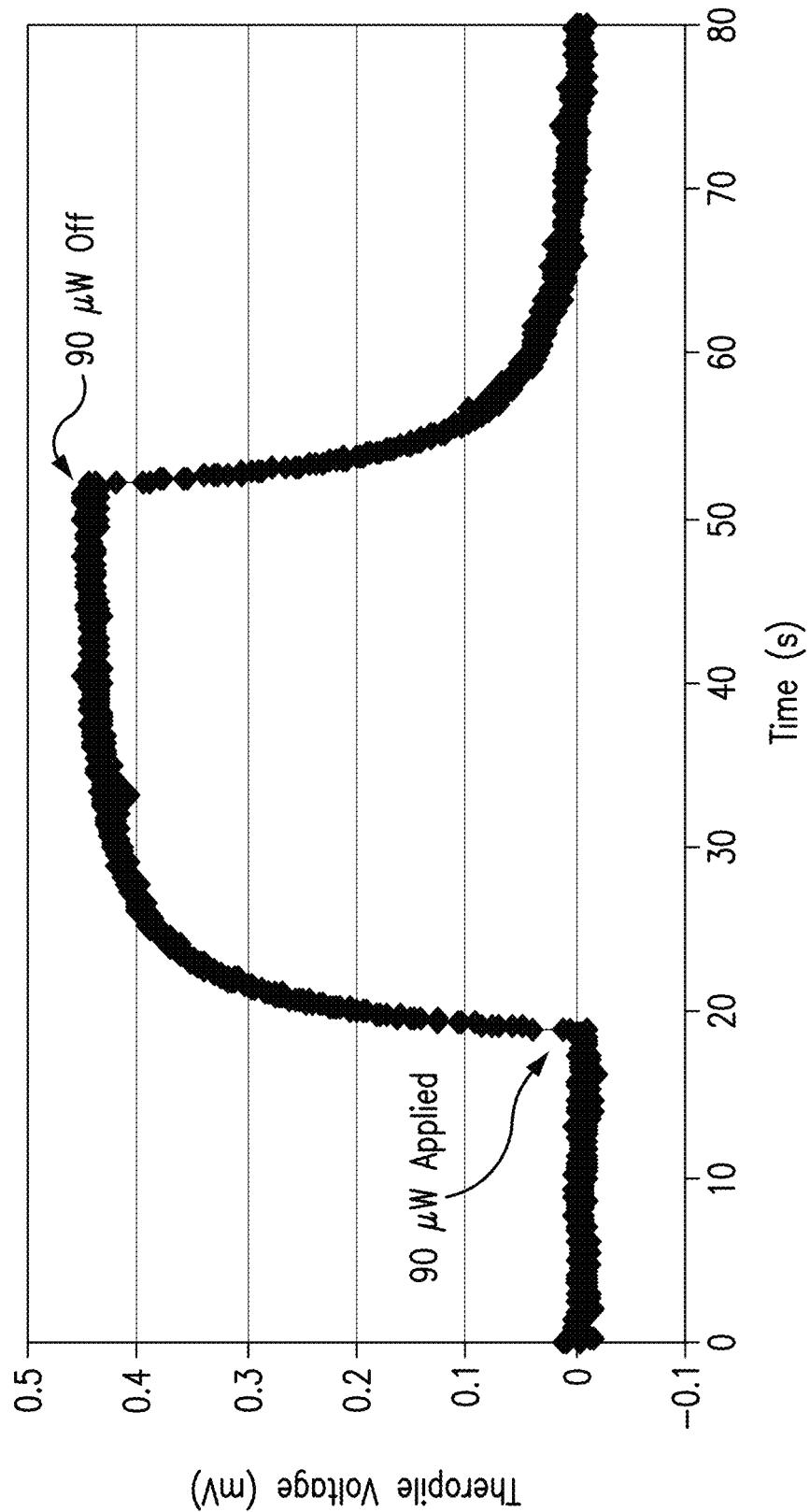
FIGS. 23a and 23b are plots showing calibration results of a microdevice according to some embodiments of the disclosed subject matter for performing isothermal titration calorimetry: transient response to a step differential power (23a), and steady-state response to a constant differential power (23b).
Figure 23B:
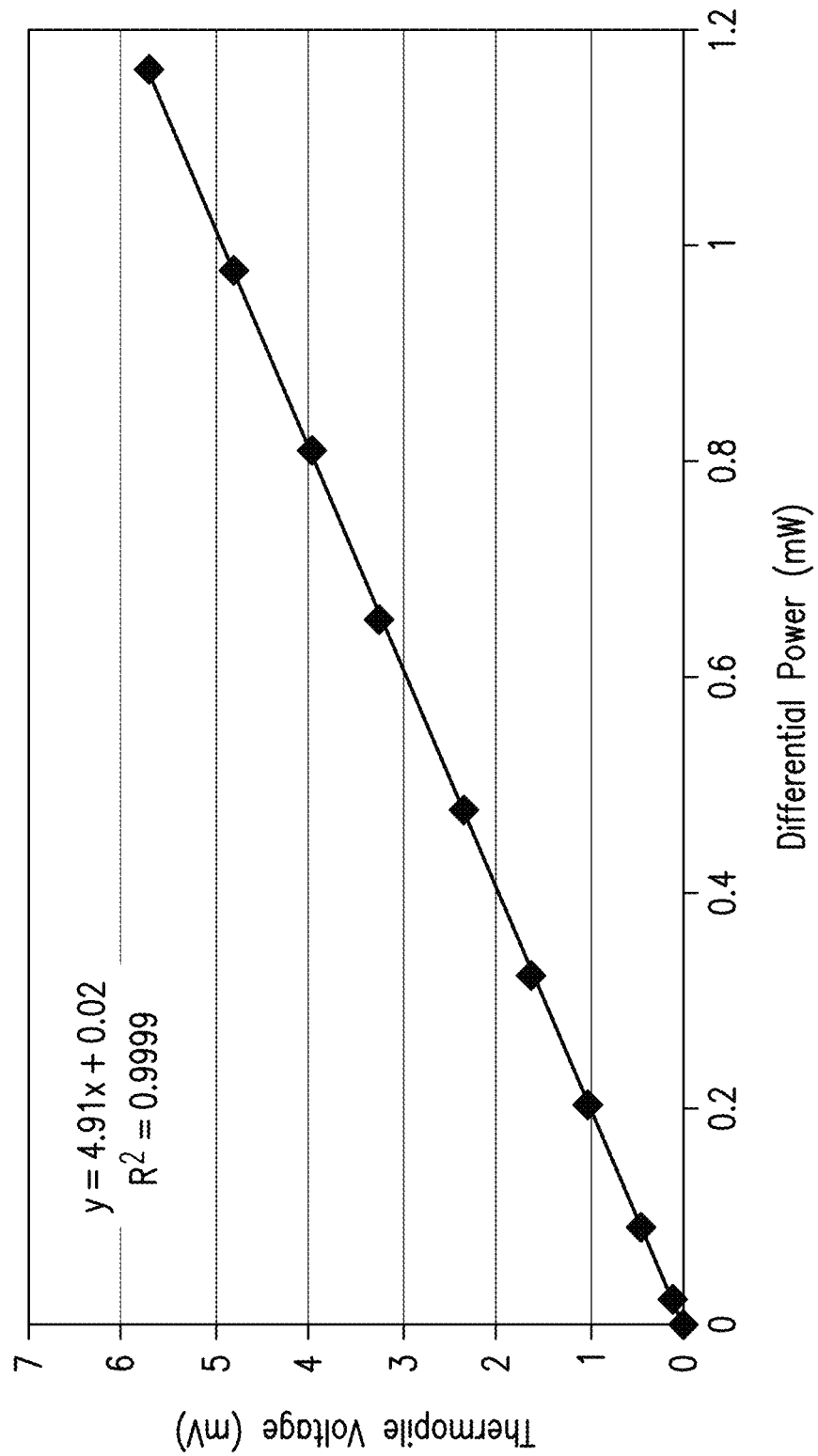

The MEMS-ITC device as schematically shown in FIG. 4 was used. Briefly, the device integrates two identical polydimethylsiloxane (PDMS) microchambers each (1 μL) situated on a freestanding polyimide thin film substrate and surrounded by air cavities for thermal isolation. The chambers are integrated with an antimony-bismuth (Sb—Bi) thermopile and connected to the inlets through an introduction channel which includes a passive chaotic mixer having herringbone-shaped ridges in the ceiling of a serpentine channel to generate a chaotic flow pattern that induces mixing of the incoming liquid streams. Some of the features of the MEMS-ITC device used were shown in FIG. 21. For ITC measurements, the two reactants, herein referred to as the ligand and sample for purpose of illustration, were introduced into the device and first mixed in the introduction channel, and then enter the sample calorimetric chamber, where the reaction is completed. In the meantime, the sample and pure buffer (devoid of the ligand) were also introduced into the device, becoming mixed before entering the reference calorimetric chamber. The differential temperature between the chambers were measured using the integrated thermopile, and was used to determine the thermal power from the reaction, from which the thermodynamic reaction parameters were calculated. The device was placed in a low-noise, temperature-controlled thermal enclosure (FIG. 22) where the thermopile output was measured. The sample and ligand were introduced using syringe pumps. Calibration experiments indicated that the device had a thermal time constant of 1.5 s with a linear steady-state thermal response (responsivity: 4.9 mV/mW) (FIG. 23).

C. ITC Measurement

Figure 24:
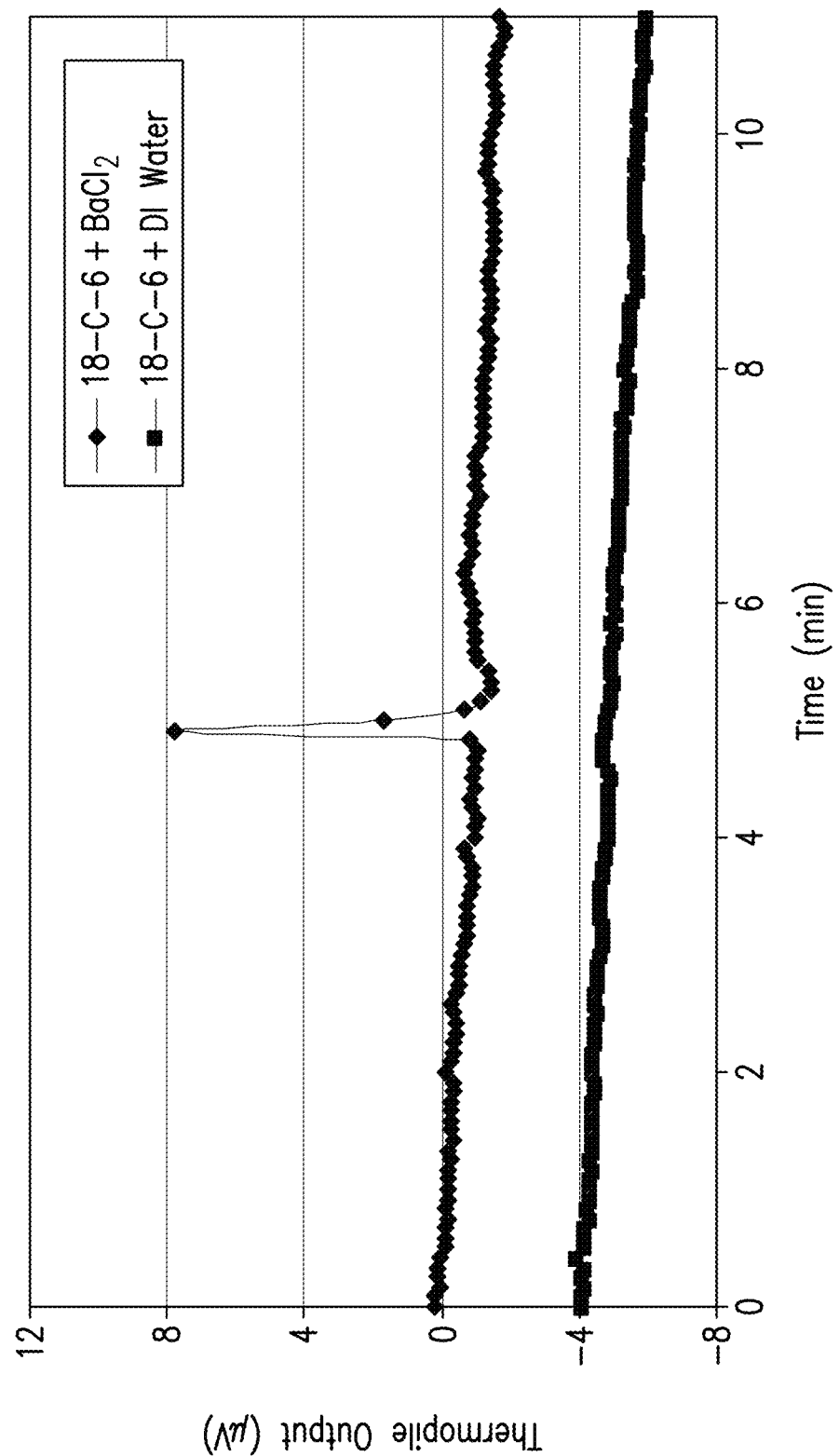
FIG. 24 is a plot showing a time-resolved output of a microdevice according to some embodiments of the disclosed subject matter upon introduction of 5 mM 18-C-6 and 4 mM $BaCl_2$ (each 0.5 µL), compared with measurement of 5 mM 18-C-6 titrated by DI water (plotted with a 4 µV offset for clarity).
Figure 25A:
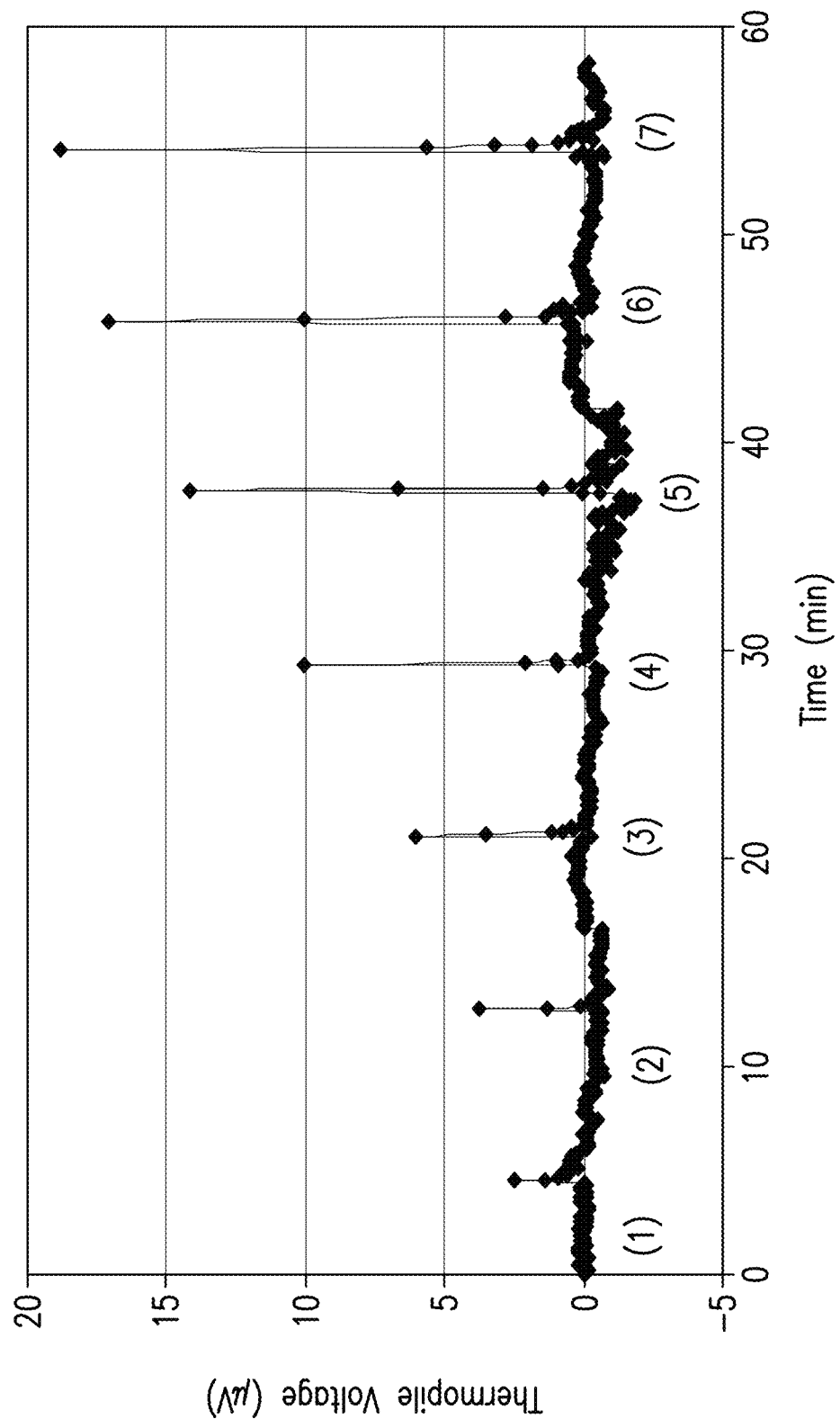
FIGS. 25a and 25b are plots for the output of a microdevice according to some embodiments of the disclosed subject matter in the isothermal titration calorimetric measurement of the binding of 5 mM 18-C-6 and $BaCl_2$ at continuous injections with a series of molar ratios (25a); and calculated heat of the binding of 18-C-6 and $BaCl_2$ as a function of molar ratio. The fitted curve is based on a one-site binding model.
Figure 25B:
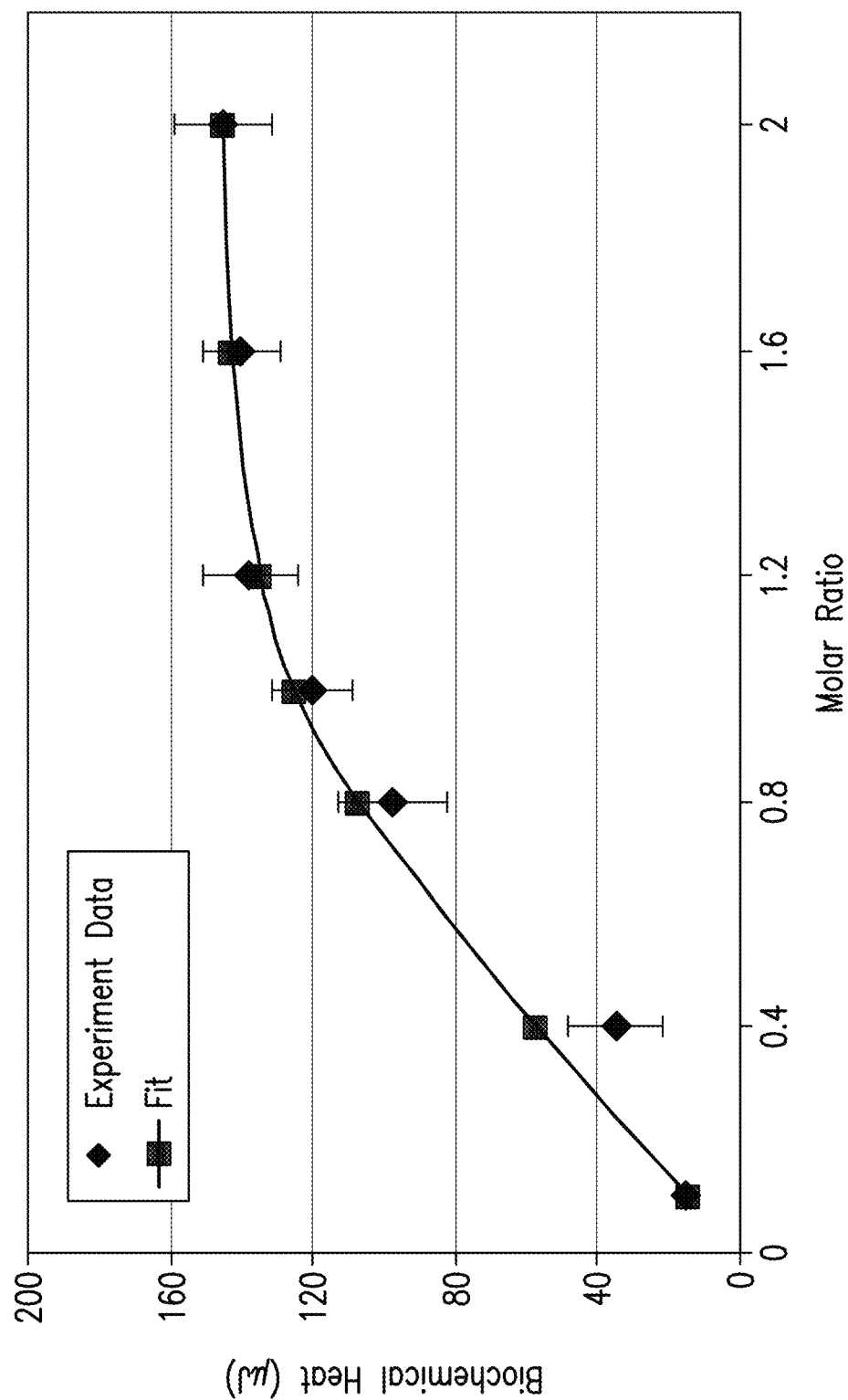
Figure 26:
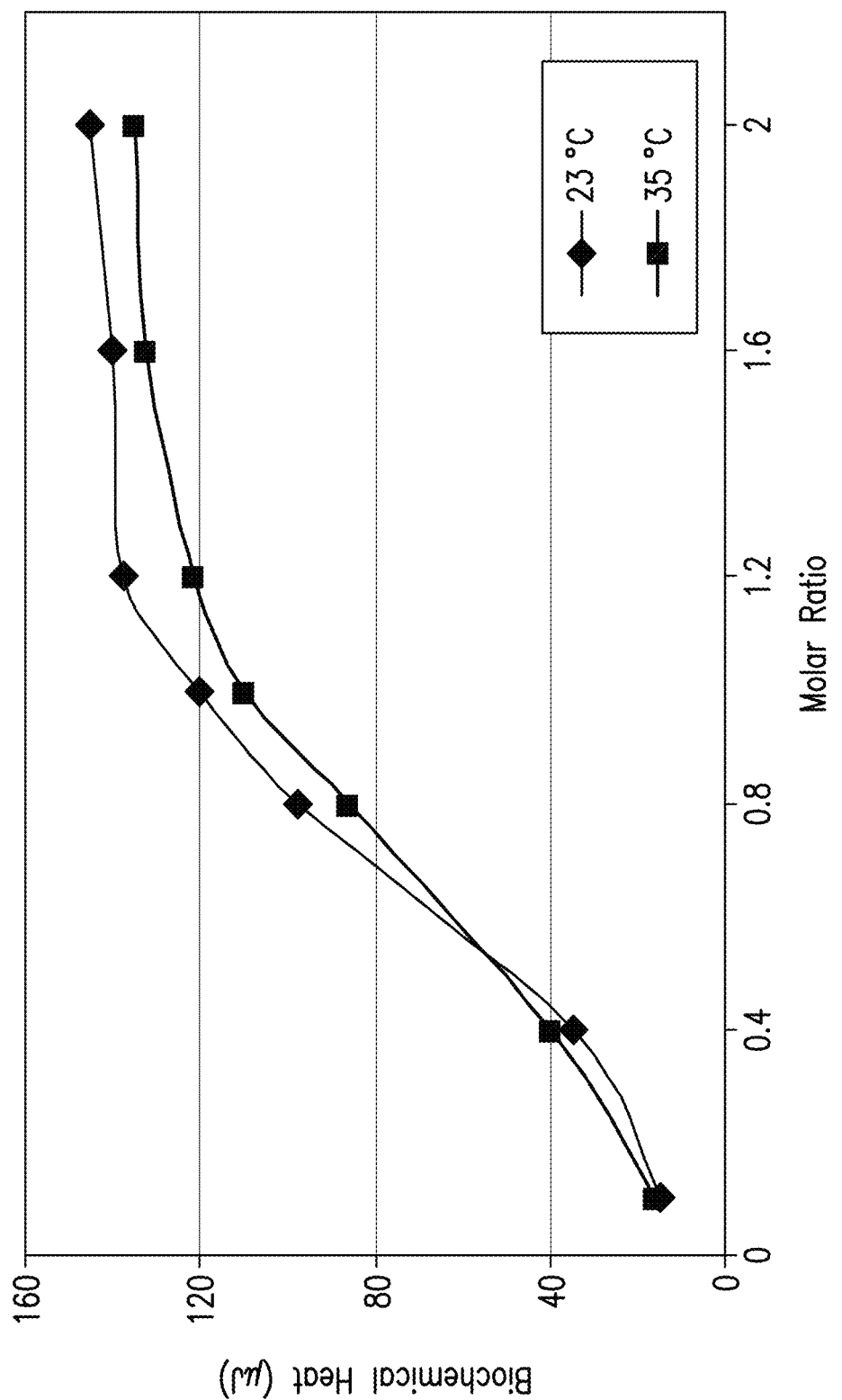
FIG. 26 is a plot showing the biochemical heat of binding of 18-C-6 and $BaCl_2$ as a function of molar ratio at temperatures of 23 and 35° C., as calculated from the output of a microdevice according to some embodiments of the disclosed subject matter.

The device was used for ITC measurements of a model reaction system consisting of 18-C-6 and $BaCl_2$. The time-resolved device output exhibited a reaction-specific spike (FIG. 24) upon introduction of 5 mM $BaCl_2$ and 4 mM 18-C-6 (each 0.5 μL) with no appreciable delay, indicating full mixing of the reactants. Using titrations with the molar ratio ($BaCl_2$/18-C-6) varying from 0.1 to 2 ((1) 0.1, (2) 0.4, (3) 0.8, (4) 1.0, (5) 1.2, (6) 1.6, (7) 2.0), the baseline-subtracted device output demonstrated spikes consistent with the titration reactions, and allowed construction of a binding isotherm (FIG. 25). ITC measurements were performed at 23 and 35° C. (FIG. 26), and the resulting isotherms were used to compute $K_B$ and $\Delta H$, which decrease with temperature (See Table 1 below). These results demonstrated that the MEMS-ITC device as disclosed affords detectable sample concentrations approaching those of conventional instruments (ca. 1 mM) with roughly three orders of magnitude reduction in volume.

TABLE 1

Temperature-dependent thermodynamic properties: the stoichiometry (N), binding affinity (KB) and enthalpy change (H), of the binding of 18-C-6 and BaCl2 at two temperatures

| Temperature (° C.) | N | $K_B$ (M$^{-1}$) | $\Delta H$ (kJ/mol) |
|---|---|---|---|
| 23 | 1.0 | $6.0 \times 10^{-3}$ | 30.0 |
| 35 | 1.05 | $2.8 \times 10^{-3}$ | 27.8 |

Example 5. MEMS-Based Isothermal Calorimetry

Chaotic mixers and calorimetric chambers were fabricated in a single sheet using PDMS replica technique based on multiple-layered SU-8 molding. The microfabricated device integrated a 50-junction Sb—Bi thermopile and two 0.75 μL calorimetric chambers with a center-to-center separation of 4 m. The calorimetric chambers had a cylindrical shape with a height of 150 μm and a diameter of 2.5 mm. The chaotic mixers were serpentine microchannels (width: 200 μm, height: 150 μm, length: approximately 15 mm) with herringbone-shaped ridges on the ceiling with each having a width of 40 μm, a height of 50 μm, an orientation angle of 60° to the channel sidewall, and an edge-to-edge distance between adjacent ridges of 30 μm. The nominal resistances of the integrated resistive microheaters and temperature sensors were 40Ω and 55Ω, respectively.

To test the MEMS-IT device, a thermal enclosure was custom-built to house the device to shield the thermal disturbance from ambient, as well as provide uniform temperature control to the solutions loaded in the device. The thermal enclosure was improved with additional thermal isolation by suspending the sample stage from the base, vibration isolation by enhanced base mass and rubber buffering layer, and multiple-ports microfluidic feedthrough to the device. The temperature control of the thermal enclosure was implemented by a commercial temperature controller (Lakeshore Model 331). The device was first packaged with electrical interconnection wires and fluidic interconnection tubes before it was situated on the sample stage inside the thermal enclosure.

The on-chip microheaters, used for device calibration, were driven by a DC power supply (Agilent E3631A) and generated a constant differential heating power in the calorimetric chambers. The on-chip temperature sensors, used for in-situ temperature monitoring of the calorimetric chambers, were interrogated by a digital multimeter (Agilent 3410A). The thermopile output voltage, which is proportional to the differential temperature between the chambers, was measured by a nanovoltmeter (Agilent 34420A). The temperature monitoring of the calorimetric chambers and thermoelectric measurements were automated using a personal computer via a Lab VIEW-based program. The biological sample and buffer solutions were degassed with a vacuum chamber built in-house, metered introduced into the MEMS-ITC device using a multiple-injections syringe pump (KD Scientific, KDS 220).

The device was first calibrated by measuring its steady-state and transient response to differential power generated by on-chip microheaters. Before ITC measurements, the baseline in device output, i.e., the thermopile output voltage in the absence of reaction, was measured with introduction of sample and buffer solutions to both calorimetric chambers. During ITC measurements, the thermal enclosure provided a controlled reaction temperature while the thermopile output, indicative of the differential bio-thermal power, was detected in real time, as well as the integrated micro-temperature sensor to monitor the temperatures of the calorimetric chambers. The volume of ligand and sample was fixed at 0.5 µL for each injection, while the molar ratio was adjusted by changing the concentration of ligand to be injected. The baseline in device output was always subtracted from the measurement signal for determination of thermodynamic properties of biomolecules.

The thermal time constant of the MEMS-ITC device was calibrated by applying a step differential power of 90 µW initially and then turned it off once the device output reached its equilibrium. The device output voltage was found to fit the first-order exponential growth and decay functions upon the application and removal of the differential power, respectively, from which the thermal time constant was determined to be approximately 1.5 s. In addition, the steady-state response of the device was calibrated to varying differential power, and a linear relationship showing a constant thermoelectric sensitivity of S=4.9 mV/mW was observed. The device's sensitivity was also calibrated at controller temperatures (provided by the thermal enclosure) from 20° C. to 45° C., and it was found that it remained almost unchanged with a relative standard deviation of less than 3%.

Figure 30:
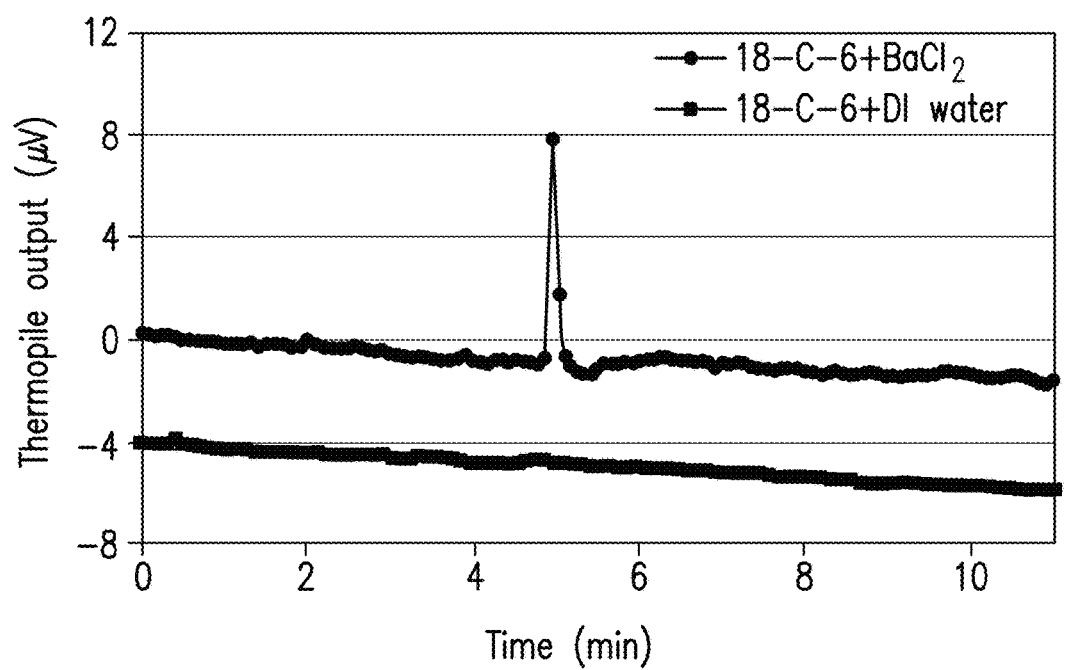
FIG. 30 illustrates a comparison of measurements of the time-resolved thermopile voltage upon introduction of 4 mM $BaCl_2$ and 5 mM 18-C-6 (each 0.5 µL) in the reaction chamber, and the signal upon introduction of sterile water and 5 mM 18-C-6 (also each 0.5 µL) in accordance with an embodiment of the disclosed subject matter.

The baseline stability and detection specificity was then tested using a standard chemical reaction of 18-Crown-6 (18-C-6) and barium chloride ($BaCl_2$) both prepared in sterile water (all chemicals from Sigma Aldrich). Using a flow rate of 50 µL/min, the solutions were injected into the calorimetric chambers within 1 s. Using a data acquisition rate of 2 $s^{-1}$ to monitor the device output in real time, no appreciable delay was observed after injection, indicating full mixing of the reactants. A comparison of the time-resolved thermopile voltage upon introduction of 4 mM $BaCl_2$ and 5 mM 18-C-6 (each 0.5 µL) in the reaction chamber, and the signal upon introduction of sterile water and 5 mM 18-C-6 (also each 0.5 µL) is shown in FIG. 30. For both measurements, the reference chamber was injected with sterile water and 5 mM 18-C-6, and a data acquisition rate of 0.2 $s^{-1}$ was used due to instrument configuration for lower background noise. The device exhibited a stable baseline throughout the measurements and a reaction-specific spike attributable to the exothermic nature of the binding between 18-C-6 and $BaCl_2$. The reaction completed in approximately 20-30 s, during which any interference from solution injection and mixing were generally negligible.

Figure 31:
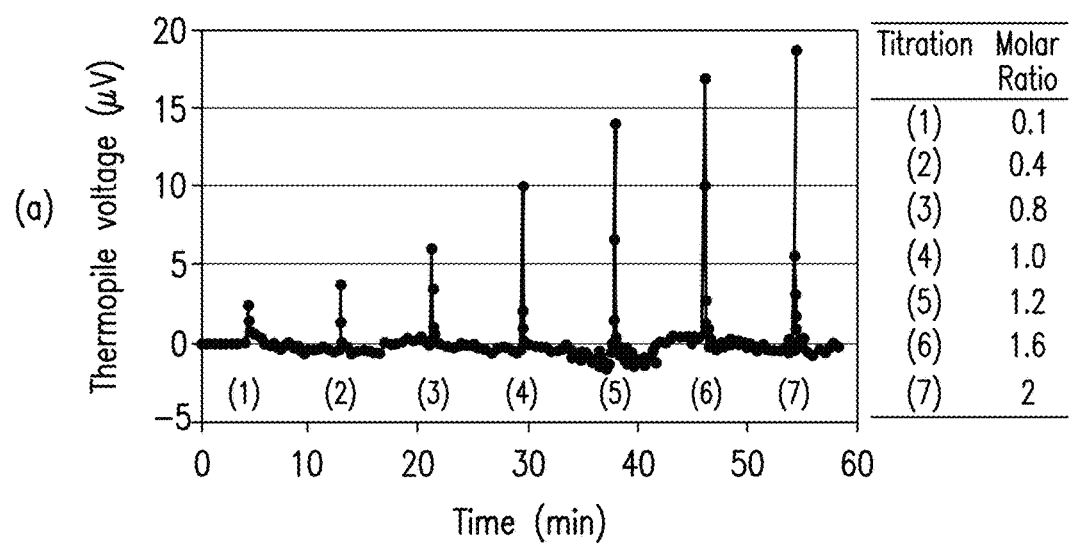
FIG. 31 illustrates the baseline-subtracted device output of a device for characterizing biochemical reactions in accordance with one embodiment of the disclosed subject matter.

The MEMS-ITC device was then used to characterize biomolecular interactions. The $BaCl_2$-18-C-6 reaction was used to validate the ITC measurements. By varying the molar mass ration ($M_{BaCl_2}$/$M_{18-C-6}$) from 0.1 to 2, the baseline-subtracted device output demonstrated spikes consistent with the titration reactions. The baseline-subtracted device output is shown in FIG. 31. Rather than measuring the heat evolved with the addition of several aliquots of $BaCl_2$ to a single sample of 18-C-6 as performed in commercial ITC instruments, the ITC experiment was performed at discrete measurements each with a definite concentration of $BaCl_2$ (0.5-10 mM) and a fixed concentration of 18-C-6 (5 mM). Each measurement was completed in approximately 5 min.

The thermopile voltage was the used to calculate the bio-thermal power based on Equation 1. The bio-thermal power was then used to calculate the reaction heat by integral of the biothermal power during the process.

Figure 32:
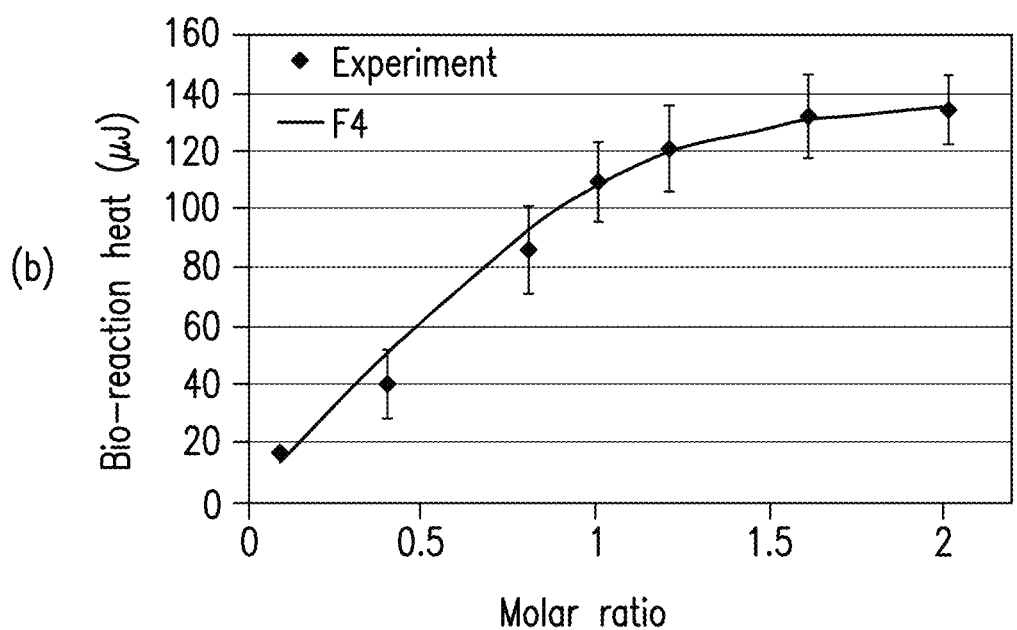
FIG. 32 illustrates the calculated reaction heat derived from the output voltage measurements in accordance with one embodiment of the disclosed subject matter.

The binding isotherm of the reaction of 18-C-6 and $BaCl_2$, as well as the fitted curve, is shown in FIG. 32, with error bars representing the standard deviation from three measurements a each molar ratio. Note that for this specific BaCl2-18-C-6 system, the device affords detectable sample concentrations approaching those of convention instruments (ca. 1 mM) with roughly three orders of magnitude reduction in volume.

ITC measurements were performed of the biological reaction of 18-C-6 and BaCl2 at controlled temperatures of 23° C. and 35° C., and the resulting binding isotherms were used to compute the temperature-dependent thermodynamic properties of N, $K_B$, and ΔH. In particular, as temperature increases from 23° C. to 35° C., N slightly increases from 1.00 to 1.05, while $K_B$ decreases from approximately 6.0× $10^{-3}$ to 2.0×$10^{-3}$ $M^{-1}$ and ΔH decreases from 30.0 o 27.8 kJ/mol, showing a trend of slightly weaker binding with temperature. These properties and their temperature dependence obtained by suitable measurements agree reasonably with published data using commercial calorimeters as shown in FIG. 33.

Figure 34:
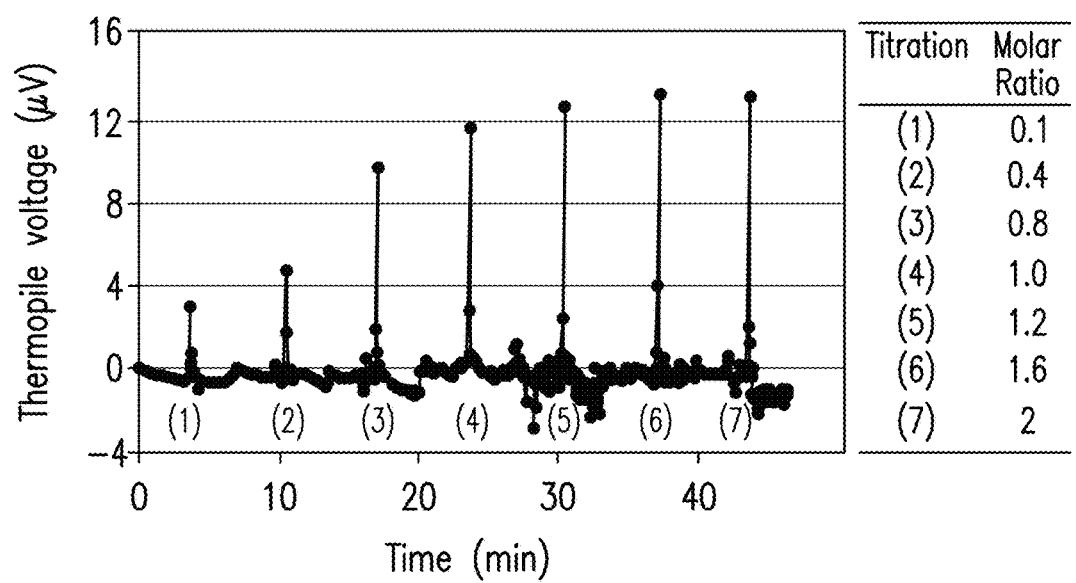
FIG. 34 illustrates device output exhibited titration-dependent spikes in correspondence to the molar ratio at varying molar ratios in accordance with an embodiment of the disclosed subject matter.

The MEMS-ITC device was further applied for characterization of biomolecular interactions, e.g., ligand-protein binding, using a demonstrative system of cytidine 2'-monophosphate (2'CMP) and ribonuclease A (RNase A). 2'CMP is known as a strong inhibitor of substrates that bind to the active site of RNase A. Both reagents were prepared in 50 mM potassium acetate buffer, pH 5.5. Similarly, at varying molar rations (2'CMP/RNase A) from 0.1 to 2, the device output exhibited titration-dependent spikes in correspondence to the molar ratio as shown in FIG. 34. ITC measurements of 2'CMP-RNase A binding at controlled temperatures of 23° C. and 35° C. with error bars from three measurements at each molar ration were also performed. In turn, the temperature-dependent thermodynamic properties associated with this biomolecular interaction were determined from fitting the experimental data to the described model in Equation 3. The results again agreed reasonably with published data using commercial ITC instruments as shown in FIG. 35. For 2'CMP-RNase A interaction, the reasonably detectable concentration of RNase A can be as low as 2 mM. These results demonstrate the utility of this MEMS-ITC device for efficient characterization of a wide variety of biomolecular interactions.

Example 6. Polymer-Based MEMS Differential Scanning Calorimeter

The polyimide film which was used as a substrate was purchased from DuPont (Kapton® 50HN, 12.5 µm thick). The fabrication began with the reversible binding of the substrate to a silicon wafer carrier by a spin-coated poly (dimethylsiloxane) (PDMS) adhesive layer (20 µm). After fully curing this PDMS adhesion layer, Sb and Bi (40 µm wide, 2 mm long, 0.5 and 1 µm thick, respectively) were thermally evaporated and patterned on the substrate using a standard lift-off process to form a 400-junction thermopile, which was then passivated with a spin-coated polyimide thin layer (1.5 µm). Subsequently, a chromium/gold thin film (5/150 nm) was deposited and patterned to define the on-chip temperature sensor, which had a nominal resistance of 55Ω, and then was passivated with another intermediate layer of polyimide-PDMS blend which also served as the adhesion layer of the PDMS microfluidic structure. The fabricated devices were mechanically released from the substrate, and the PDMS binding layer was peeled off so that the silicon carrier can be saved for reuse. In parallel, serpentine microfluidic channels (width: 200 µm, height: 200 µm, length: 25 mm; volume: 1 µL) were fabricated of PDMS via soft lithography. The released substrate was then bonded to the microfluidic structure via oxygen plasma (100 W 3 s).

The packaged polymer MEMS DSC device was placed in a custom-built thermal enclosure consisting of a metal enclosure cap surrounding an aluminum stage on which the device was placed. The thermal enclosure offered additional thermal isolation of the DSC devices from ambient temperature aimed to reduce environmental noise. In addition, the enclosure provided an environment in which the sample and reference solutions in the device were at a sufficiently uniform temperature, which was scanned at a specified rate. Multiple Peltier devices (Melcor UT15-12-40-F2 were located underneath the device stage to add heat to or remove heat from the device while the temperature was precisely scanned with a lakeshore temperature controller (Lakeshore model 311). The temperature of the sample and reference channels was controlled in closed loop by adjusting the voltage applied to the Peltier devices according to the feedback from the temperature sensors mounted on the metal stage based on a proportional-integral-derivative algorithm. The on-chip temperature sensor, calibrated before use, was measured by a digital multimeter (Agilent 34410A), provides in situ temperature monitoring. The thermopile output voltage was measured by a nano-voltmeter (Agilent 34420A). At any instant during DSC measurements, this allowed the biomolecules in the sample solution to experience a uniform temperature, which was accurately obtained by on-chip temperature sensors. Thus, together with the determination of the differential power by the thermopile, the MEMS device in this experimental setup could achieve accurate DSC measurements of biomolecules.

Lysozyme, used as the targeted sample biomolecule, was purchased from Sigma Aldrich (lyophilized powder, protein ≥90%) and dissolved in 0.1-M glycine-HCL buffer (pH 2.5). The sample solutions and buffer were degassed overnight in a vacuum chamber built in-house, metered with Micropipettes, and introduced by a syringe pump (New Era Pump Systems, Inc., NE-1000) before the DSC measurements.

Before the polymer DSC device was used to characterize target biomolecules, liquids with well-established heat capacities were chosen to calibrate the MEMS DSC device. Water and glycerol were used in calibration for their relatively high boiling temperatures while environmental disturbances were minimized by placing the device inside of the thermal enclosure. The thermoelectric and resistive measurements were automated through a LabVIEW-based program. After calibration, the device was thoroughly washed with buffer and deionized water.

Before DSC measurements, the baseline, i.e., the thermopile output voltage in the absence of a differential power input, during temperature scanning in the range of interest was recorded with both calorimetric channels filled with buffer solutions. After which, characterizations of biomolecules were performed with the calorimetric channels, respectively filled with a biological sample and a buffer solutions, and scanned in the same range with pre-specified rate. The temperature sensors were used to monitor the temperatures of calorimetric channels, while the device output was obtained in real time to compute the biomolecular thermal power.

Figure 39:
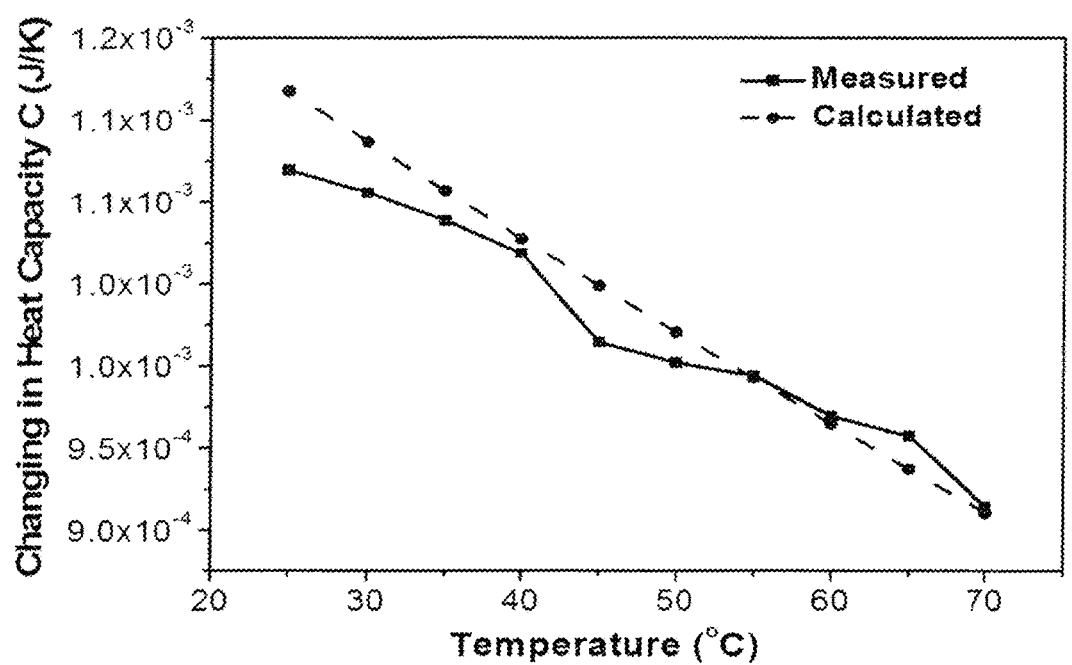
FIG. 39 is a graph showing the change in heat capacity versus temperature as measured in accordance with one embodiment of the disclosed subject matter as compared with calculated values.
Figure 40B:
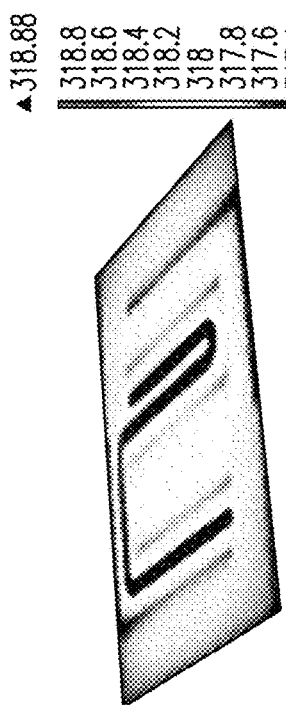
FIG. 40 shows temperature distribution within a microfluidic structure in accordance with one embodiment of the disclosed subject matter.
Figure 40D:
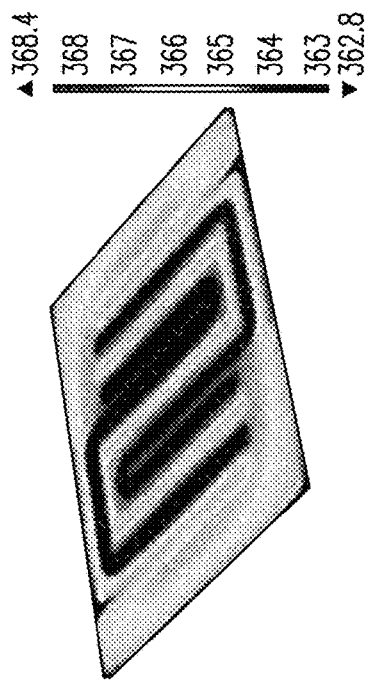
Figure 40A:
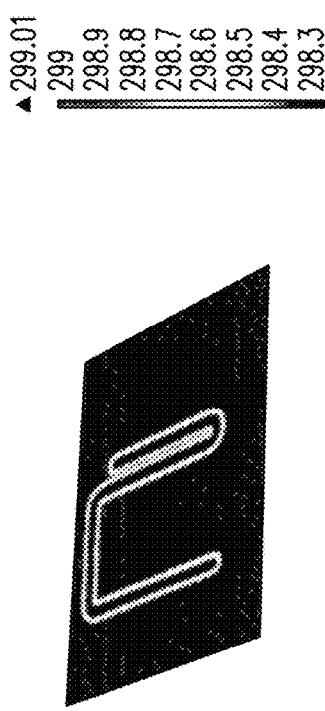
Figure 40C:
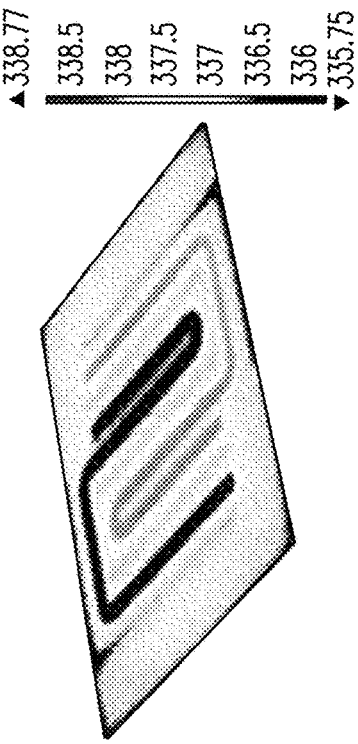

The polymer DSC device was calibrated to determine the responsivity of the device output. The device temperature was first scanned with both calorimetric channels filled with air to account for the effect of calorimetric channel volume mismatches. Then, water and glycerol were successively introduced into the sample channel, while the reference channel remained filled with air. The heat capacities of all materials were obtained from the literature. The device responsivity was determined using:

$$\Delta C_p = \frac{\Delta P}{\dot{T}} = \frac{\Delta U}{S\dot{T}} \quad (7)$$

where $\Delta U$ is the measured thermopile output voltage, $\dot{T}$ is the constant rate (scanning rate) at which the sample and reference temperature are varied in the range of interest, and S the device responsivity determined via device calibration, i.e., the thermopile output voltage per unit differential power. The device responsivity was used later for determining the sample heat capacity. All calibration experiments were thermally scanned with a rate of 3 K/min to be consistent with reported measurements in literature. The device responsivity was then determined to be 4.78 mV/mW. As shown in FIG. 39, when the device responsivity, S, and scanning rate, $\dot{T}$, are substituted back into Equation 7, the experimentally determined change in heat capacity between glycerol and water as a function of temperature agree with the calculation using data reported in the literature. We also observed an experimental output voltage noise level of approximately 100 nV in the DSC detection system, which correlated to a differential power noise of 21 nW.

Numerical analysis of heat transfer in the polymeric MEMS DSC device was also performed to assess the temperature uniformity and verify the responsivity of the device. Using COMSOL (version 4.4), the three-dimensional model which includes water filled polymeric microstructures, thermopile junctions, Kapton substrate and all the passivation layers in between, accounts for heat conduction inside the device and convection from the device's outer surfaces to the ambient. The model assumes steady state transfer at each temperature during the temperature ramping process, which occurs at a low rate (5 K/min).

Natural convection inside the microchannels is neglected in the simulation. Natural convection in the water can be characterized by the Rayleigh number, $$Ra_H = \frac{g\beta\Delta T_{max}H^3}{\alpha v}$$

where H is the height of the channel, $\alpha$ thermal diffusivity, $\beta$ the coefficient of volumetric thermal expansion, v kinematic viscosity of water, g the gravitational acceleration, and $\Delta T_{max}$ the maximum temperature difference between ambient and device layer of interest. For the condition where a constant temperature boundary condition is applied, natural convection can be considered negligible if $Ra_H<1708$. For the geometry and operating conditions ($\Delta T_{max}$ up to 70° C.) of the device, it is estimated that $Ra_H \sim 1.6E-06$. It follows that the neglect of the natural convection in the channel is justified.

The model uses the following boundary conditions. Neglecting the thermal contact resistance at the interface of the substrate and the underlying Peltier heater, the back side of the Kapton substrate is prescribed at the temperature of the heater surface. The convection coefficient h, representing the natural convection from the outer surfaces of the device to the ambient, is obtained using a correlation in the Nusselt number, which is defined by Nu=hL/k and represents the relative significance of convection to conduction. Here, k is the thermal conductivity of the air, L the characteristic length (height of the PDMS) For natural convection above a flat isothermal plate, the Nusselt number is given by the correlation Nu=0.59*$Ra_{air}^{0.25}$, where $Ra_{air}$ is the Rayleigh number for air.

A power generation of 3 mW is applied to the entire sample channel to represent the biological heat generation during the experiments. The thermal conductivity, specific heat capacities and mass densities of the fluids are temperature dependent and are accounted for in the COMSOL simulations. The temperature distribution within the microfluidic structure is shown in FIG. 40. Temperature distribution of the device when substrate is prescribed with temperature: (A) 298 K (B) 318 K (C) 338 K (D) 368 K. h is estimated as 5.18, 9.89, 11.57, 13.06 W $M^{-2}$ $K^{-1}$ accordingly. The thermal conductivities of antimony, bismuth, Kapton, PDMS are given nominal values of 24.4, 7.97, 0.12, 0.15 W $m^{-1}$ $K^{-1}$, respectively. It can be shown that the maximum temperature difference between the sample and reference channel is approximately 6° C. when the substrate temperature was prescribed to 95° C., indicating the excellent thermal insulation of the polymer DSC device.

To estimate the device responsivity, the average temperature difference across thermopile hot/cold junctions is obtained first from simulation results (varies between 0.6 to 1° C.). Equation 7 is then used to obtain the device responsivity to be 4.09 mV/mW, which is consistent with the experimentally obtained value of 4.78 mV/mW, with the deviation attributable to variations in sensor geometries and material properties that are commonly process-dependent. This device responsivity has been found to differ by no more than 15% at different substrate temperatures ranging from 298 to 368 K.

Figure 41:
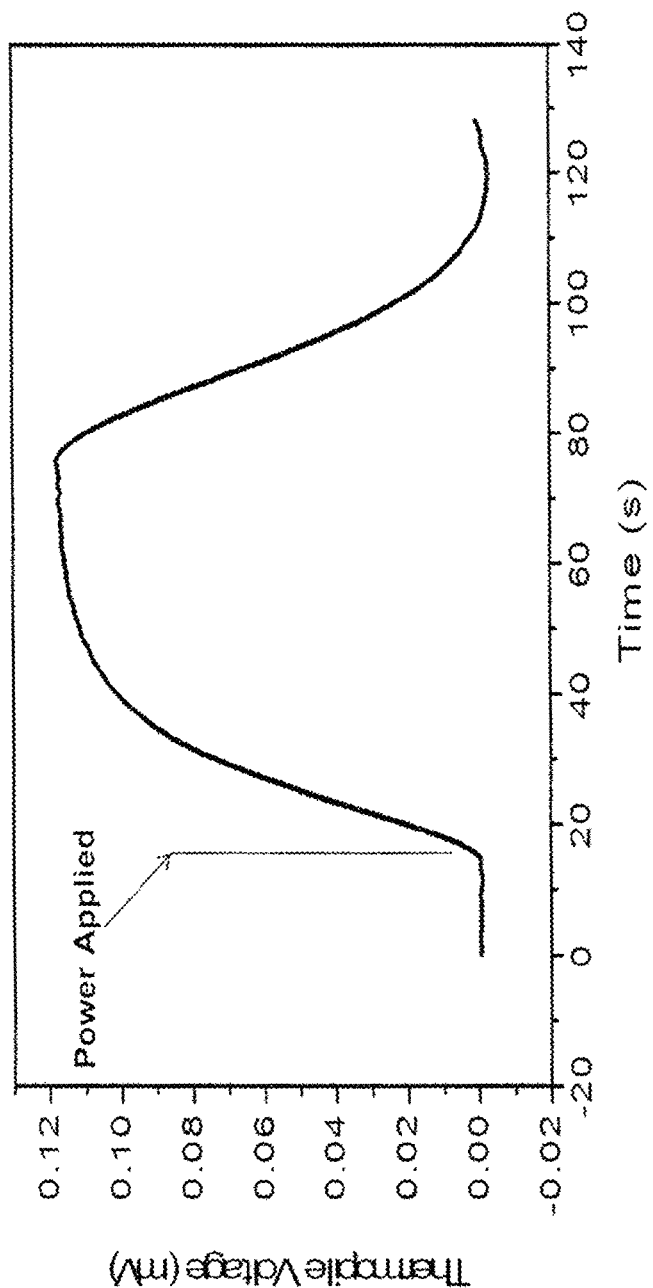
FIG. 41 shows transient responses to a unit step power in accordance with one embodiment of the disclosed subject matter.

To characterize the device time response of the MEMS DSC device, a constant differential power was initially applied to the calorimetric channels until the device output reached its equilibrium. The corresponding output voltage from the thermopile (FIG. 41) was found to exponentially grow with time upon the application of the differential power while decay exponentially upon the removal of the differential power. The thermal time constant was approximately 2.6 s, calculated by fitting the experimental data to first-order exponential growth and decay functions.

The calibrated polymer MEMS DSC device was then exploited to characterize protein unfolding. Glycine-HCl buffer (0.1 M, pH 2.5) was filled in both sample and reference calorimetric channels while the device was scanned at a constant rate of 5 K/min. After the scan was completed, the device was allowed to cool to room temperature and a second experiment under identical conditions was performed to test the stability of the baseline. There was minimal fluctuation between the two baselines. Notably, a non-zero slope was apparent at elevated temperatures, possibly as a result of the volumetric mismatch between the reference and sample channels.

Figure 42:
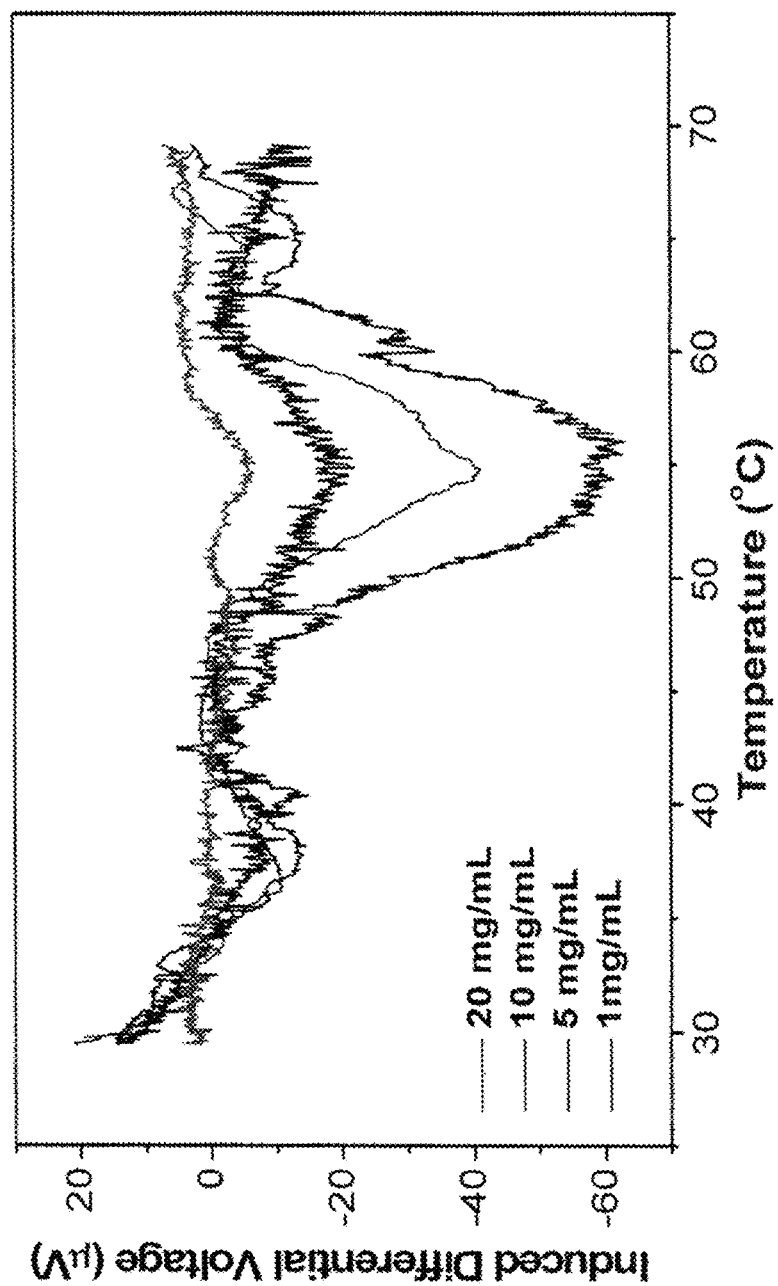
FIG. 42 is a graph showing thermopile differential voltage as a function of temperature, corrected by baseline subtraction, as measured at varying concentrations from 1 to 20 mg/mL in accordance with one embodiment of the disclosed subject matter.

Following the measurement of the baseline, lysozyme in 0.1 M Glycine-HCL buffer (pH 2.5) was introduced into the device sample channel while the reference channel remained filled only with buffer. The characterization of the unfolding of lysozyme was carried out with identical experimental conditions used in the baseline determination. The thermopile differential voltage as a function of temperature, corrected by baseline subtraction, was measured at varying concentrations ranging from 1 to 20 mg/mL (FIG. 42). The device output exhibited an endothermic thermodynamic profile within the 25-75° C. temperature range at all protein concentrations. Notably, the unfolding of lysozyme was detectable at 1 mg/mL. Furthermore, the differential heat capacity as a function of temperature and the calibrated device sensitivity can be calculated from the device voltage output by Equation 7. The sample heat capacity as a function of temperature was determined by:

$$C_{sample} = C_{buffer}\left(\frac{v_{sample}}{v_{buffer}}\right) + \left(\frac{\Delta C_p}{m_{sample}}\right) \quad (8)$$

where $v_{sample}$ and $v_{buffer}$ are the partial specific volumes of the sample and the buffer respectively, $m_{sample}$ is the mass of the biomolecule in the sample channel, and $c_{buffer}$ is the partial specific heat capacity of the buffer. The interpretation of the fundamental thermodynamic properties, such as the total enthalpy change per mole of lysozome ($\Delta H$) and melting temperature ($T_m$ defined as the temperature at which the enthalpy change achieves 50% of $\Delta H$) associated with this conformational transition can then be determined.

Figure 43:
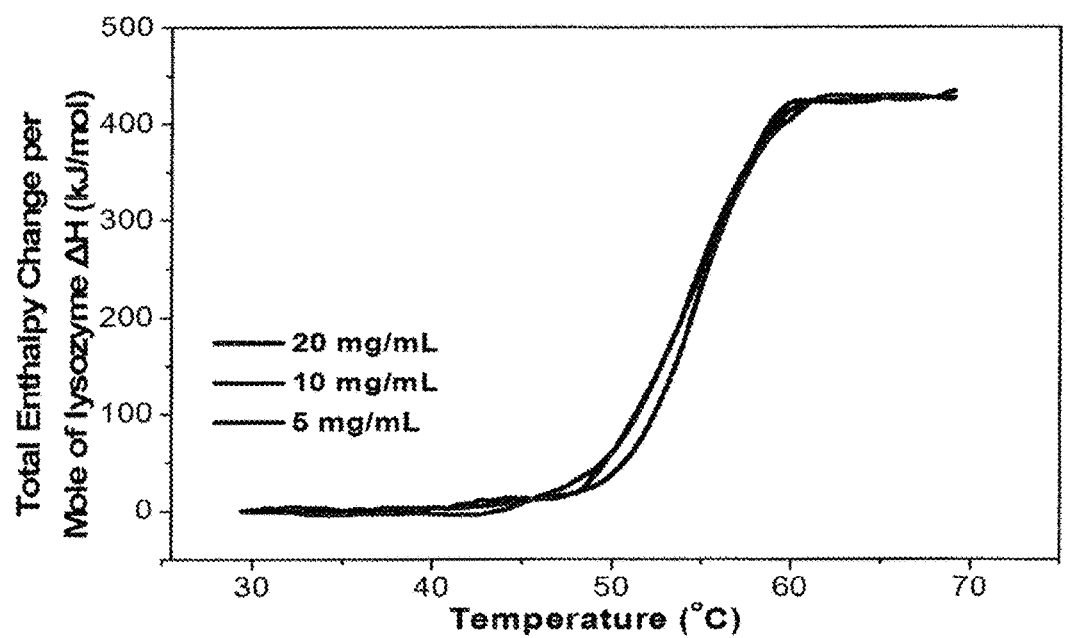
FIG. 43 is a graph showing total enthalpy change per mole of lysozome unfolding as a function of temperature at different lysozome concentrations in accordance with one embodiment of the disclosed subject matter.

The enthalpy change was determined by:

$$\Delta H(T) = \int_{T_0}^{T_1} C_{sample}(T)dT \quad (9)$$

from all protect concentrations except 1 mg/mL, which was excluded from the calculations due to the high noise in the thermopile output. As shown in FIG. 43, $\Delta H$=421 kJ/mol obtained consistently, with a corresponding melting temperature $T_m$=54.71° C. These results agree with the published data, and thus demonstrate the capability of the polymer MEMS DSC device for highly sensitive detection of biomolecular interactions.

Example 7: A Polymeric MEMS-Based Isothermal Titration Calorimeter

Figure 46:
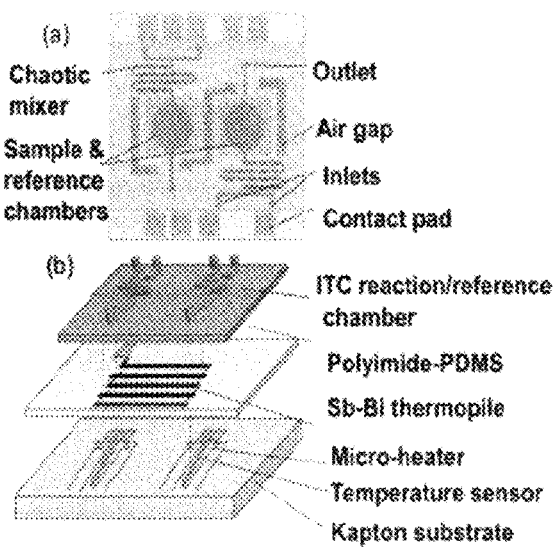
FIG. 46 depicts top and isometric views of a schematic of a microdevice in accordance with an exemplary embodiment of the disclosed subject matter.

A MEMS calorimetric device (FIG. 46) includes two identical microfluidic chambers that contain the sample and a reference buffer respectively. The chambers are integrated with passive chaotic micro-mixers downstream of the inlet. An antimony-bismuth thermopile (50 junctions) was integrated with its hot and cold junctions located beneath the center of the chamber. During operation, the sample and titrant introduced to the device were mixed in the micromixers, and then enter the sample chamber. Simultaneously, the sample and buffer are also introduced, becoming mixed before entering the reference chamber. The temperature difference between the chambers due to the reaction was then measured using the thermopile, and was used to determine the thermodynamic parameters.

Figure 47:
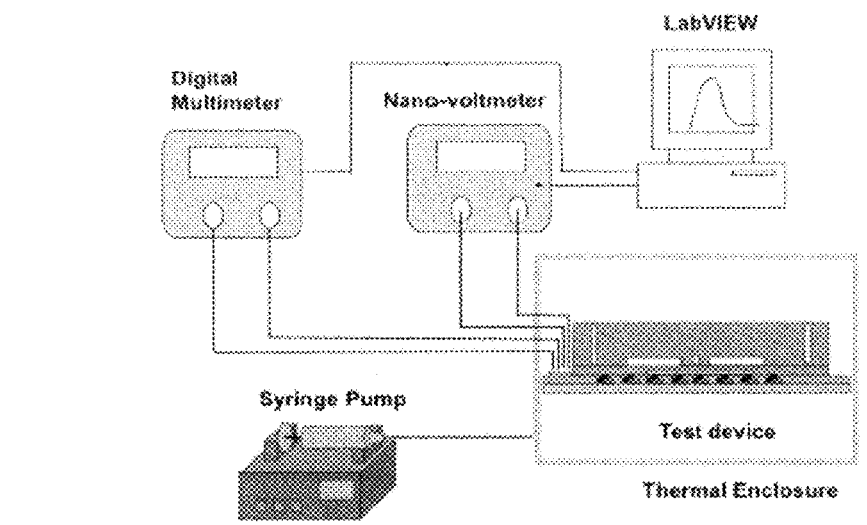
FIG. 47 is a schematic diagram showing an experiment setup for ITC measurements according to some embodiments of the disclosed subject matter.

An example setup is shown in FIG. 47. During operation, the MEMS device was first placed in a thermal enclosure which included a metal cap surrounding an aluminum stage to provide further thermal isolation of the device from ambient and minimize environmental noise. Then, the sample and titrant were introduced to the microfluidic chambers by a syringe pump. The signal of temperature sensor, calibrated before use, was measured by a digital multimeter (Agilent 34410A), and provided in situ temperature monitoring. Finally, the signals from multimeter and nano-voltmeter were collected automatically through Labview (National Instruments, Austin, Tex.).

Figure 48:
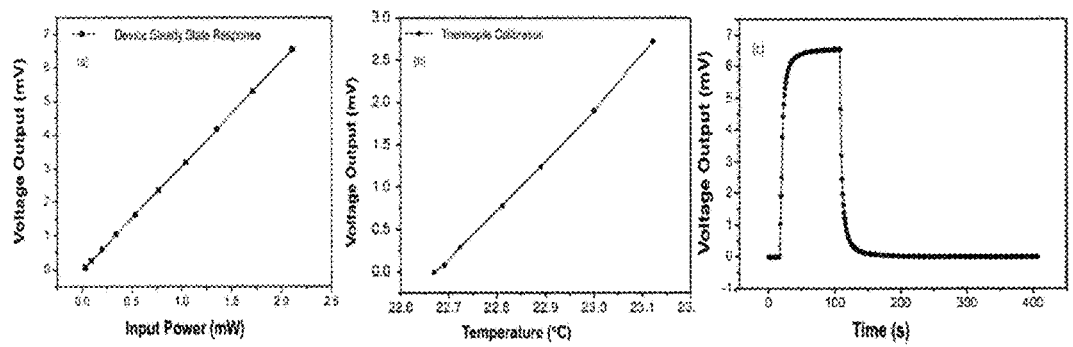
FIG. 48 a-c shows calibration of a microdevice in accordance with one embodiment of the disclosed subject matter.
Figure 49:
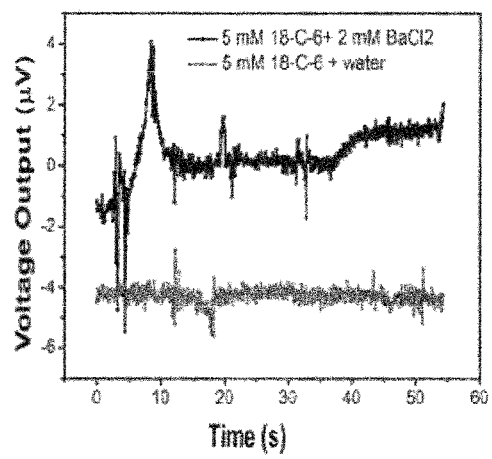
FIG. 49 is a graph showing the output upon introduction of 5 mM 18-C-6 and 2 mM $BaCl_2$ compared with water baseline for an exemplary device in accordance with the disclosed subject matter.

The device's thermopile junctions were calibrated to have an average seebeck coefficient of 6.1 mV/° C., and the device had a linear steady-state thermal response of 3.11 mV/mW (FIGS. 48a and 48b) and a thermal time constant of 2.1 s (FIG. 48c) which are sufficient for measuring the thermal power generated in typical biomolecular reactions. The device was used for calorimetric measurements of barium chloride ($BaCl_2$) and 18-Crown-6 (18-C-6). The time-resolved device output exhibited a flat baseline throughout the measurements and a reaction-specific spike (FIG. 49) 10-20 s after the introduction of 2 mM $BaCl_2$ and 5 mM 18-C-6 (each 0.5 L). Note the reagent injection time was less than 2 s using a flow rate of 50 μL/min and the heat produced from fluid injection is then considered negligible.

Figure 50A:
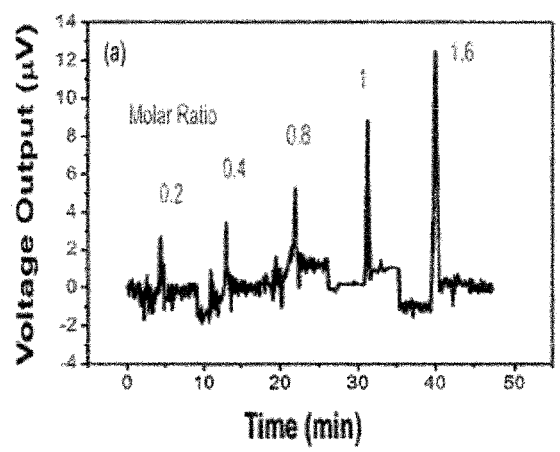
FIGS. 50a and 50b show measured binding properties for an exemplary device in accordance with the disclosed subject matter.
Figure 50B:
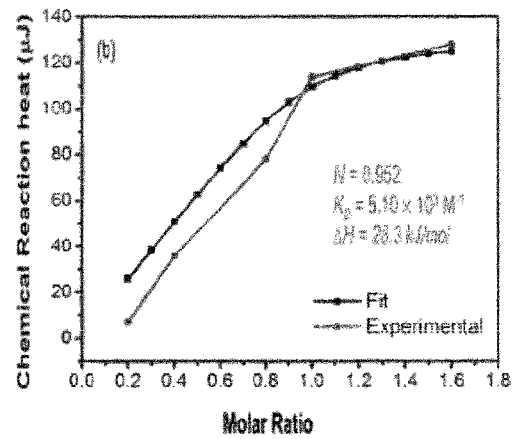

The baseline-subtracted device output demonstrated spikes corresponding to the reactions where the molar ratio ($BaCl_2$/18-C-6) was varied from 0.2 to 1.6 (FIG. 50a). Each calorimetric experiment was performed with a definite molar ratio, and a total of five discrete measurements were performed. The measured thermopile voltage was then translated into thermal power and the heat evolved in each of the 5 reactions was calculated. A binding isotherm, constructed from the reaction heat, was then fitted to an established analytical model from which the parameter of the interaction can be determined (FIG. 50b). Calorimetric measurements of the reaction of $BaCl_2$ and 18-C-6 at controlled temperatures of 25° C. were then performed and the resulting binding isotherms were used to computer the temperature-dependent thermodynamic properties of binding stoichiometry (N), binding affinity ($K_B$), and enthalpy change (ΔH), as shown in Table 2. These properties obtained by the measurements agree reasonably with published data using commercial calorimeters.

TABLE 2

| | Temperature (° C.) | N | $K_B$ ($M^{-1}$) | ΔH (kJ/mol) |
|---|---|---|---|---|
| Polymeric Calorimeter | 25 | 0.952 | $5.10 \times 10^3$ | 28.3 |
| Published Data | 25 | 1.01 | $5.63 \times 10^3$ | 29.9 |

Example 8: Polymeric MEMS Device Using 3D Diffusive Titration for Isothermal Titration Calorimetry A polymeric MEMS calorimetric device which integrates a 3D micromixer and an antimony-bismuth thermopile, is presented and was used for determining the binding paramteters of 18-Crown-6 reacting with barium chloride in a 450 nL volume. The device was calibrated to have a responsivity of 2.5 mV/mW and a detection limit of 50 nW.

Figure 51:
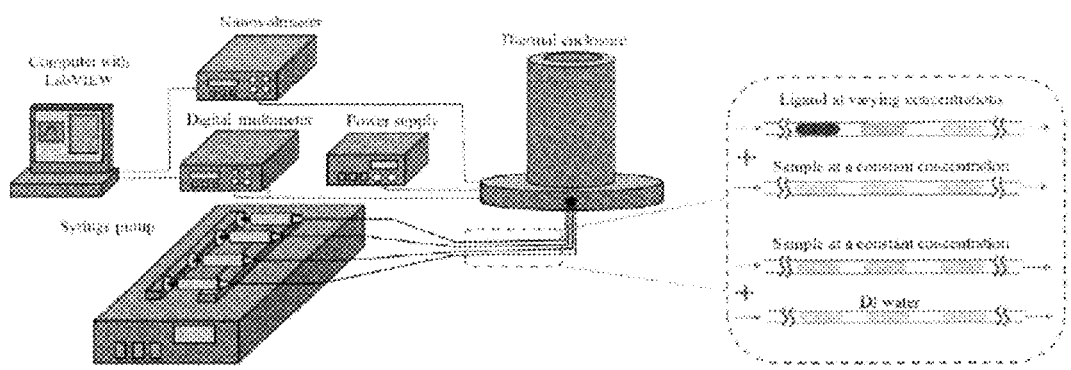
FIG. 51 is a schematic diagram showing an experiment setup for ITC measurements according to some embodiments of the disclosed subject matter.

The MEMS calorimetry device (FIG. 44) can include two 3-D splitting-and-recombination (SAR) micromixers which serve as fluidic channels that contain a sample and a reference buffer. The 3D diffusive titration channels were integrated with an antimony-bismuth thermopile with hot and cold junctions vertically aligned with the fluidic channels' center, combining the functionalities of micromixing, titration, and thermoelectric transducing. By integrating the thermopile with the titration channels, the reaction heat during mixing were measured and heat loss during mixing was eliminated. The disclosed device used a low-Reynolds-number flow (Re 2) during titration process to minimize flow induced measurement noise. During operation, the binding reagent at varying concentrations as drawn into a plastic tubing by a multi-channel syringe pump, and separated by small air gaps. Simultaneously, the same concentration of sample and buffer were also drawn into their respective tubes using the same syringe pump. The sample and binding reagent introduced to the device were mixed along the sample channel while the sample and buffer were introduced, and mixed along the reference channel. The temperature difference between the channels due to the reaction was then measured using the thermopile, and used to obtain the thermodynamic properties of the reaction system. The device fabrication (FIG. 45) included two parallel processes. The MEMS thermoelectric transduction part was fabricated using standard MEMS technology. The 3D passive SAR micromixers (microfluidic channels) were fabricated using standard soft lithography. The two parts were bonded together using oxygen plasma, and were precisely aligned under an optical microscope. The microfabricated MEMS device was placed in a thermal enclosure (FIG. 51) during calorimetric measurements to minimize environmental noise.

In connection with ITC analysis to be described below for the thermodynamic characterization of a ligand-receptor reaction system, the ligand with known concentration and volume was titrated or added into a receptor. The reaction heat was obtained as a function of the ligand-receptor molar ratios. For example, considering a biochemical reaction system in which a receptor (M) and a ligand (X) bind in equilibrium and form the complex Mα Xβ:

$$aM + \beta X \rightleftharpoons M_\alpha X_\beta \qquad (10)$$

where α, β are the stoichiometric coefficients of the receptor and the ligand, respectively.

Figure 52:
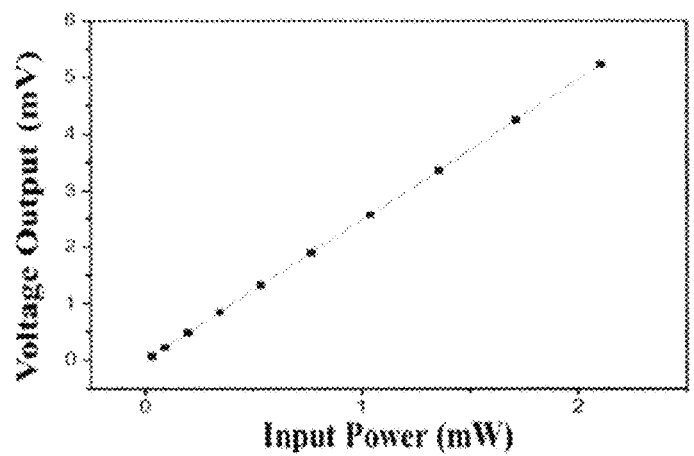
FIG. 52 is a graph showing the steady state response of an exemplary device in accordance with the disclosed subject matter.
Figure 53:
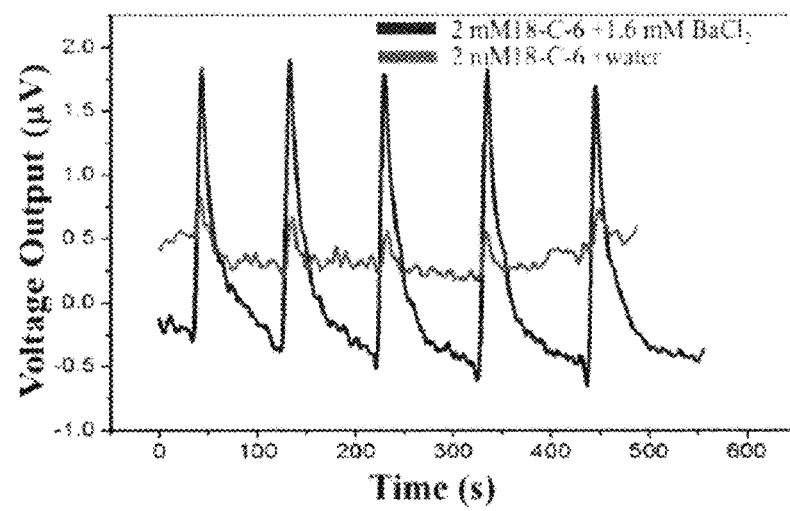
FIG. 53 is a graph showing the time-resolved output upon introduction of a sample compared with the water baseline of an exemplary device in accordance with the disclosed subject matter.
Figure 54:
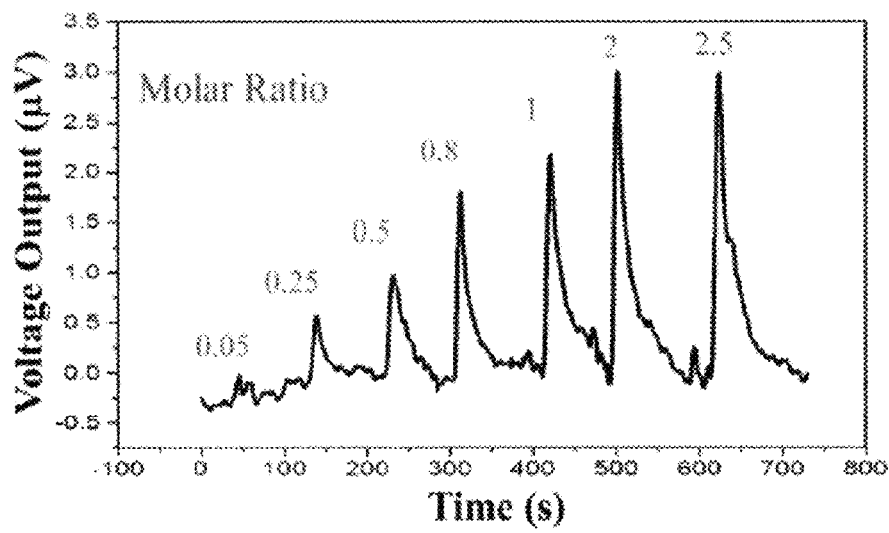
FIG. 54 is a graph showing the voltage output of the 2 mM 18-C-6 reacting with $BaCl_2$ at different molar ratios for an exemplary device in accordance with the disclosed subject matter.

The device was calibrated by measuring its steady-state thermopile output from an applied differential thermal power (FIG. 52). A linear relationship was obtained with a responsivity of 2.5 mV/mW. Using a model reaction system of 18-C-6 and $BaCl_2$ the time-resolved device output showed reaction-specific spikes within 5 sec. of injection (FIG. 53), indicating effective mixing of the reactants. In addition, to demonstrate the repeatability of calorimetric measurements, five consecutive injections of the reagents with the same concentration were administered, and the reaction heat induced spikes were compared with 5 injections of the reference solution. As a result, a repeatable signal-to-noise ratio of ~6 (appropriate for titration measurements) was observed. Also, the device returned to its equilibrium state between titration experiments within approximately 4 minutes. Next, calorimetric measurements of 18-C-6 and $BaCl_2$ were performed at controlled temperatures of 25° C. The baseline-subtracted device output (FIG. 54) had increasing reaction specific peak values when the molar ratio of the reactants ($BaCl_2$/18-C-6) increased from 0.5 to 2.5. Notably, there was no observable change in peak value from a molar ratio of 2.0 to 2.5, indicating excessive $BaCl_2$ induced saturation. This was expected for the reaction system. The reaction thermal power was determined by fitting this binding isotherm to a one-site binding model. The equilibrium binding constant, stoichiometry, and total enthalpy change of the reaction system were determined to be 6000 $M^{-1}$, 1.01, and −34 kJ/mol, respectively. These results were found to agree with the published data.

Figure 55:
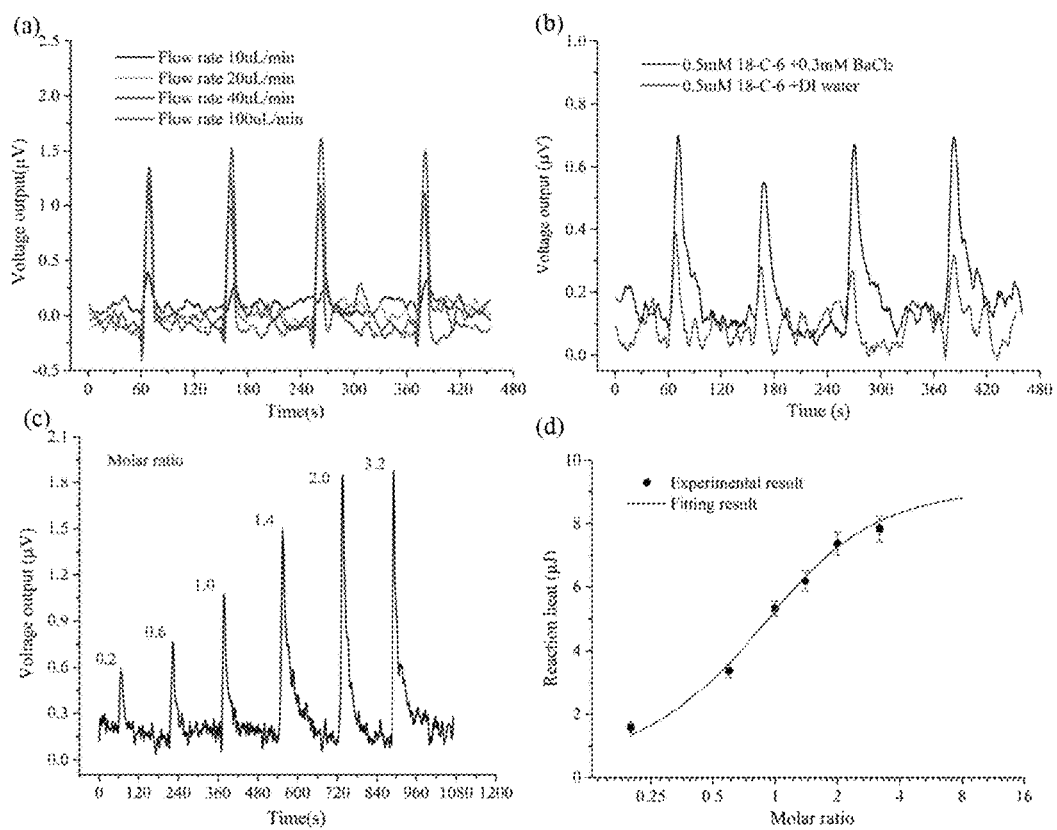
FIG. 55a-d shows measured binding properties with 3.7 mv constant responsivity for an exemplary device in accordance with the disclosed subject matter.

In certain embodiments, the device was calibrated to have a responsivity of 3.7 mV/mW at 298 K (FIG. 55). The responsivity of the device at controlled microdevice temperature between 20° C. to 40° C. remained constant with a relative standard deviation of less than 3%. A device time response of 800 ms was obtained using the ITC microdevice. The on-chip heater was used to generate a rectangular electrical calibration pulse (1 mW) to the reaction chamber.

The decay portion of the instrument response was fitted to a multiple exponential decay function to determine the time response.

The overall baseline was measured by introducing sterile water and 0.1-1.6 mM $BaCl_2$ to the reaction chamber and reference chamber, respectively. In order to determine an improved condition, four sequential injections of the reagents were administered, each with a 1.5-minute interval, and the flow rate ranged from 10 to 100 µL/min. The increase in flow rate directly caused the baseline nose to increase monotonically (FIG. 55a). There was an approximately 7% volume difference (primarily in thickness) existing between sample/reference channels and viscous heating effects generated a non-specific heating contribution (baseline noise) due to volume difference during ITC measurement. At the flow rate 10 µL/min, all four measurements illustrated a similar non-reaction-specific heat contribution of ~25 nW and were subtracted from the sample analysis as shown in FIG. 55a. The 25 nW was the detection limit of the ITC microdevice, which was adequate for measuring the thermal power generated in biomolecular interactions.

To compare the selected baseline noise with the reaction heat induced differential power, four injections of 0.3 mM $BaCl_2$ and 0.5 mM 18-C-6 (each 0.23 were introduced to the reaction chamber. Compared with the baseline, the ITC microdevice exhibits a reaction-specific spike attributable to the exothermic nature of the binding between 18-C-6 and $BaCl_2$ (FIG. 55b) and is three time larger in peak value than the baseline noise. The baseline was valid if and only if it was completed in the same testing condition as described in connection with the following ITC analysis. Baseline testing was performed prior to the ITC analysis.

The thermodynamic binding parameters between $BaCl_2$ and 18-C-6 were characterized to demonstrate the potential towards complete ITC measurements as shown in FIG. 55c. The ITC microdevice was used in a series of measurements at the controlled temperature of 298 K. Each measurement used a fixed concentration of 18-C-6 (0.5 mM) and a series of concentrations of BaCl2 (in the range of 0.1~1.6 mM), allowing the molar ratio of $BaCl_2$ to 18-C-6 to be varied from 0.2 to 3.2. By varying the molar ratio (MBaCl2/M18-C-6) from 0.2 to 3.2, the baseline-subtracted device output illustrated spikes consistent with the titration reactions as shown in FIG. 55c. Each spike in the device output corresponded to each titration, with a magnitude increasing consistently with the increase of the molar ratio. Excessive ligand ($BaCl_2$) concentration at molar ratio of 3.2 and the reaction was saturated at molar ratio of 2.

In certain embodiments, thermopile voltage output measured from the microdevice was used to calculate the differential thermal power. The reaction heat at each molar ratio can be calculated by integrating the thermal power over the entire period of reaction time. A thermodynamic binding isotherm (FIG. 55d) was obtained by plotting the reaction heat as a function of the molar ratio, and a least square fitting to Equation (3) was used to determine the full thermodynamic parameters of the reaction system. The reaction heat increased monotonically with the molar ratio until approaching saturation (molar ratio of 2) reflecting that the more binding sites of 18-C-6 were occupied with the addition of $BaCl_2$ until the binding sites were no longer available and excessive $BaCl_2$ became free ligand in solution. The error bar was a result of standard deviation between the calculation of the reaction heat for three separate ITC tests.

From the least square besting fitting curve (FIG. 55d), the stoichiometry was approximately n=0.99 at 298K, corresponding to the one to one binding of 18-C-6 and BaCl2.

The reaction association constant Ka was determined to be $6.09 \times 10^3$ M-1. The molar enthalpy change ΔH was 31.0 kJ/mol at 298 K. These properties were within 5% difference with published data using conventional instruments at the same temperature.

The description herein merely illustrates the principles of the disclosed subject matter. Various modifications and alterations to the described embodiments will be apparent to those skilled in the art in view of the teachings herein. Further, it should be noted that the language used herein has been principally selected for readability and instructional purposes, and cannot have been selected to delineate or circumscribe the inventive subject matter. Accordingly, the disclosure herein is intended to be illustrative, but not limiting, of the scope of the disclosed subject matter.

The invention claimed is:

1. A microdevice for calorimetric measurement comprising:
    a reference channel comprising a first passive mixer;
    a sample channel comprising a second passive mixer; and
    a thermoelectric sensor located under each of the first and second passive mixers and configured to measure a temperature differential therebetween,
    wherein each of the first and second passive mixers comprises a micromixer and is configured for three dimensional mixing of a solution,
    wherein each of the first and second passive mixers comprises a first set of channels in a first horizontal plane and a second set of channels in a second horizontal plane,
    wherein each of the first and second passive mixers are formed by a top layer and a bottom layer, and further wherein each of the first and second passive mixers comprise a first set of channels in the top layer and a second set of channels in the bottom layer.

2. The microdevice of claim 1, wherein the thermoelectric sensor comprises a thermopile.

3. The microdevice of claim 1, further comprising a substrate layer beneath the thermopile.

4. The microdevice of claim 3, wherein the substrate layer comprises Kapton film.

5. A microdevice for calorimetric measurement comprising:
    a first layer comprising:
        a reference channel comprising a first passive mixer; and
        a sample channel comprising a second passive mixer; and
    a second layer, coupled to the first layer, comprising a thermoelectric sensor located under each of the first and second passive mixers and configured to measure a temperature differential therebetween,
    wherein each of the first and second passive mixers comprises a micromixer and is configured for three dimensional mixing of a solution,
    wherein each of the first and second passive mixers comprises a first set of channels in a first horizontal plane and a second set of channels in a second horizontal plane,
    wherein each of the first and second passive mixers are formed by a top layer and a bottom layer, and further wherein each of the first and second passive mixers comprise a first set of channels in the top layer and a second set of channels in the bottom layer.

6. The microdevice of claim 5, wherein the reference channel comprises a first reference channel inlet and a second reference channel inlet, and the sample channel comprises a first sample channel inlet and a second sample channel inlet.

7. The microdevice of claim 5, wherein the thermoelectric sensor comprises a thermopile.

8. The microdevice of claim 5, wherein the second layer further comprises a polymeric substrate.

9. The microdevice of claim 8, wherein the polymeric substrate comprises Kapton film.

10. A microdevice for calorimetric measurement comprising:
   a first layer consisting essentially of:
      a reference channel comprising a first passive mixer, a first reference channel inlet, a second reference channel inlet, and a reference channel outlet; and
      a sample channel comprising a second passive mixer, a first sample channel inlet, and second sample channel inlet, and a sample channel outlet; and
   a second layer, coupled to the first layer, the second layer comprising a thermoelectric sensor located under each of the first and second passive mixers and configured to measure a temperature differential therebetween,
   wherein each of the first and second passive mixers comprises a micromixer and is configured for three dimensional mixing of a solution, or/and a splitting-and-recombination mixer,
   wherein each of the first and second passive mixers comprises a first set of channels in a first horizontal plane and a second set of channels in a second horizontal plane.

11. The microdevice of claim 10, wherein the thermoelectric sensor comprises a thermopile.

12. The microdevice of claim 10, further comprising a substrate layer coupled to the second layer.

13. The microdevice of claim 12, wherein the substrate layer comprises Kapton film.

14. A method of determining a thermal property of an analyte, comprising:
   providing a microdevice comprising:
      a reference channel comprising a first passive mixer;
      a sample channel comprising a second passive mixer; and
      a thermoelectric sensor located under each of the first and second passive mixers and configured to measure a temperature differential between the first and second passive mixers, wherein each of the first and second passive mixers comprises a micromixer and is configured for three dimensional mixing of a solution,
   introducing a sample material and a second substance into the sample channel;
   introducing the sample material and a buffer into the reference channel; and
   determining a thermal property of the reaction between the sample material and the second substance based on the measured temperature differential between the sample channel and the reference channel.

15. The method of claim 14, wherein providing the microdevice comprises providing a microdevice wherein the first and second passive mixers comprise splitting-and-recombination micromixers.

16. A method of determining a thermal property of an analyte, comprising:
   providing a microdevice comprising:
      a reference channel comprising a first passive mixer;
      a sample channel comprising a second passive mixer; and
      a thermoelectric sensor located under each of the first and second passive mixers and configured to measure a temperature differential between the first and second passive mixers, and further wherein each of the first and second passive mixers is configured for three dimensional mixing of a solution,
   introducing a sample material and a second substance into the sample channel;
   introducing the sample material and a buffer into the reference channel; and
   determining the heat involved in the reaction between the sample material and the second substance based on the measured temperature differential between the sample channel and the reference channel.

17. The method of claim 16, wherein providing the microdevice comprises providing a microdevice wherein the first and second passive mixers comprise splitting-and-recombination micromixers.

18. A microdevice for calorimetric measurement comprising:
   a reference channel comprising a first passive mixer;
   a sample channel comprising a second passive mixer; and
   a thermoelectric sensor located under each of the first and second passive mixers and configured to measure a temperature differential therebetween,
   wherein the reference channel comprises a 3D diffusive titration channel,
   wherein the sample channel comprises a 3D diffusive titration channel,
   wherein each of the first and second passive mixers comprises a micromixer and is configured for three dimensional mixing of a solution,
   wherein each of the first and second passive mixers comprises a first set of channels in a first horizontal plane and a second set of channels in a second horizontal plane,
   wherein each of the first and second passive mixers are formed by a top layer and a bottom layer, and further wherein each of the first and second passive mixers comprise a first set of channels in the top layer and a second set of channels in the bottom layer.

19. The microdevice of claim 18, wherein the thermoelectric sensor comprises a thermopile.

20. The microdevice of claim 18, further comprising a substrate layer beneath the thermopile.

21. The microdevice of claim 20, wherein the substrate layer comprises Kapton film.

22. The microdevice of claim 18, wherein the microdevice comprises a polymeric MEMs-based microdevice.

* * * * *